US006262283B1

(12) United States Patent
Kinney et al.

(10) Patent No.: US 6,262,283 B1
(45) Date of Patent: *Jul. 17, 2001

(54) STEREOSELECTIVE SYNTHESIS OF 24-HYDROXYLATED COMPOUNDS USEFUL FOR THE PREPARATION OF AMINOSTEROLS, VITAMIN D ANALOGS, AND OTHER COMPOUNDS

(75) Inventors: William A. Kinney, Richboro; Steven Jones, West Chester; Xuehai Zhang, E. Norriton; Meena N. Rao, Lansdale, all of PA (US); Michel Bulliard, Angers (FR); Harold Meckler, Delmar, NY (US); Nancy Lee, Foxboro, MA (US)

(73) Assignee: Magainin Pharmaceuticals Inc., Plymouth Meeting, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/985,876

(22) Filed: Dec. 5, 1997

Related U.S. Application Data

(60) Provisional application No. 60/032,378, filed on Dec. 6, 1996.

(51) Int. Cl.[7] .................................................. C07J 41/00
(52) U.S. Cl. ............................................................ 552/521
(58) Field of Search ............................................. 552/521

(56) References Cited

U.S. PATENT DOCUMENTS

| 3,016,390 | 1/1962 | Counsell ........................... 260/397.3 |
|---|---|---|
| 3,370,070 | 2/1968 | Klimstra et al. .................. 260/397.3 |
| 4,220,598 | 9/1980 | Hixson, Jr. et al. .............. 260/397.1 |
| 4,372,888 | 2/1983 | Hjelmeland ....................... 260/397.1 |
| 4,425,273 | 1/1984 | Iida et al. .......................... 262/397.1 |
| 4,514,393 | 4/1985 | Castagnola et al. .............. 260/397.1 |
| 4,545,938 | 10/1985 | Mosbach et al. ................ 260/397.1 |
| 4,550,163 | 10/1985 | Voss et al. ............................ 544/244 |
| 4,565,811 | 1/1986 | Di Schiena .......................... 514/182 |
| 4,771,042 | 9/1988 | Braughler et al. .................. 514/171 |
| 4,793,948 | 12/1988 | Hatono et al. ................... 260/397.1 |
| 4,966,897 | 10/1990 | Angelastro et al. ................ 514/177 |
| 4,994,443 | 2/1991 | Folkman et al. ...................... 514/56 |
| 5,001,116 | 3/1991 | Folkman et al. ............... 260/397.45 |
| 5,004,737 | 4/1991 | Kim et al. ........................... 514/182 |
| 5,039,529 | 8/1991 | Bergendal et al. .................. 424/630 |
| 5,057,509 | 10/1991 | Pellicciari et al. ................. 514/182 |
| 5,061,701 | 10/1991 | Pellicciari et al. ................. 514/182 |
| 5,063,222 | 11/1991 | Komoto et al. ..................... 514/180 |
| 5,075,464 | 12/1991 | Blohm et al. ....................... 552/522 |
| 5,135,919 | 8/1992 | Folkman et al. ...................... 514/56 |
| 5,192,756 | 3/1993 | Zasloff et al. ....................... 514/182 |
| 5,247,104 | 9/1993 | DeLuca et al. ..................... 552/653 |
| 5,250,524 | 10/1993 | Kramer et al. ...................... 514/177 |
| 5,637,691 | 6/1997 | Frye et al. ............................ 540/106 |

FOREIGN PATENT DOCUMENTS

| 0 394 971 A1 | 10/1990 | (EP) . |
|---|---|---|
| 0 466 315 A2 | 1/1992 | (EP) . |
| 2 361 899 | 3/1978 | (FR) . |
| 1 565 351 | 4/1980 | (GB) . |
| WO87/02367 | 4/1987 | (WO) . |
| WO91/19731 | 12/1991 | (WO) . |
| WO93/25197 | 12/1993 | (WO) . |
| 94/17079 | 8/1994 | (WO) . |
| WO94/19366 | 9/1994 | (WO) . |
| WO94/20520 | 9/1994 | (WO) . |
| WO95/24415 | 9/1995 | (WO) . |
| WO96/40151 | 12/1996 | (WO) . |
| WO97/40728 | 12/1996 | (WO) . |

OTHER PUBLICATIONS

Brown et al., "Selective Reductions. 40. A Critical Examination of the Relative Effectiveness of Various Reducing Agents for the Asymmetric Reduction of Different Classes of Ketones", *J. Org. Chem.*, vol. 52, No. 24, pp. 5406–5412 (1987).

Wallbaum et al., "Asymmetric Syntheses with Chiral Oxazaborolidines", *Tetrahedron: Asymmetry*, vol. 3, No. 12, pp. 1475–1504 (1992).

Corey et al., "A Stable and Easily Prepared Catalyst for the Enantioselective Reduction of Ketones. Applications to Multistep Syntheses", *J. Am. Chem. Soc.*, vol. 109, No. 25, pp. 7925–7926 (1987).

Okamoto et al., "Asymmetric Isopropylation of Steroidal 24–aldehydes for the Synthesis of 24(R)–hydroxycholesterol", *Tetrahedron: Asymmetry*, vol. 6, No. 3, pp. 767–778 (1995).

Okamoto et al., "The First Convergent Synthesis of 1α, 24(R)–dihydroxyvitamin $D_3$ Via Diastereoselective Isopropylation and Alkylative Enyne Cyclization", *Tetrahedron*, vol. 51, No. 19, pp. 5543–5556 (1995).

Takatsuto et al., "Chirality Transfer in the Cholesterol Side Chain; Synthesis of (24R)– and (24S)–24–hydroxycholesterols", *Journal of the Chemical Society, Chemical Communications*, No. 4, pp 258–260 (1982).

(List continued on next page.)

*Primary Examiner*—S. Mark Clardy
*Assistant Examiner*—Alton Pryor
(74) *Attorney, Agent, or Firm*—Morgan, Lewis & Bockius LLP

(57) ABSTRACT

A method is described for stereoselectively reducing an unsaturated alkyl ketone substituent attached to a fused ring base. In this method, the unsaturated alkyl ketone reacts with a chiral oxazaborolidine reagent. This reaction stereoselectively reduces the unsaturated alkyl ketone to an unsaturated alkyl alcohol. The unsaturated alkyl alcohol can be further reduced, if desired, to produce a saturated alkyl alcohol. The fused ring base can be, for example, a steroid ring base or a base of a vitamin D analog. The process in accordance with the invention can be used with an alkeneone substituent (e.g., a 22-ene-24-one substituent) or an alkyneone substituent (e.g., a 22-yne-24-one substituent) on a steroid ring base to make squalamine or other useful aminosterol compounds and intermediates for making aminosterol compounds.

11 Claims, 19 Drawing Sheets

OTHER PUBLICATIONS

Ishiguro et al., "Neighbouring Group Effects. Part 2. Effect of Epoxide on the Hydrolysis Of Adjacent Acetate Groups", *Journal of the Chemical Society, Perkin Transactions 1*, No. 11, pp. 2507–2510 (1980).

Katsumi et al., "Syntheses of 24, 25–dihydroxyvitamin $D_2$, 24,25–dihydroxy–22–dehydrovitamin $D_3$, 25–hydroxy–24–oxo–22–dehydrovitamin $D_3$ and 22,24, 25–trihydroxyvitamin $D_3$", *Chemical and Pharmaceutical Bulletin*, vol. 35, No. 3, pp. 970–979 (1987).

Parker et al., "Asymmetric Reduction. A Convenient Method for the Reduction of Alkynyl Ketones", *J. Org. Chem.*, vol. 61 (9), pp. 3214–3217 (1996).

Helal et al., "Direct Catalytic Enantioselective Reduction of Achiral $\alpha,\beta$–ynones. Strong Remote Steric Effects Across the C—C Triple Bond", *J. Am. Chem. Soc.*, vol. 118(44), pp. 10938–10939 (1996).

Imai et al., "Organoboron Compounds in Organic Synthesis. 2. Asymmetric Reduction of Dialkyl Ketones with (R,R)– or (S,S)–2,5–dimethylborolane", *J. Am. Chem. Soc.*, vol. 108(23), pp. 7402–704 (1986).

Bach et al., "Highly Enantioenriched Propargylic Alcohols by Oxazaborolidine–mediated Reduction of Acetylenic Ketones", *J. Org. Chem.*, vol. 61 (25), pp. 9021–9025 (1996).

Rao et al., "Practical Approaches to Remote Asymmetric Induction in Steroidal Side–chains Utilizing Oxazaborolidine Reagents", *J. Org. Chem.*, vol. 62(13), pp. 4541–4545 (1997).

McKenna, James et al., "Bis–steroids as Potential Enzyme Models: Perylene Solubilisation and Dye Spectral Changes with Aqueous Solutions of Some Derivatives of Conessine and Cholic Acid;" *J.C.S. Chem. Comm.*, 1977, pp. 809–811.

Crum, Rosa et al., "A New Class of Steroids Inhibits Angiogenesis in the Presence of Heparin or a Heparin Fragment," Science, vol. 230, 1985, pp. 1375–1378.

Derwent Abstract No. 86–085704, "Anticancer Drug Contains Shark Liver Extract Doxorubicin," 1984.

Biosis No. 82085007, "Studies on Antitumor Activity of Squalene and Its Related Compounds," Yakugaku Zasshi, 1986.

Chemical Abstract No. 111: 17264, "Increasing the Therapeutic Efficacy of Antitumor Drugs," 1989.

Bellini, A.M. et al., "Antimicrobial Activity of Basic Cholane Derivatives, Part IX," Arch. Pharm. (Weinheim) 323, 201–205 (1990).

Bellini, Anna M. et al., Antimicrobial Activity of Basic Cholane Derivatives. X. Synthesis of $3\alpha$ –$3\beta$–amino–$5\beta$–cholan–24–oic Acids, *Steroids*, vol. 56, Jul. 1991, pp. 395–397.

Gagliardi, A., et al., "Inhibition of Angiogenesis by Antiestrogens," *Cancer Research*, 53, pp. 533–535, Feb. 1, 1993.

Moore, Karen S. et al., "Squalamine: An Aminosterol Antibiotic from the Shark," *Proc. Natl. Acad. Sci.*, USA, vol. 90, pp. 1354–1358, Feb. 1993.

Wehrli, S. et al., "Structure of the Novel Steroidal Antibiotic Squalamine Determined by Two–Dimensional NMR Spectroscopy," *Steroids*, vol. 58, No. 8, Aug. 1993, pp. 370–378.

Children's Hospital of Pennsylvania, "Aminosterol Antibiotic;" Current Opinion in Therapeutic Patents Sep. 1993, pp. 1369–1370.

Auerbach, R. et al., "Angiogenesis Inhibition: A Review;" *Pharmac. Ther.*, vol. 63, pp. 265–311, 1994.

Moriarty, Robert M. et al., "Synthesis of Squalamine, A Steroidal Antibiotic from the Shark," *Tetrahedron Letters*, vol. 35, No. 44, pp. 8103–8106, 1994.

Sadownik, Andrzej et al., "Rapid Construction of a Squalamine Mimic;" *J. Am. Chem. Soc.*, 1995, vol. 117, pp. 6138–6139.

"Shark Cartilage for Cancer Treatment," P&T Newsletter, Mar. 1996, pp. 159–160.

"Designing Therapies that Target Tumor Blood Vessels;" *Science*, vol. 275, Jan. 24, 1997, pp. 482–484.

Akhter, "Squalamine, A Novel Aminosterol Antibiotic is a Specific Inhibitor of Epithelial Brush Border $Na^+/H^+$ Exchanger Isoform, NHE3," *FASEB Journal*, vol. 10, No. 3 (1996), p. A89.

Nath, "The Novel Aminosterol Antibiotics Squalamine and 1436 are Specific Inhibitors of Epithelial Brush Border $Na^+/H^+$ Exchanger (NHE) Isoform, NHE3," *Gastroenterology*, vol. 110, No. 4, Suppl. (1996), A349.

SQUALAMINE

COMPOUND - 1436

CEREBROSTEROL

MC903

1α,24(R)-DIHYDROXYVITAMIN $D_3$

11

12

13

14

Overall yield 4%

STEREOSELECTIVE SYNTHESIS OF 24-HYDROXYLATED COMPOUNDS USEFUL FOR THE PREPARATION OF AMINOSTEROLS, VITAMIN D ANALOGS, AND OTHER COMPOUNDS

CROSS-REFERENCE TO RELATED APPLICATION

This application claims priority benefits under 35 U.S.C. § 119 based on U.S. Provisional Patent Application No. 60/032,378, which was filed Dec. 6, 1996. This provisional application is entirely incorporated herein by reference.

BACKGROUND OF THE INVENTION

Several aminosterol compositions have been isolated from the liver of the dogfish shark, *Squalus acanthias*. One important aminosterol is squalamine (3β-(N-[3-aminopropyl]-1,4-butanediamine)-7α,24ξ-dihydroxy-5α-cholestane 24-sulfate), the chemical structure of which is shown in FIG. 1. This aminosterol, which includes a sulfate group at the C-24 position, is the subject of U.S. Pat. No. 5,192,756 to Zasloff, et al., which patent is entirely incorporated herein by reference. This patent describes antibiotic properties of squalamine.

Since the discovery of squalamine, however, several other interesting properties of this compound have been discovered. For example, as described in U.S. patent application Ser. No. 08/416,883 (filed Apr. 20, 1995) and U.S. patent application Ser. No. 08/478,763 (filed Jun. 7, 1995), squalamine may function as an antiangiogenic agent. These patent applications are entirely incorporated herein by reference. Additional uses of squalamine (e.g., as an agent for inhibiting NHE3 and as an agent for inhibiting endothelial cell growth) are disclosed in U.S. patent application Ser. No. 08/474,799 (filed Jun. 7, 1995) and U.S. patent application Ser. No. 08/840,706 (filed Apr. 25, 1997). These patent applications also are entirely incorporated herein by reference.

Methods for synthesizing squalamine have been devised, such as the methods described in WO 94/19366 (published Sep. 1, 1994). This PCT publication is entirely incorporated herein by reference. This PCT application relates to U.S. patent application Ser. No. 08/023,347, which application also is entirely incorporated herein by reference. Additionally, U.S. patent application Ser. No. 08/474,799 also discloses squalamine isolation and synthesis techniques.

Stemming from the discovery of squalamine, other aminosterols have been discovered in the dogfish shark liver and have been investigated. One important aminosterol that has been isolated and identified has the structure shown in FIG. 2. In this application, the compound having the structure shown in FIG. 2 will be referred to as "compound 1436" or simply "1436." This compound has the general molecular formula $C_{37}H_{72}N_4O_5S$ and a calculated molecular weight of 684.53017. Like squalamine, this aminosterol also has a sulfate group at the C-24 position.

Compound 1436 previously has been described in U.S. patent application Ser. Nos. 08/483,057 and 08/487,443, each filed Jun. 7, 1995. Each of these U.S. patent applications is entirely incorporated herein by reference. As further described in these patent applications, compound 1436 has a variety of interesting properties. For example, compound 1436 inhibits human T-lymphocyte proliferation, as well as the proliferation of a wide variety of other cells and tissues. Additional uses of compound 1436 are disclosed in U.S. Provisional Patent Appl. No. 60/017,627 (filed May 17, 1996) and the subsequently filed U.S. patent application Ser. No. 08/857,288 filed May 16, 1997 and U.S. patent application Ser. No. 08/962,290 filed Oct. 31, 1997. These patent applications also are entirely incorporated herein by reference.

U.S. patent application Ser. Nos. 08/483,057 and 08/487,443 describe the structure of compound 1436 as well as processes for synthesizing and isolating the compound. For example, as described in these applications, compound 1436 can be prepared from a squalamine starting material.

When squalamine is isolated from dogfish shark liver, the sulfate group is located at the C-24 position, and there is no difficulty in providing the sulfate group at this location in a stereoselective manner. Likewise, when compound 1436 is derived from a squalamine starting material, the sulfate group already is located at the C-24 position, and therefore, there is no difficulty in obtaining a stereoselective structure at the C-24 position.

Difficulties have been encountered, however, when attempting to provide a process for synthesizing squalamine or compound 1436 from commercially available starting materials (i.e., not from shark liver isolates). These difficulties include low overall yields of the desired steroid product, because many steps are involved in the synthesis process. Additional difficulties are encountered in providing a sulfate group at the C-24 position. Particularly, it is difficult to provide the sulfate group at the C-24 position in a highly stereoselective orientation. See, for example, Pechulis, et al., "Synthesis of 24ξ-Squalamine, an Anti-Infective Steroidal Polyamine," *J. Org. Chem.*, 1995, Vol. 60, pp. 5121–5126; and Moriarty, et al., "Synthesis of Squalamine. A Steroidal Antibiotic from the Shark," *Tetrahedron Letters*, Vol. 35, No. 44, (1994), pp. 8103–8106. These articles each are entirely incorporated herein by reference. This invention seeks to overcome those difficulties in synthesizing squalamine and compound 1436.

Squalamine and compound 1436 are not the only compounds of interest that include a specified substituent, in a stereospecific orientation, at the C-24 position. For example, the above-noted patent applications describe many different aminosterol compounds that have various C-24 substituents. As another steroid example, cerebrosterol, includes a hydroxyl group in an S-orientation at the C-24 position. MC 903, a 1, 24-dihydroxyvitamin D analogue, also includes a hydroxyl group in an S-orientation at the 24 position. 1α, 24(R)-dihydroxyvitamin $D_3$ includes a hydroxyl group in an R-orientation at the 24 position. The chemical structures for cerebrosterol, MC 903 and 1α, 24(R)-dihydroxyvitamin $D_3$ are shown in FIGS. 3A, 3B and 3C, respectively.

Because of the importance of squalamine, compound 1436, other aminosterols, 24R and 24S-hydroxylated steroids and vitamin-$D_3$ metabolites, there has been considerable interest in preparing compounds with a single stereospecific orientation at the C-24 position. Processes for producing squalamine and compound 1436 are described in the patent documents noted above. These processes, while effective in producing squalamine and compound 1436, do not enable large scale production of the desired aminosterol materials because relatively low yields are realized by these processes.

Other researchers have developed processes for stereoselectively producing cerebrosterol, MC 903, and 1α, 24(R)-dihydroxyvitamin $D_3$. A process for producing cerebrosterol is described in Koch, et al., "A Stereoselective Synthesis and a Convenient Synthesis of Optically Pure (24R)- and (24S)-

24 hydroxycholesterols," *Bulletin de la Société Chimique de France*, 1983, (No. 7–8), Vol. II, pp. 189–194. A process for producing MC 903 is described in Calverley, "Synthesis of MC 903, a Biologically Active Vitamin D Metabolite Analogue," *Tetrahedron*, 1987, Vol. 43, No. 20, pp. 4609–4619. A process for producing 1α, 24(R)-dihydroxyvitamin $D_3$ is described in Okamoto, et al. "Asymmetric Isopropylation of Steroidal 24-Aldehydes for the Synthesis of 24(R)-Hydroxycholesterol, *Tetrahedron: Asymmetry*, 1995, Vol. 6, No. 3, pp. 767–778. These articles each are entirely incorporated by reference.

One approach, as described in the above-noted articles, has been to reduce a 22-ene-24-one system in a stereoselective manner. This scheme is illustrated in FIG. 4A. The 22-ene- 24-one system (material B from FIG. 4A) can be produced in a single step from the corresponding 22-aldehyde (material A) using an appropriate Wittig reagent (prepared in 2 steps). Therefore, if this reduction procedure was stereoselective, this would be a convenient two step procedure for preparing chiral C-24 alcohols (material C).

Unfortunately, this reaction is not stereospecific. Calverley described attempts to reduce a vitamin-$D_3$-22-ene-24-one with sodium borohydride and cerium (III) chloride; however, he achieved only a 38:61 ratio of the desired 24S product to the undesired 24R allylic alcohol. In the process of Calverley, the product had to be purified by chromatography and recrystallization to separate the 24R product from the desired 24S product. The 24S and 24R allylic alcohols can be very difficult to separate. Thus, this chemical process is not suitable for use on a large scale.

Koch, using a similar scheme to that described above, did not fare much better in producing a stereospecific 24S product. In producing cerebrosterol, Koch demonstrated that lithium aluminum hydride, even substituted with chiral compounds, reduced a cholest-22-ene-24-one system B (FIG. 4A) in a ratio of 1:2 (24S to 24R allylic alcohols C).

Using a different reaction scheme, as illustrated in FIG. 4B, Koch also showed that the reduction of a cholest-22-yne-24-one system (material D), followed by partial reduction of the triple bond, gave only modest selectivity for the 24S stereoisomer, using a lithium aluminum hydride reducing reagent. A 2:1 ratio of 24S to 24R allylic alcohols C was obtained in this reaction scheme.

There has been one successful reduction of a related 25-ene-24-one system using Noyori's 2,2'-dihydroxy-1,1'-binaphthyl lithium aluminum hydride reagent at –90° C. to give 95:5 selectivity for the 24R-alcohol. The procedure is described in Ishiguro, et al. "Stereoselective Introduction of Hydroxy-Groups into the 24-, 25-, and 26-Positions of the Cholesterol Side Chain," *J. C. S. Chem. Comm.*, 1981, pp. 115–117, which article is entirely incorporated herein by reference. The 25-ene-24-one intermediate material (producible in four steps) is less readily accessible than the 22-ene-24-one system (producible in one step). This factor decreases the desirability of this route. Additionally, the low temperature required for the chiral reduction also detracts from the commercial practicality of this method.

One lengthy approach has been to alkylate a C-22 sulfone with a chiral epoxide. Because of the poor selectivity obtained from chiral reductions of material B shown above (FIG. 4A), Koch found this six step procedure from the 22-aldehyde preferable, using a reagent based on valine (producible in four steps). Overall, 10 steps were required by this process to do what one could do in four steps, if a stereoselective reduction technique was available.

Finally, Okamoto successfully used chiral β-amino alcohol catalyzed addition of diisopropylzinc to steroidal 24-aldehydes to provide 24R-hydroxycholesterols in good yields with high diastereoselectivities (97:3). Again, however, overall, more steps are required to yield the desired pure alcohol.

SUMMARY OF THE INVENTION

It is an object of this invention to overcome the various problems and disadvantages described above. The process of the invention stereoselectively reduces an unsaturated alkyl ketone substituent. The alkyl ketone is attached to a fused ring base, such as a steroid ring base or a vitamin $D_3$ analog ring base. In the process of the invention, the unsaturated alkyl ketone reacts with a chiral oxazaborolidine reagent to stereoselectively reduce the unsaturated alkyl ketone to an unsaturated alkyl alcohol. The unsaturated alkyl alcohol can be furter reduced to produce a saturated alkyl alcohol.

In the invention, the chiral oxazaborolidine reagent is preferably at least one member selected from the group of compounds illustrated in FIGS. 13A through 13D (compounds 11, 12, 13, and 14). These illustrated compounds, borane complexes of Me-CBS and Bu-CBS, will be described below. "CBS" stands for "Corey-Bakshi-Shibata" reagents, which will be described in more detail below.

One group of starting materials on which the process of this invention can be used are compounds that include an alkeneone substituent attached to a fused ring base. A specific example is a compound having a 22-ene-24-one substituent on a steroid ring base. In this instance, the alkeneone material reacts with an appropriate chiral oxazaborolidine reagent to stereoselectively reduce the alkeneone to an allylic alcohol. The allylic alcohol can be further reduced to provide a hydroxylated, saturated alkane side chain from the fused ring base.

For this embodiment of the invention, the alkeneone substituent can be produced in any suitable manner. For example, the 22-ene-24-one alkeneone material mentioned above can be produced by reacting a C-22 aldehyde substituent (on a steroid ring base) with a Wittig reagent.

A second group of compounds on which the process of this invention can be used are alkyneone compounds, such as compounds including a 22-yne-24-one substituent on a steroid ring base. In this method, the alkyneone reacts with a chiral oxazaborolidine reagent to stereoselectively reduce the alkyneone to a propargyllic alcohol. If desired, in this method, the propargyllic alcohol can be further reduced to a hydroxylated, saturated alkane.

The 22-yne-24-one starting material in this embodiment of the invention can be produced from a C-22 aldehyde on a steroid ring base. This aldehyde starting material first reacts to produce a 22-alkyne substituent on the steroid ring base, and then the 22-alkyne substituent reacts with a lithium containing reagent and anhydride to produce the 22-yne-24-one substituent on the steroid ring base.

Preferably, the process of the invention produces at least 90% of the desired isomer. Selectivity of greater than 95% is particularly preferred, and greater than 97% is most advantageous. Greater than 97% of the desired isomer corresponds to greater than 94% "de" (diastereomeric excess, which is calculated as 97%–3%=94%).

The invention also relates to various intermediates that are produced in the process of the invention. These intermediates are particularly useful in producing squalamine, compound 1436, or other desired aminosterols.

BRIEF DESCRIPTION OF THE DRAWINGS

Advantageous aspects of the invention will be evident from the following detailed description which should be considered in conjunction with the attached drawings, wherein.

DETAILED DESCRIPTION OF THE INVENTION

As described above, there is a need in the art for a stereoselective process for synthesizing compounds having a 24-hydroxylated steroid or vitamin D analog structure. The stereospecific 24-hydroxylated compound can itself be the desired final compound (e.g., in producing cerebrosterol, MC 903, or 1α, 24(R)-dihydroxyvitamin $D_3$). Alternatively, the process of the invention can be used to make a hydroxylated intermediate composition that can be further modified to produce the desired final product. For example, the process according to the invention can be used to produce stereospecific intermediates that can be further modified to synthesize squalamine, compound 1436, other useful aminosterols, or steroids. Such compounds include stereospecific groups (e.g., sulfate groups in an R orientation for squalamine and compound 1436) at the 24 position.

The method according to the invention includes processes for stereoselectively reducing cholest-22-ene-24-one and cholest-22-yne-24-one systems. In one process of the invention, Corey's (R)-methyl oxazaborolidine reagent reacts with a cholest-22-ene-24-one material to produce the desired 24S-allylic alcohol in good yield and high stereoselectivity (>98:2). This reaction scheme is scalable to kilogram quantities because of the moderate temperature used (−20° C.) and because of the reasonable cost of the chiral oxazaborolidine reagent. The cholest-22-ene-24-one material is easily prepared from the 22-aldehyde material, in high yield, without the need for a chromatography step. Accordingly, the method according to the invention is very practical in that it provides the chiral alcohol in a few number of steps (two), with procedures that are easily scalable to large quantities.

In an alternative method according to the invention, the cholest-22-yne-24-one system is reduced stereoselectively with an (S)methyl oxazaborolidine borane complex. The cholest-22-yne-24-one material (an acetylenic ketone) can be prepared from an aldehyde material in two convenient steps, thereby making this a commercially practical method. Other non-steroidal propargyl ketones have been reduced selectively using this reagent, as described in Parker, K. A. et al. "Asymmetric Reduction. A Convenient Method for the Reduction of Alkynyl Ketones," *J. Org. Chem.*, 1996, Vol. 61, pp. 3214–3217. This article is entirely incorporated herein by reference.

The methods according to the invention will be described generally below, in conjunction with FIGS. 5–9. The process of the invention can be used to make any material having the general fused ring base structure shown as compound C in FIG. 5 (e.g., any compound having a six carbon ring that shares two carbon atoms with an attached five carbon ring).

Figure 5:
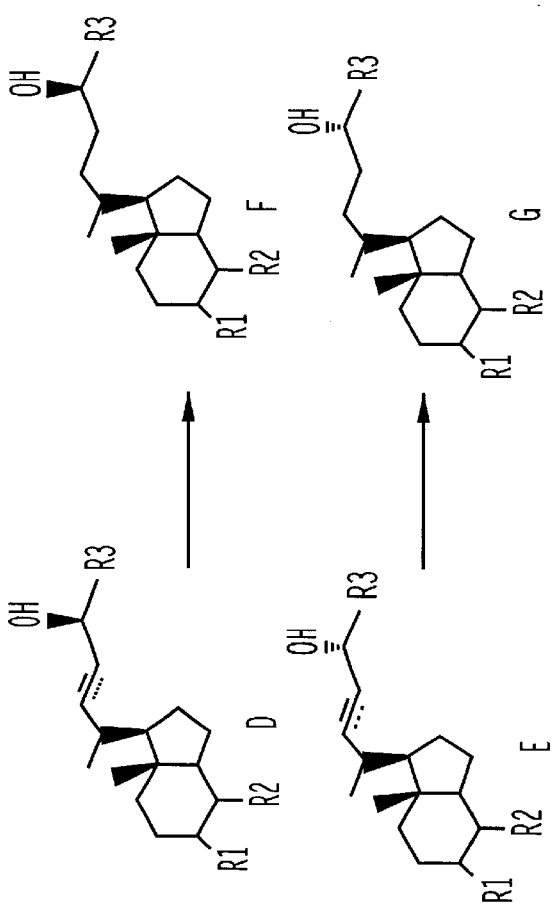
FIG. 5 illustrates reaction mechanisms generally showing the process of the invention.

Generally, the process according to the invention relates to a method for stereoselectively reducing an unsaturated alkyl ketone substituent attached to a fused ring base. The method is generally illustrated in FIG. 5. In this method, the starting material is an unsaturated alkyl ketone C, attached to a fused ring base. The unsaturated bond between the 22 and 23 carbons can be a double bond or a triple bond. This is illustrated in FIG. 5 using a dashed line for the triple bond.

Figure 6B:
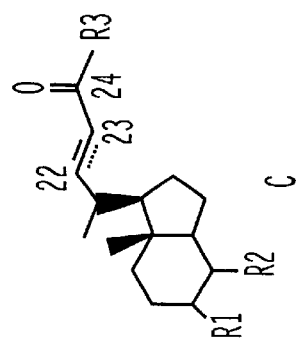
FIG. 6B shows a second substituent group that can be included on the fused ring starting material in the process of the invention.
Figure 6B:
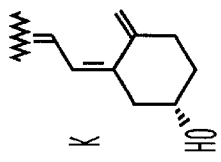
Figure 6A:
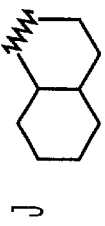
FIG. 6A shows a first substituent group that can be included on the fused ring starting material in the process of the invention.

The fused ring, as shown in FIG. 5, may have substituent groups R1, R2, and R3. In the illustrated formula, R1 and R2 together can be, for example, two fused six membered rings J, forming a steroid fused ring base, as shown in FIG. 6A. This steroid ring base can include appropriate substituent groups (e.g., alkyl groups, hydroxyl groups, amine chains, etc.) or unsaturations. As another alternative, R1 can be a hydrogen atom and R2 can be a vitamin $D_3$ fragment K as shown in FIG. 6B. This vitamin $D_3$ base also can include any appropriate substituent groups. R3, as shown in FIG. 5, can be any suitable substituent, such as a $C_1$ to $C_7$ alkyl group, straight chain, branched, aryl or formed into a ring. The R3 group can include any suitable substituent group, so long as the substituent group does not substantially compete or interfere with the desired reactions.

In accordance with the process of the invention, the unsaturated alkyl ketone starting material reacts with a chiral oxazaborolidine reagent to stereoselectively reduce the unsaturated alkyl ketone to an unsaturated alcohol D or E. The selection of a particular oxazaborolidine reagent will determine the stereoselective orientation of the final product. If a chiral oxazaborolidine reagent having one stereospecific orientation is used, then the reaction mechanism shown at the top in FIG. 5 will be followed. If a chiral oxazaborolidine reagent is selected having the opposite stereospecific orientation, then the reaction mechanism shown at the bottom of FIG. 5 will be followed. Examples of suitable oxazaborolidine reagents include the borane complexes of (S)-MeCBS, (S)-BuCBS, (R)MeCBS, or (R)-BuCBS (see FIGS. 13A to 13D). These reagents are described in more detail below.

The intermediate unsaturated alcohol materials D and E are produced with a stereospecific orientation. The unsaturated bond in the alkyl chain can be further reduced in the process of the invention, if desired, to produce a saturated alkyl alcohol F or G, as shown in FIG. 5. If this saturated alcohol product is not the desired final product, it can be used as a convenient, stereospecific intermediate to produce the desired final product.

Figure 7:
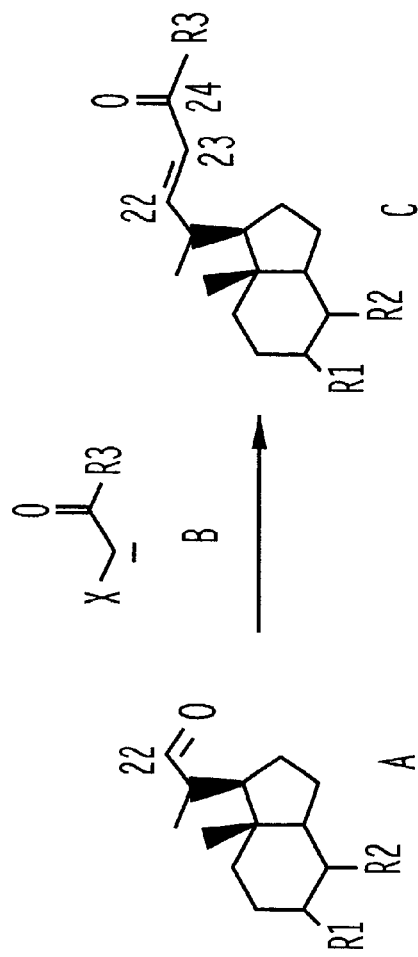
FIG. 7 illustrates a reaction scheme for producing an alkeneone from an aldehyde in the process of the invention.

A more specific reaction scheme for obtaining material F in FIG. 5 now will be described. First, the starting material C must be produced, and in this reaction scheme, material C will be an alkeneone material. The alkeneone material C can be produced from an aldehyde substituent on the fused ring base. As shown in FIG. 7, the aldehyde substituent (material A) reacts with a Wittig reagent B to produce the alkeneone material C. R1, R2, and R3 in FIG. 7 have the same definitions as those described above in connection with FIGS. 5, 6A, and 6B. The substituent X on the Wittig reagent in FIG. 7 can stand for a $Ph_3P$-group, an $(EtO)_2PO$-group, or an $(R4O)_2PO$-group, wherein R4 is an alkyl chain having 1–7 carbons, straight chain, branched, cyclic, or aryl.

Figure 13A:
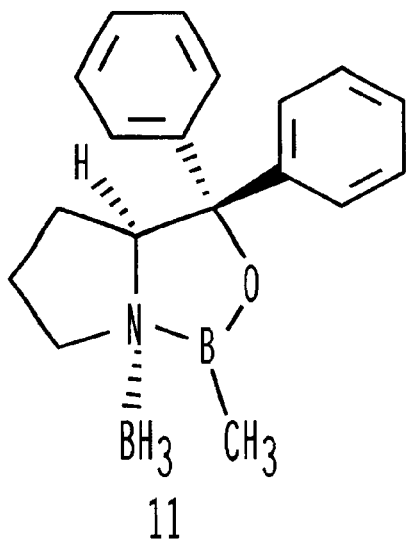
FIGS. 13A and 13B are oxazaborolidine-borane complexes used to produce R-allylic alcohols from enones.
Figure 13B:
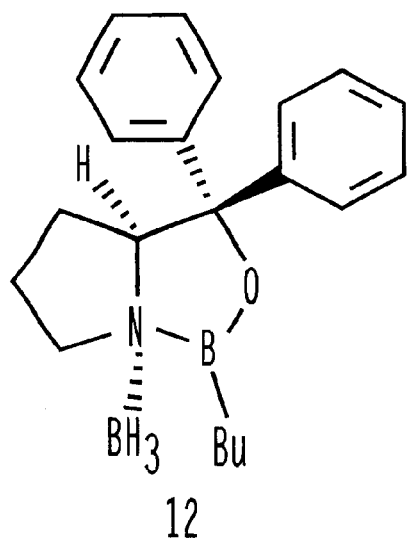
Figure 13C:
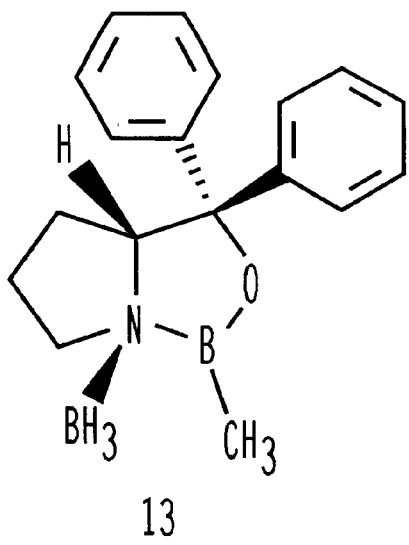
FIGS. 13C and 13D are oxazaborolidine-borane complexes used to produce S-allylic alcohols from enones.
Figure 13D:
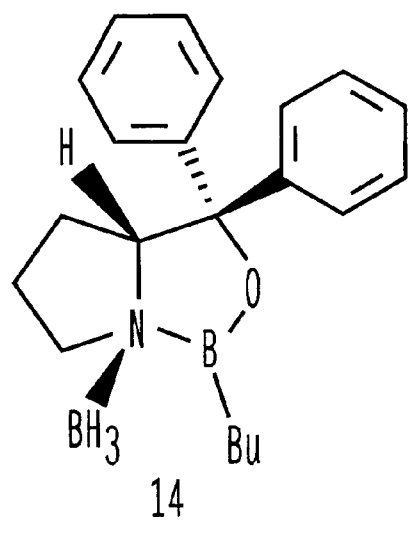

The alkeneone material C reacts with the borane complex of (R)-MeCBS (13) and (R)-BuCBS (14) to stereoselectively reduce the alkeneone C to an allylic alcohol D. See the upper reaction mechanism in FIG. 5. (R)-MeCBS (13) and (R)-BuCBS (14) are borane complexes of oxazaborolidine reagents, the structures of which are illustrated in FIGS. 13C and 13D, respectively. These reagents, without the borane complex ($BH_3$), are commercially available from Callery. The preparation of the borane complexes of the oxazaborolidine reagents is described in more detail below. Finally, as shown in FIG. 5, the allylic alcohol D is further reduced to eliminate the unsaturation bond and produce a hydroxylated, saturated alkane F.

Figure 8:
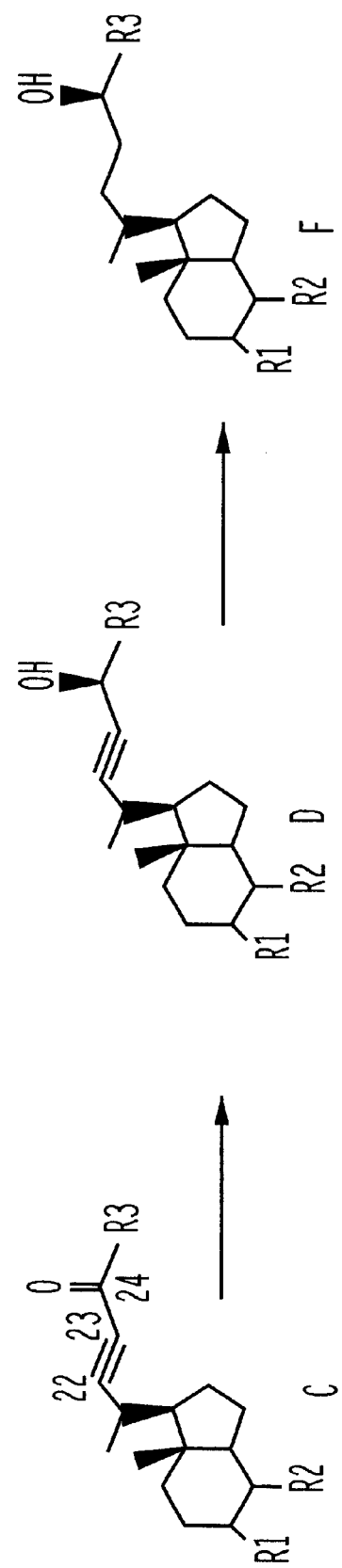
FIG. 8 illustrates a reaction scheme for converting an alkyneone starting material to a saturated alcohol in a stereoselective orientation in the process of the invention.
Figure 9:
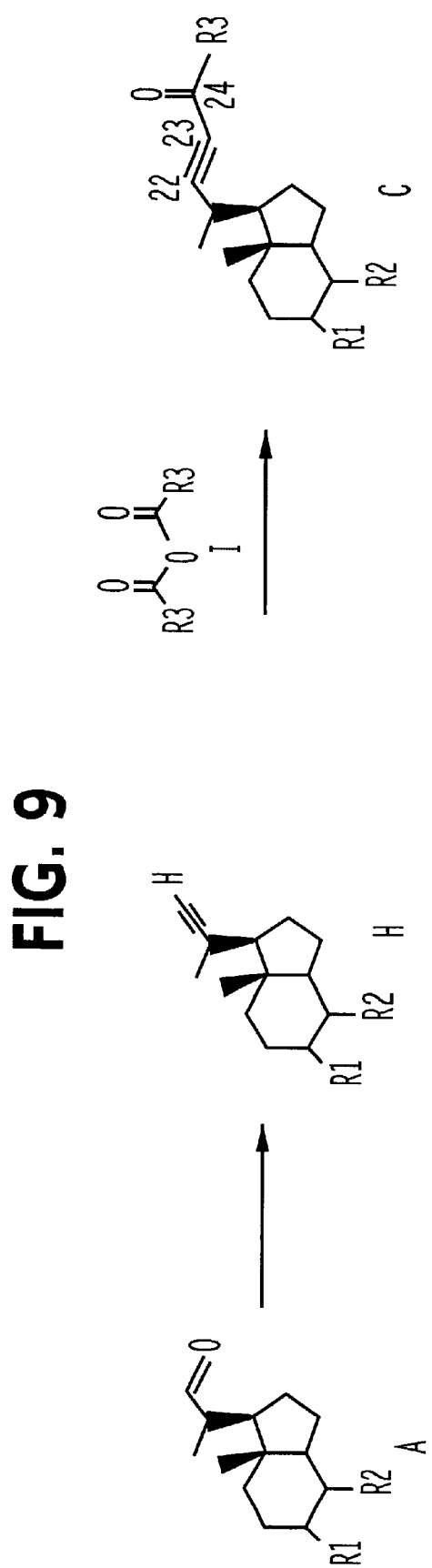
FIG. 9 illustrates a reaction scheme for producing the alkyneone starting material used in the process shown in FIG. 8.

An alternative mechanism for producing the saturated alkane F is described in conjunction with FIGS. 8 and 9. In this instance, alkane F is produced through an alkyneone starting material C. The alkyneone starting material C first must be produced. As shown in FIG. 9, alkyneone material C also can be produced from an aldehyde starting material A. In a first reaction step, the aldehyde substituent on starting material A reacts to produce an alkyne alkyl substituent (material H) on the fused ring base. Thereafter, the alkyne H reacts with a lithium containing reagent and anhydride I to produce an alkyneone C on the fused ring base. In FIG. 9, R1, R2, and R3 have the same definitions as those described above.

Once produced, the alkyneone material C reacts with the borane complexes of (S)-MeCBS (11) or (S)-BuCBS (12) to stereoselectively reduce the alkyneone to a propargyllic alcohol D. See FIG. 8. (S)-MeCBS (11) and (S)-BuCBS (12) are borane complexes of oxazaborolidine reagents, the structure of which are illustrated in FIGS. 13A and 13B, respectively. These reagents, without the borane complex, are commercially available from Callery. The preparation of the borane complexes of the oxazaborolidine reagents is described in more detail below. Finally, the propargyllic alcohol D is further reduced to eliminate the unsaturation and produce a hydroxylated, saturated alkane F.

Once the hydroxyl group is provided at the C-24 position, as shown in FIGS. 5 and 8, any suitable functional group can be attached to the steroid via the oxygen at the hydroxyl. For instance, an acetate group, a benzoate group, a TMS-O-group, or a phosphate group can be attached at the C-24 position in a stereospecific manner.

The process according to the invention now will be described in more specific terms in a process for producing specific steroid chemicals. These specific examples should be construed as illustrating the invention, and not as limiting the same.

I. EXAMPLE—PRODUCTION OF COMPOUNDS HAVING A C-24 ALCOHOL SUBSTITUENT (COMPOUND 1436 AND SQUALAMINE)

A. Production of Test Materials and Standards

Squalamine is a steroid that contains a sulfated 24R-alcohol, as described in R. M. Moriarty, et al. "Stereoselective Synthesis of Squalamine Dessulfate," *Tetrahedron Letters*, 1995, Vol. 36, No. 29, pp. 5139–5142. This article is entirely incorporated herein by reference. Squalamine is a member of a class of natural aminosterols from the shark that has clinical potential as an anti-infective (note K. S. Moore, et al. "Squalamine: An Aminosterol Antibiotic from the Shark," *Proc. Natl. Acad. Sci. USA*, 1993, Vol. 90, 1354–1358) and an anti-angiogenic agent (note H. Brem, et al, American Association of Neurological Surgeons, Apr. 30–May 4, 1996, Minneapolis, Minn.). The Moore article also is entirely incorporated herein by reference. Squalamine contains a cholestane ring system with 5α-hydrido, 7α-hydroxyl, 3β-spermidinyl, and 24R-sulfate groups. Compound 1436 is similar in structure to squalamine, but it has a 3β-spermine substituent instead of the 3β-spermidinyl substituent.

Figure 11A:
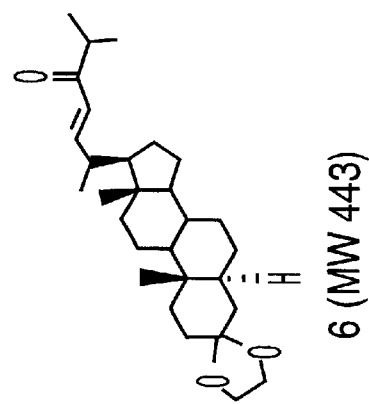
FIG. 11A illustrates the chemical structure of an intermediate used in making stereoselective 24-hydroxylated steroids.
Figure 11B:
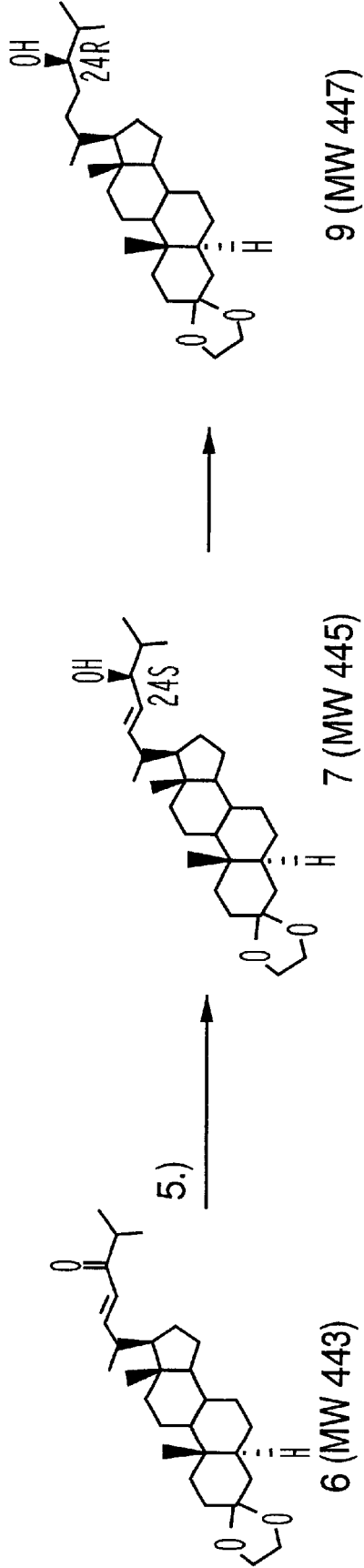
FIG. 11B illustrates a reaction mechanism for producing stereoselective 24-hydroxylated steroids using the intermediate of FIG. 11A.

Initially, it was desired to prepare a model system including compound 6, as shown in FIG. 11A. This model system of compound 6 was desired because compound 6 contains many of the features required to synthesize squalamine and compound 1436, but it lacks the 7-hydroxyl group. Note the general correspondence between compound 6 and general compound C illustrated in FIGS. 5, 7, 8, and 9. Compound 6 would be used to synthesize the 24S-allylic alcohol shown as compound 7, which would then be reduced to produce the desired 24R-alcohol, shown as compound 9. This general reaction scheme is illustrated in FIG. 11B. Note that the 22–23 double bond changes the priority of the groups in determining R from S in the nomenclature rules.

Figure 12:
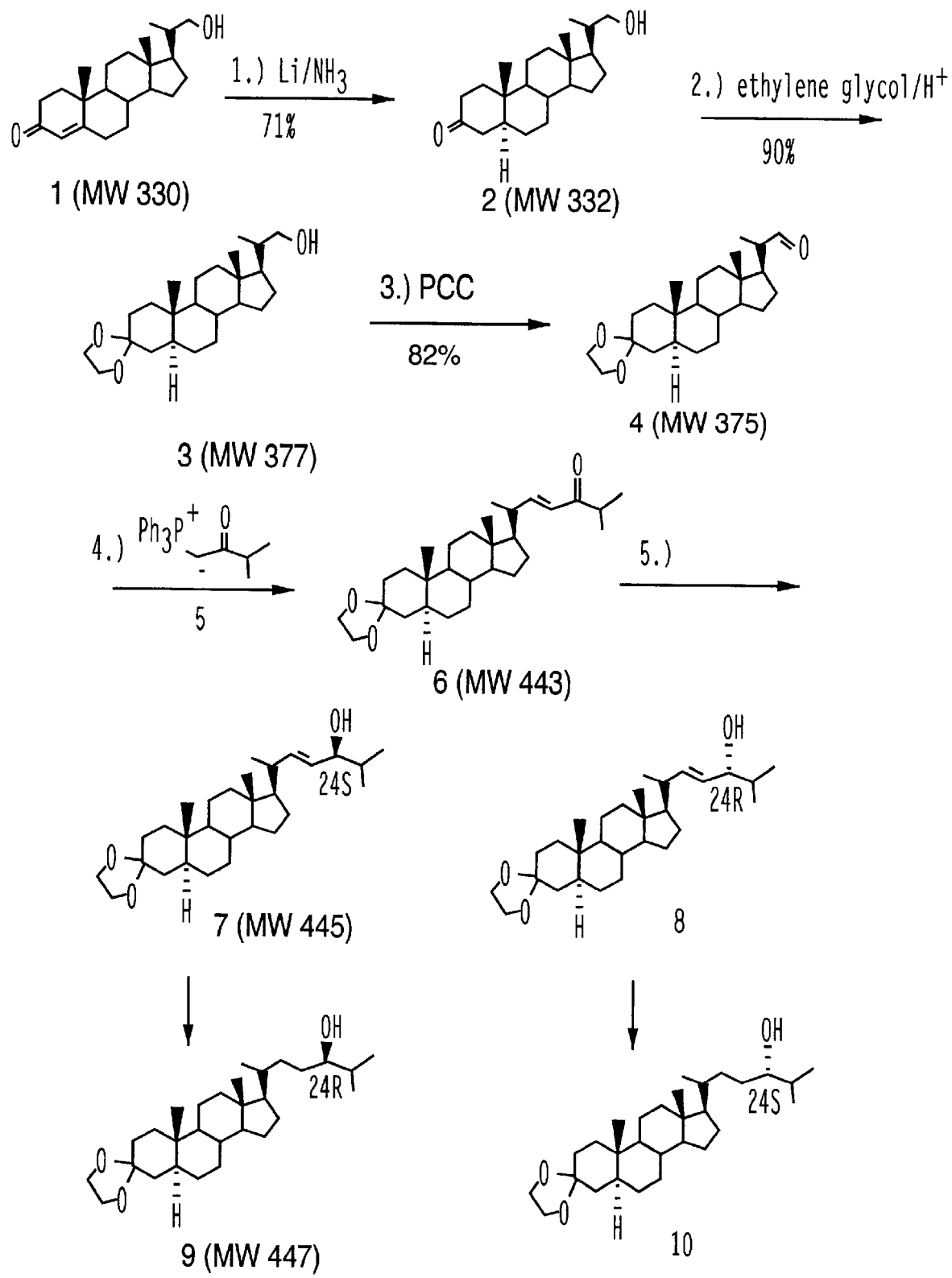
FIG. 12 illustrates a reaction mechanism for producing the intermediate of FIG. 11A as well as stereoselective 24-hydroxylated steroids.

FIG. 12 generally illustrates the overall reaction process for producing compound 6, and from compound 6, producing compounds 9 and 10, the standard samples. To avoid obscuring the process, details of each reaction step are not included in this portion of the application text. These reaction steps are described in more detail below in the "Experimental Section" of this application.

Initially, steroid 1 (commercially available from Pharmacia or Upjohn) was reduced with lithium in ammonia to produce material 2. Notably, material 2 has the trans-AB-ring junction that is contained in squalamine. The carbonyl group at the C-3 position then was protected by converting it to an ethylene ketal, thereby producing material 3. Material 3 was oxidized using pyridinium chlorochromate to produce the aldehyde material 4.

In the next reaction step, material 4 was reacted with a Wittig reagent 5 to produce material 6. This Wittig reagent 5 can be prepared in the manner described in the Experimental Section of this application. During this reaction, the cholest-22-ene-24-one side chain of substrate 6 was introduced in a single step from the C-22 aldehyde 4 via reaction with the Wittig reagent 5. Material 6 was produced in good yield by this reaction procedure.

After material 6 was produced, this material was reduced to produce the alcohol products. Initially, two alcohol products 9 and 10 were prepared so that they could be compared by $^{13}$C NMR spectroscopy. It is known that the NMR signal due to C-24 including an R-alcohol is 0.4 ppm upfield from that of the corresponding S-alcohol (with a saturated side chain). See N. Koizumi, et al., "Carbon-13 Nuclear Magnetic Resonance of 24-Substituted Steroids," Chem. Pharm. Bull., 1979, Vol. 27, No. 1, pp. 38–42, which document is entirely incorporated herein by reference.

Alcohols 9 and 10 were produced as follows. Compound 6 was reduced with lithium aluminum hydride to produce a mixture of allylic alcohols 7 and 8. The desired 24-S allylic alcohol (7) is produced if the hydride attacked material 6 from the alpha-face. The less polar compound (alcohol 8) was separated and then reduced with hydrogen (Pd/C). A mixture of compounds 7 and 8 was also reduced for comparison, because pure compound 7 could not be separated from the mixture of compounds 7 and 8. It was found that the less polar allylic alcohol 8 (faster moving on silica gel thin layer chromatography ("TLC") plates) yielded the undesired 24S alcohol 10, as evidenced by a resonance at 77.66 ppm in the $^{13}$C NMR spectrum. The mixture of 7 and 8 was reduced to produce saturated alcohols 9 and 10, with resonances at 77.31 and 77.66. From these tests, applicants determined that the more polar allylic alcohol 7 must have the 24S-stereochemistry, and compound 9 must have the desired 24R-stereochemistry.

The reaction with compound 6 was similar to that described in a paper by Shen Zheng-Wu and Zhou Wei-Shan, "Study on the Syntheses of Brassinolide and Related Compounds. Part 14. Highly Stereoselective Construction of the Side-Chain of Brassinosteroids Utilizing the β-Alkylative 1,3-Carbonyl Transposition of the Steroidal 22-En-24-one," J. Chem. Soc. Perkin Trans., 1990, Vol. 1, pp. 1765–1767. This article is entirely incorporated herein by reference. Zheng-Wu and Wei-Shan described that methyl lithium addition to a cholestane-22-ene-24-one system was achieved selectively from the alpha-face.

B. Selective Production of Compounds 7 and 9

1. Using Corey-Bakshi-Shibata Reagents ("CBS reagents")

In one method according to the invention, compound 6 is stereoselectively reduced to compound 7 using Corey-Bakshi-Shibata type reagents ("CBS reagents"). E. J. Corey described reducing non-steroidal α,β-unsaturated ketones with oxazaborolidine-borane complexes 11 and 12 (see FIGS. 13A and 13B, respectively, for the chemical structure of complexes 11 and 12) to selectively yield the R-allylic alcohols. See E. J. Corey, et al., "A New System for Catalytic Enantioselective Reduction of Achiral Ketones to Chiral Alcohols. Synthesis of Chiral α-Hydroxy Acids," Tetrahedron Letters, 1990, Vol. 31, No. 5, pp. 611–614 and U.S. Pat. No. 4,943,635 dated Jul. 24, 1990. These Corey documents each are entirely incorporated herein by reference. Corey further described the use of the opposite catalysts 13 and 14 (see FIGS. 13C and 13D, respectively) to yield the S-allylic alcohols. See E. J. Corey, et al., "Total Synthesis of (±)-Forskolin," Journal of the American Chemical Society, 1988, Vol. 110, pp. 3672–3673. This document also is entirely incorporated herein by reference.

Suitable oxazaborolidines, such as (R)-MeCBS and (S)-MeCBS, are commercially available from Callery. These reagents are combined with borane to form the complexes shown in FIGS. 13C and 13A. (R)-MeCBS is the compound of FIG. 13C without the BH$_3$ group. The production of the borane complex is described in more detail below, in the Experimental Section.

In view of the information of Corey, compound 6 was reduced with reagents 13 and 14 to produce the desired S-allylic alcohol 7. A series of reductions were attempted on compound 6, and the results are shown in the following Table.

TABLE

Reduction of Compound 6 with (R)-(X)-CBS at −20° C. in Toluene

| Entry | Catalyst (mol %) | BH$_3$—THF (eq.) | Addition time (hr) | Reaction time (hr) | de (%)* | Isolated yield (%) |
|---|---|---|---|---|---|---|
| 1 | Me-CBS (20) | 1 | 1.5 | 21 | 40 | |
| 2 | Bu-CBS (20) | 2 | 1.5 | 3 | 0 | |
| 3 | Me-CBS (20) | 1 + 1 + 0.5 | 1.5 | 22 | | |
| 4 | Me-CBS (20) | 2.5 | 2.3 | 22 | 30–35 | |
| 5 | Me-CBS (50) | 2.5 | 2.3 | 2 | 80 | 56 |
| 6 | Me-CBS (100) | 1.5 | 2.5 | 22 | 40 | |
| 7 | Me-CBS (100) | 2.5 | 1.75 | 3 | 94–98 | 71 |

*diastereomeric excess, estimated by calibrated TLC on crude products

As demonstrated by this Table, a wide range of selectivities were produced in this reaction. The selectivities ranged from poor (entries 1–4, 6), to good (entry 5), to excellent (entry 7). The optimum conditions shown in the Table involved the use of stoichiometric quantities of (R)-Me-CBS with 2.5 equivalents of borane (from borated tetrahydrofuran ("BH$_3$-THF")), which provided a good yield (71%) and excellent selectivity (94–98% de by quantitative TLC) for compound 7. The initial experiment was done with purification by column chromatography. Later experiments demonstrated that this reaction could be accomplished without cromatography in high yield (90%) to produce only compound 7 within the detection limits of $^{13}$C NMR (>95%). Compound 7 was reduced with hydrogen to produce the saturated alcohol compound 9, which had a carbon resonance of 77.29 ppm, confirming the earlier assignment (upfield approximately 0.4 ppm from compound 10, located at 77.66 ppm).

2. Using (S)-methyl oxazaborolidine

As an alternative method according to the invention, stereoselective reduction of the 22-yne-24-one system (see FIG. 8) with Corey's (S)-methyl oxazaborolidine reagent also was successful in introducing the chiral hydroxy group at the C-24 position. The substrate for the reduction, propargyl ketone 16, was prepared from aldehyde 4 in two steps, in the manner shown in FIG. 14. As noted above, the process steps will be set forth in more detail in the "Experimental Section" of this application.

Figure 14:
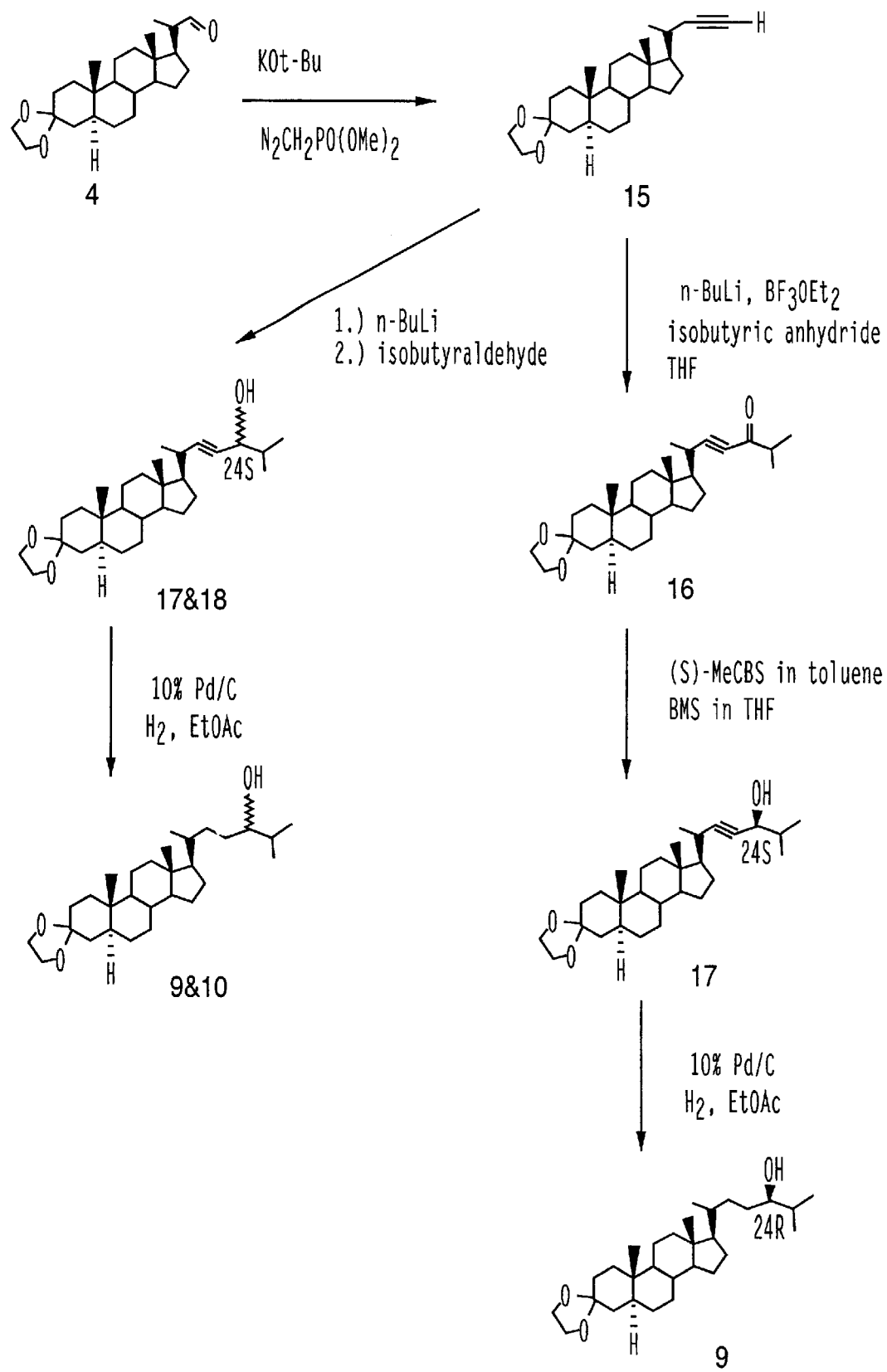
FIG. 14 illustrates a reaction mechanism for producing a specific stereospecific 24-hydroxylated steroid.

In this alternative process, aldehyde 4 was homologated to the terminal alkyne 15 in a 97% yield with Seyferth's diazophosphonate reagent. See Seyferth, et al., "Some Reactions of Dimethylphosphono-Substituted Diazoalkanes, $(MeO)_2P(0)$ CR Transfer to Olefins and 1,3-Dipolar Additions of $(MeO)_2P(0)$ $C(N_2)R^1$," *J. Org. Chem.*, 1971, Vol. 36, pp. 1379–1386 (this article is entirely incorporated herein by reference). The reaction was carried out using the methodology developed by Colvin and Gilbert. See Colvin, et al., "A Simple Procedure for the Elaboration of Carbonyl Compounds into Homologous Alkynes," *J. Chem Soc., Perkin Trans. I*, 1977, pp. 869–874, and Gilbert, et al., "Elaboration of Aldehydes and Ketones to Alkynes: Improved Methodology," *J. Org. Chem.*, 1979, Vol. 44, No. 26, pp. 4997–4998, which articles each are entirely incorporated herein by reference. One portion of the terminal alkyne 15 was converted to the lithium alkynyltrifluoro borate and reacted with isobutyric anhydride to produce the propargyl ketone 16 (note the discussion in Brown et al., "Improved Highly Efficient Synthesis of α,β-Acetylenic Ketones. Nature of the Intermediate from the Reaction of Lithium Acetylide with Boron Trifluoride Etherate," *Tetrahedron Letters*, 1984, Vol. 25, No. 23, pp. 2411–2414, which article is entirely incorporated herein by reference). The stereoselective reduction of the propargyl ketone 16 was carried out using two equivalents of (S)-methyl CBS oxazaborolidine reagent and boron methyl sulfide ("BMS") in tetrahydrofuran at −30° C. (see Parker, K. A. and Ledeboer, M. R., "Asymmetric Reduction. A Convenient Method for the Reduction of Alkynyl Ketones," *J. Org. Chem.*, 1996, Vol. 61, pp. 3214–3217, which article is entirely incorporated herein by reference) to produce propargyl alcohol 17. The propargyl alcohol 17 was hydrogenated to alcohol 9, as shown in FIG. 14.

For comparison purposes, an epimeric mixture of propargyl alcohols 17 and 18 was prepared by treating a second portion of compound 15 with n-BuLi, followed by addition of isobutyraldehyde. The propargyl alcohols 17 and 18 were hydrogenated to give a mixture of alcohols 9 and 10. $^{13}C$ NMR spectra of alcohols 9 and 10 produced two resonances of equal intensities at 77.29 and 77.63 ppm for the C-24 carbon (i.e., for the R and S stereochemistries, respectively).

The $^{13}C$ NMR spectra of the alcohol 9 (prepared via compounds 16 and 17 in FIG. 14) was compared to the $^{13}C$ NMR spectra of the epimeric mixture of alcohols 9 and 10. The $^{13}C$ NMR spectra of the hydrogenated product of compound 17 showed a single signal for the C-24 carbon at 77.29 ppm corresponding to the 24 (R) stereochemistry. This confirmed that compound 9 was produced from compounds 4, 15, 16, and 17 in a stereospecific manner.

C. Production of Steroids Including a 7α-Hydroxyl Group

1. Using Steroid 21 as a Starting Material

With these positive results in hand relating to the selective production of a 24(R)-hydroxyl group, applicants sought a process for the synthesis of compound 32 (see FIG. 15B), which can be used to produce a steroid having a 7α-hydroxyl group, as is present in squalamine and compound 1436. This intermediate (compound 32) can be used in preparing squalamine and compound 1436. As mentioned above, a more detailed description of the production of the various compounds and intermediates is provided in the "Experimental Section" of this patent application.

Figure 15A:
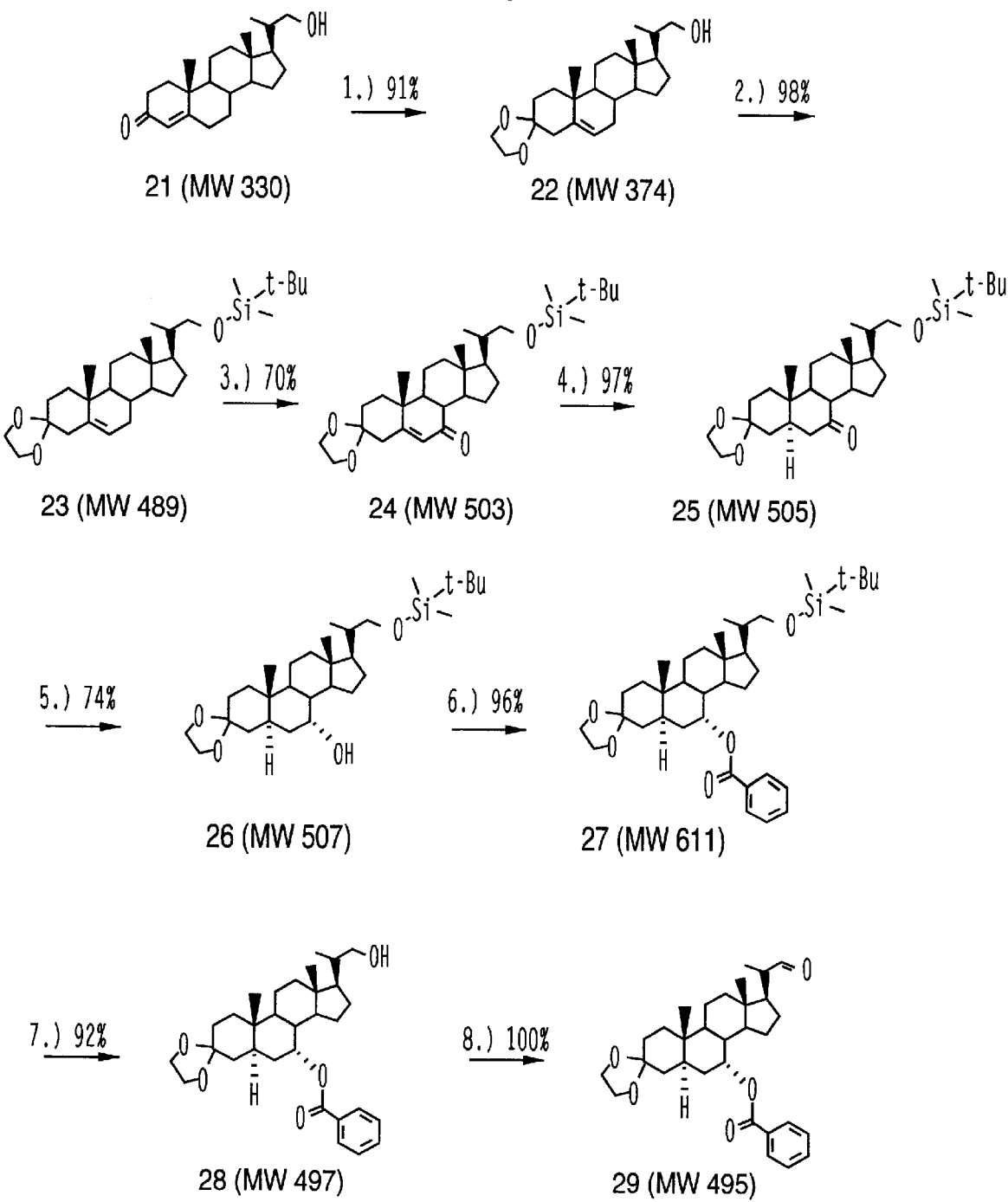
FIG. 15A illustrates a reaction mechanism for producing steroid 29, which can be used for producing squalamine and compound 1436.
Figure 15B:
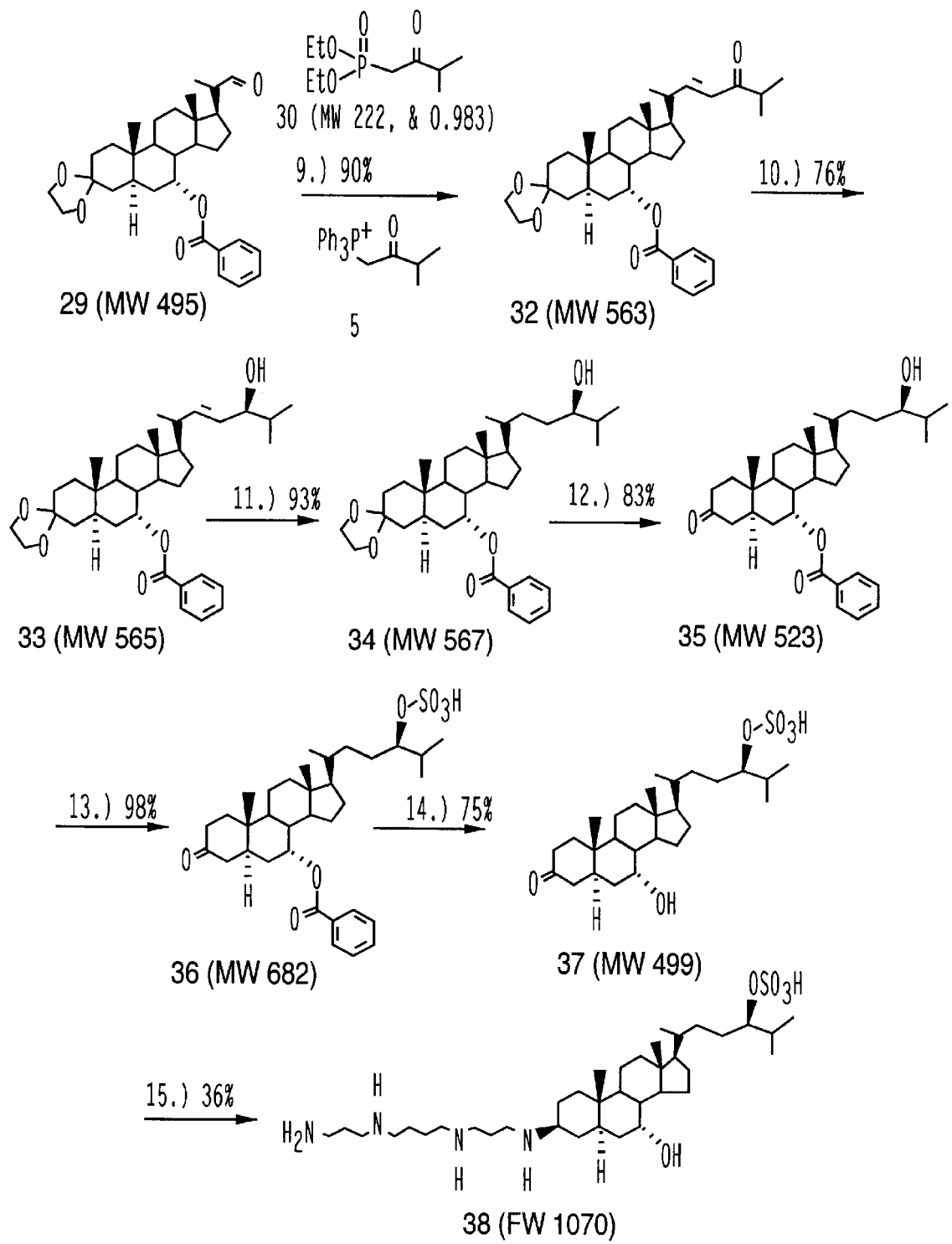
FIG. 15B illustrates a reaction mechanism for producing compound 1436 from steroid 29.

The procedure for producing compound 1436 is illustrated in FIGS. 15A and 15B. This specific description for compound 1436 also should be considered in conjunction with the more generalized process illustrated in FIGS. 10A and 10B.

The procedure began with steroid 21, which is a relatively inexpensive steroid, commercially available in bulk from Pharmacia or Upjohn. This steroid 21 was converted to the ketal 22 with migration of the olefin (see FIG. 15A). Olefin migration was necessary to direct oxidation at the C-7 position. Of course, as more generally shown in FIG. 10A, the specific ketal 22 of FIG. 15A is not necessary. Any suitable protecting groups located at the C-3 carbon can be used. For example, the RS groups shown in FIG. 10A can be the same or different, and each can be an alkyl group having 1–6 carbon atoms. Furthermore, the two R5 groups can join together to form, for example, an ethylene dioxy group, a 1,3-propanedioxy group, a 2-methylene-1,3-propanedioxy group, or a 2,2-dimethyl-1,3-propanedioxy group.

Figure 10A:
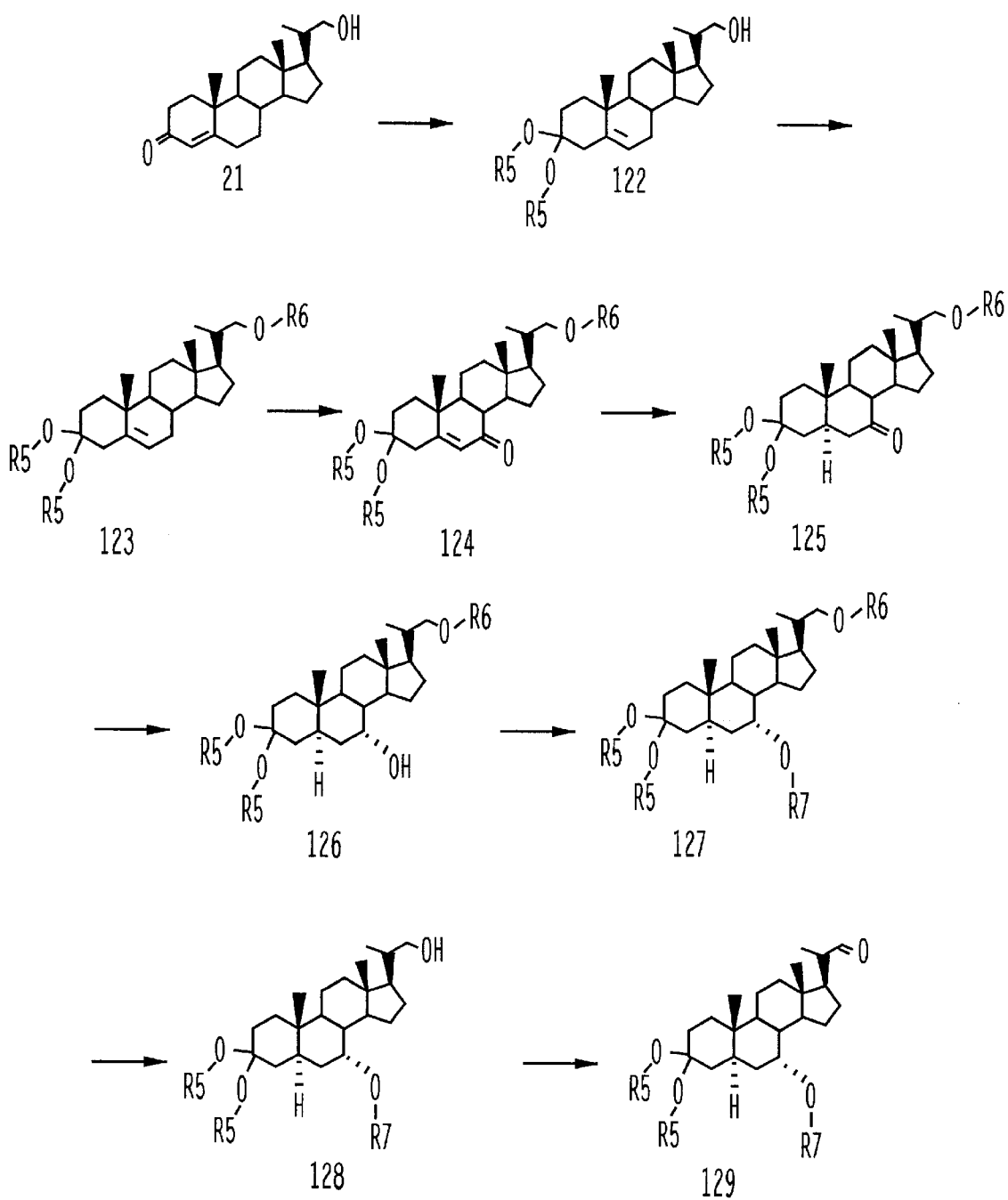
FIG. 10A is a general reaction scheme for producing an aldehyde material for use in the process of the invention from a commercially available starting material.

Thereafter, the C-22 is protected as a t-butyldimethylsilyl ether (compound 23) as shown in FIG. 15A. This procedure also is illustrated more generally in FIG. 10A. The protecting group R6 at the C-22 position of compound 123, as shown in FIG. 10A, need not be a t-butyldimethylsilyl ether compound. Rather, any suitable ether group can be used. In FIG. 10A, R6 can be, for example, formyl, acetyl, propionyl, pivaloyl, cyanoacetyl, benzoyl, substituted benzoyl (ortho or para substituted w/nitro, halogen, alkoxy), methoxycarbonyl (methylcarbonate), ethoxycarbonyl, benzyloxycarbonyl, benzyl, substituted benzyl (o,p-nitro, p-halo, p-methoxy), benzyloxymethyl (BOM), substituted benzyloxymethyl (o,p-nitro, p-halo, p-methoxy), tetrahydrothiopyranyl, tetrahydrothiofuranyl, methylthiomethyl (MTM), trialkylsilyl (alkyl=methyl, ethyl, isopropyl, sec-butyl, tert-butyl, phenyl, or any combination of these), tetrahydropyranyl (THP), 2-methoxyethoxymethyl (MEM), and methoxymethyl (MOM).

Once the C-22 substituent of compound 23 is properly protected, allylic oxidation was achieved with chromium hexacarbonyl and t-butyl hydroperoxide, or by free radical air oxidation (see J. Foricher, et al., U.S. Pat. No. 5,030,739 dated Jul. 9, 1991) to produce enone compound 24. This U.S. patent is entirely incorporated herein by reference. This enone compound (compound 24) was hydrogenated to compound 25, and then treated with K-Selectride® (potassium tri-sec-butylborohydride, commercially available from Aldrich) to produce the 7α-alcohol 26. In this portion of the synthesis method, the generalized process, shown in FIG. 10A, corresponds to the steps of the process shown in FIG. 15A.

The alcoholic hydroxyl group at C-7 (compound 26) was protected as the benzoate (compound 27). Instead of a benzoate group, any suitable protecting group R7 can be used at this point in the procedure, as illustrated generally in FIG. 10A. See compound 127. The protecting group R7 at the C-7 position of compound 127 can be, for example, formyl, acetyl, propionyl, pivaloyl, cyanoacetyl, benzoyl, substituted benzoyl (ortho or para substituted w/nitro, halogen, alkoxy), methoxycarbonyl (methylcarbonate), ethoxycarbonyl, benzyloxycarbonyl, benzyl, substituted benzyl (o,p-nitro, p-halo, p-methoxy), benzyloxymethyl (BOM), substituted benzyloxymethyl (o,p-nitro, p-halo, p-methoxy), tetrahydrothiopyranyl, tetrahydrothiofuranyl, methylthiomethyl (MTM), trialkylsilyl (alkyl=methyl, ethyl, isopropyl, sec-butyl, tert-butyl, phenyl, or any combination of these), tetrahydropyranyl (THP), 2-methoxyethoxymethyl (MEM), and methoxymethyl (MOM).

Once the C-7 substituent group is properly protected, the C-22 alcohol, protected by the t-butyldimethylsilyl ether group, was liberated with fluoride anion to yield compound 28 (compound 128 in FIG. 10A). With the C-22 alcohol selectively available, oxidation under Swern conditions, or with bleach and TEMPO, cleanly produced the C-22 aldehyde 29 (compound 129 in FIG. 10A) in excellent yield, without epimerization of the potentially unstable group at C-20.

The aldehyde 29 (129 in FIG. 10B) was reacted with either the ylide 5 or the anion of the phosphonate ester 30 to produce the enone 32 (132 in FIG. 10B), which is required for the stereoselective reduction step. This is illustrated in FIG. 15B, and more generally in FIG. 10B. Reagent 30 is preferred in this reaction step because the by-products are easily removed upon work-up, making column chromatography unnecessary.

The chiral reduction conditions used in the model substrate 6 as described above worked well in this case to deliver the desired S-allylic alcohol 33 in high yield (compound 133 in FIG. 10B), without the need for chromatography. None of the other isomers was detected by TLC or NMR spectroscopy. The proton NMR spectrum was compatible with the S-stereochemistry at the C-24 position in that the C-22-23 olefin signals were compressed (the olefin signals of the R-allylic alcohols tend to be more separated). Additionally, the carbon resonance for C-24 was at the identical position for compounds 7 and 33 (78.8 ppm), thereby indicating the presence of the hydroxyl at the C-24 position. After hydrogenation of compound 33, an X-ray was performed on the hydrogenation product 34, and this test confirmed the desired 24R assignment. The hydrogenation step is best performed in tetrahydrofuran or ethyl acetate (not in alcohol) in order to decrease the amount of deoxygenated products at C-24. The more generalized reaction scheme for these process steps is illustrated in FIG. 10B.

Figure 1:
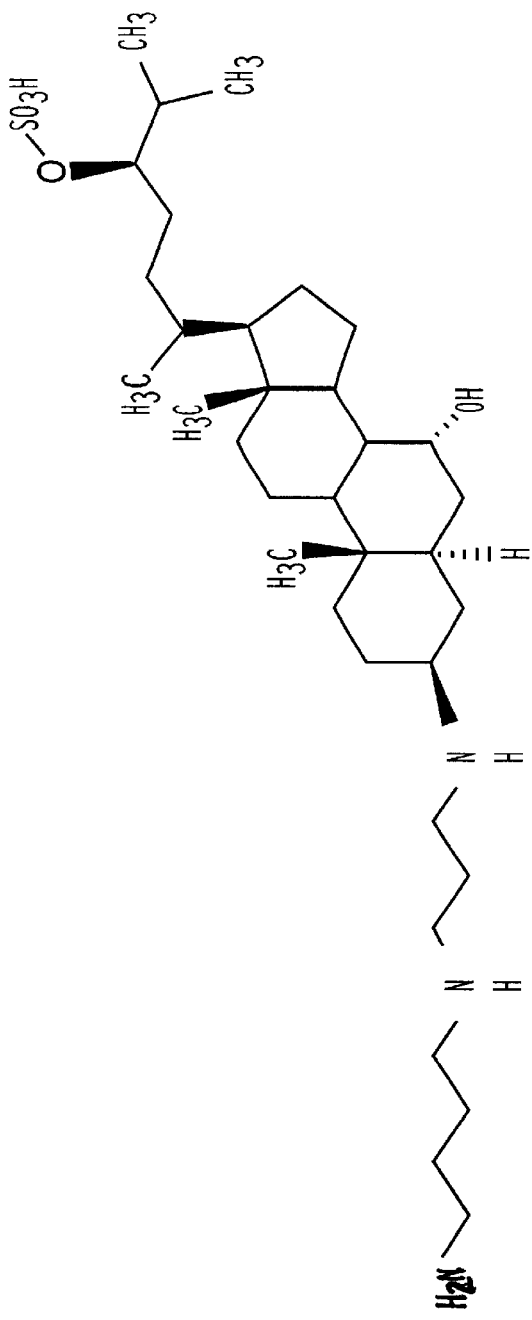
FIG. 1 illustrates the chemical structure of squalamine.
Figure 2:
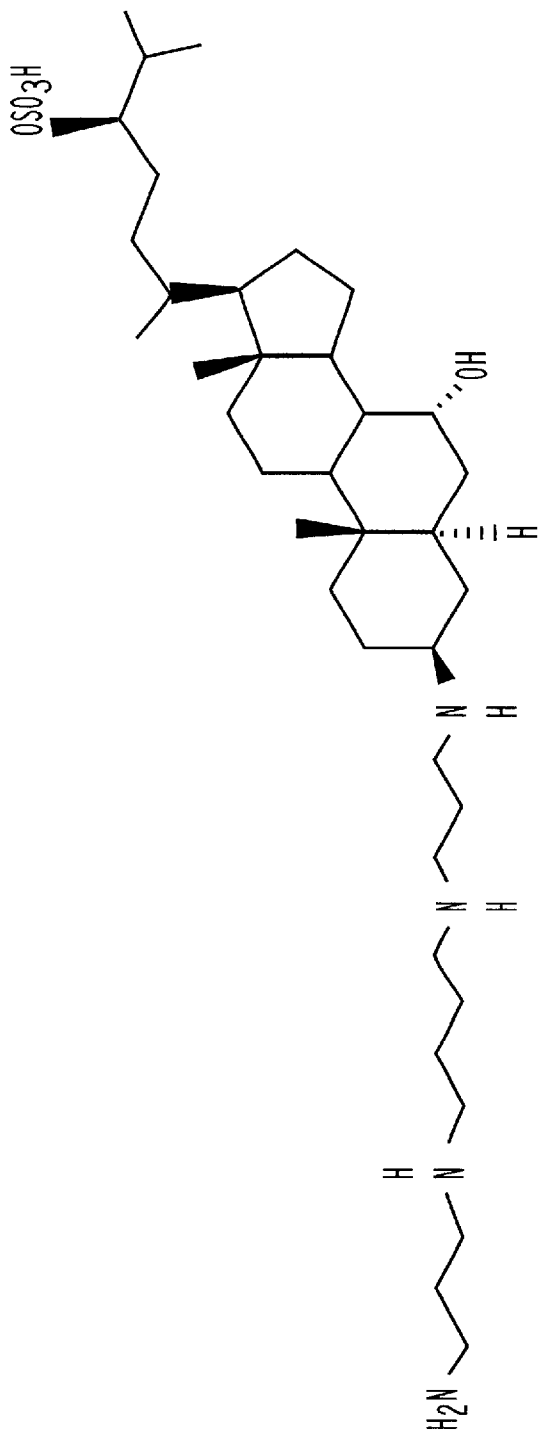
FIG. 2 illustrates the chemical structure of compound 1436.
Figure 3A:
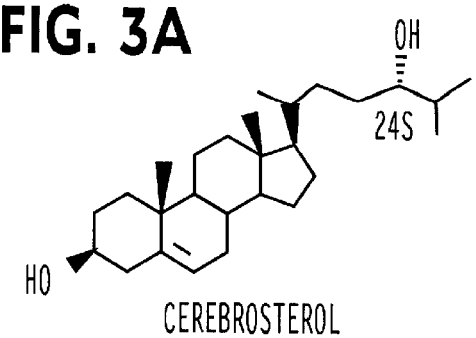
FIG. 3A illustrates the chemical structure of cerebrosterol.
Figure 3B:
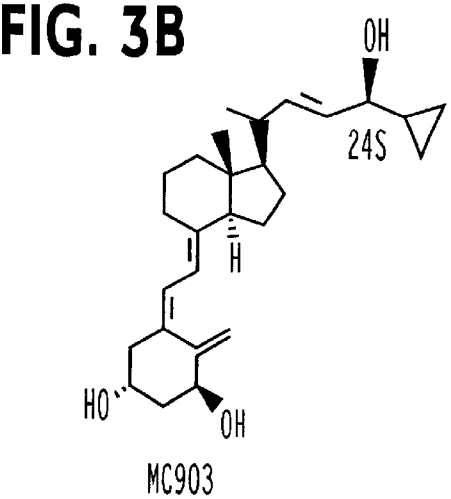
FIG. 3B illustrates the chemical structure of MC 903.
Figure 3C:
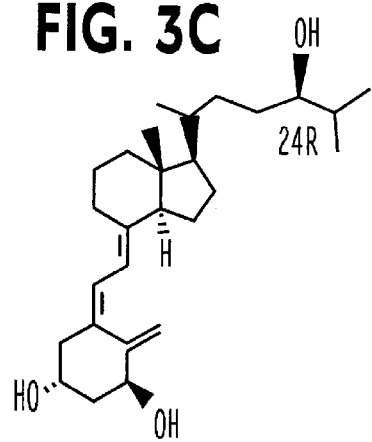
FIG. 3C illustrates the chemical structure of 1α, 24(R)-dihydroxyvitamin $D_3$.
Figure 4A:
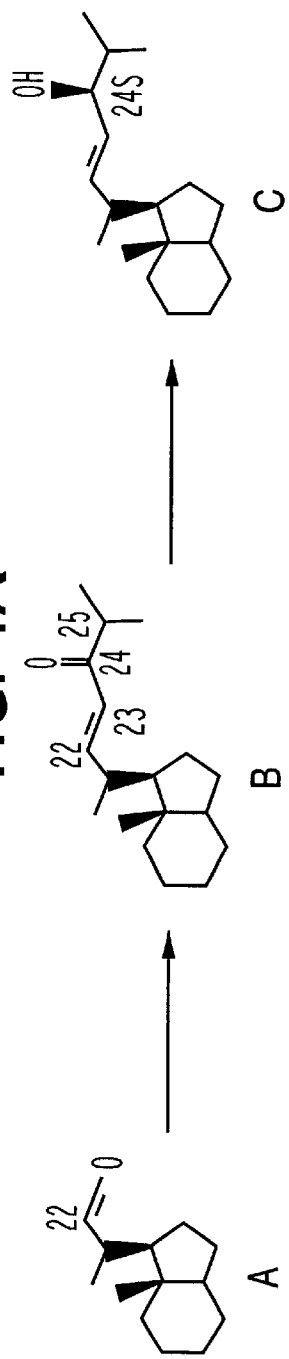
FIG. 4A generally illustrates a first reaction mechanism for producing an unsaturated alcohol from an aldehyde starting material.
Figure 4B:
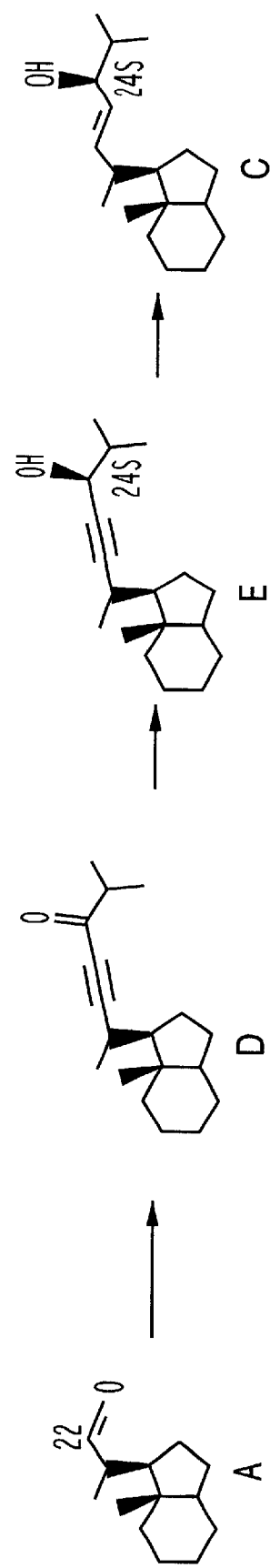
FIG. 4B generally illustrates a second reaction mechanism for producing an unsaturated alcohol from an aldehyde starting material.
Figure 10B:
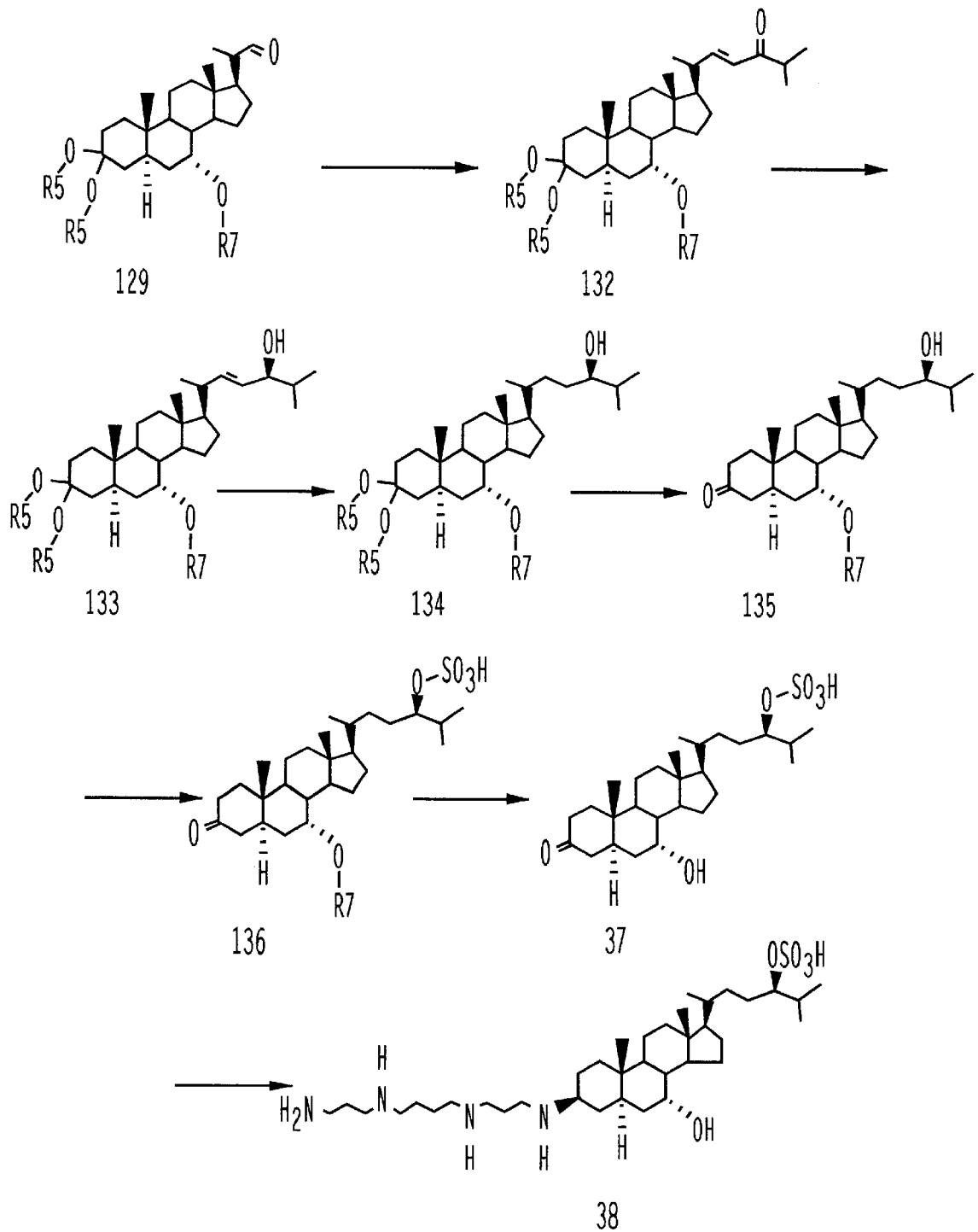
FIG. 10B shows a reaction scheme for producing an aminosterol from the aldehyde material produced in the process of FIG. 10A.

The final steps of the synthesis process, as shown in FIGS. 10B and 15B, involved deprotection of the ketal at C-3 to produce compound 35 (135 in FIG. 10B), sulfation of the C-24 alcohol (compounds 36 (FIG. 15B) and 136 (FIG. 10B)), and cleavage of the benzoate at C-7 (to produce compound 37). Compounds 36, 136, and 37 are best isolated as their sodium or potassium salts. Finally reductive amination with spermine and sodium borohydride produced compound 38, which corresponds to compound 1436 illustrated in FIG. 2. The overall yield of compound 1436 from the specific synthesis process shown in FIGS. 15A and 15B was about 4%.

Squalamine (42) also can be produced by this same general process, although, when producing squalamine, compound 37 (FIG. 17) is coupled to the protected spermidine derivative 41 to afford the intermediate 43. The nitrile functionality within 43 is reduced with hydrogen gas under platinum catalysis at acidic pH to afford squalamine (42) in approximately 60% yield for two steps. If this reduction were not performed at acidic pH, a very poor yield of squalamine was obtained. In that case products were obtained from the internal nitrogen cyclizing on the nitrile.

Spermidine derivative 41 has been used as a spermidine equivalent in one other report (Umeda, et al., *J. Antibiotics*, 40, 1303–1315, 1987), but it has never been applied to the synthesis of squalamine. It is especially useful in this case because the protected amino function (the nitrile) is stable to reductive amination conditions, yet it is easily converted to an amino function (spermidine) by catalytic hydrogenation under conditions that do not affect the sulfate. The sulfate would be cleaved under strongly acidic conditions, as in the case of removal of a BOC-group. The spermidine derivative 41 was easily prepared in one step in good yield under the improved reaction conditions (73% versus 42% yield). The BOC-protected spermidine derivative used by Moriarty and Frye is more difficult to prepare and is not cleavable in the presence of a sulfate.

2. Using Steroid 50 as a Starting Material

Figure 16A:
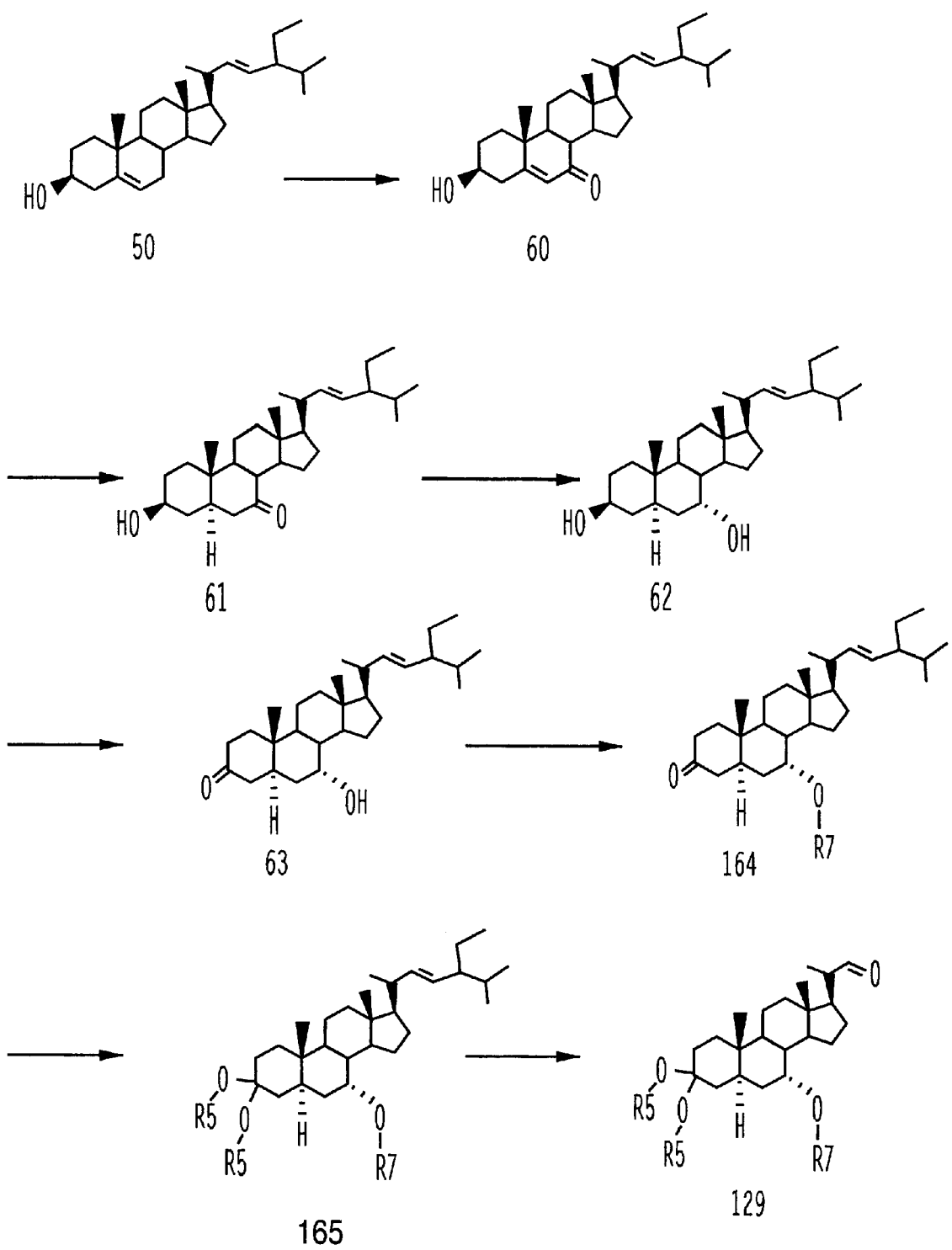
FIG. 16A illustrates a general reaction scheme for producing a class of steroids including steroid 29.
Figure 16B:
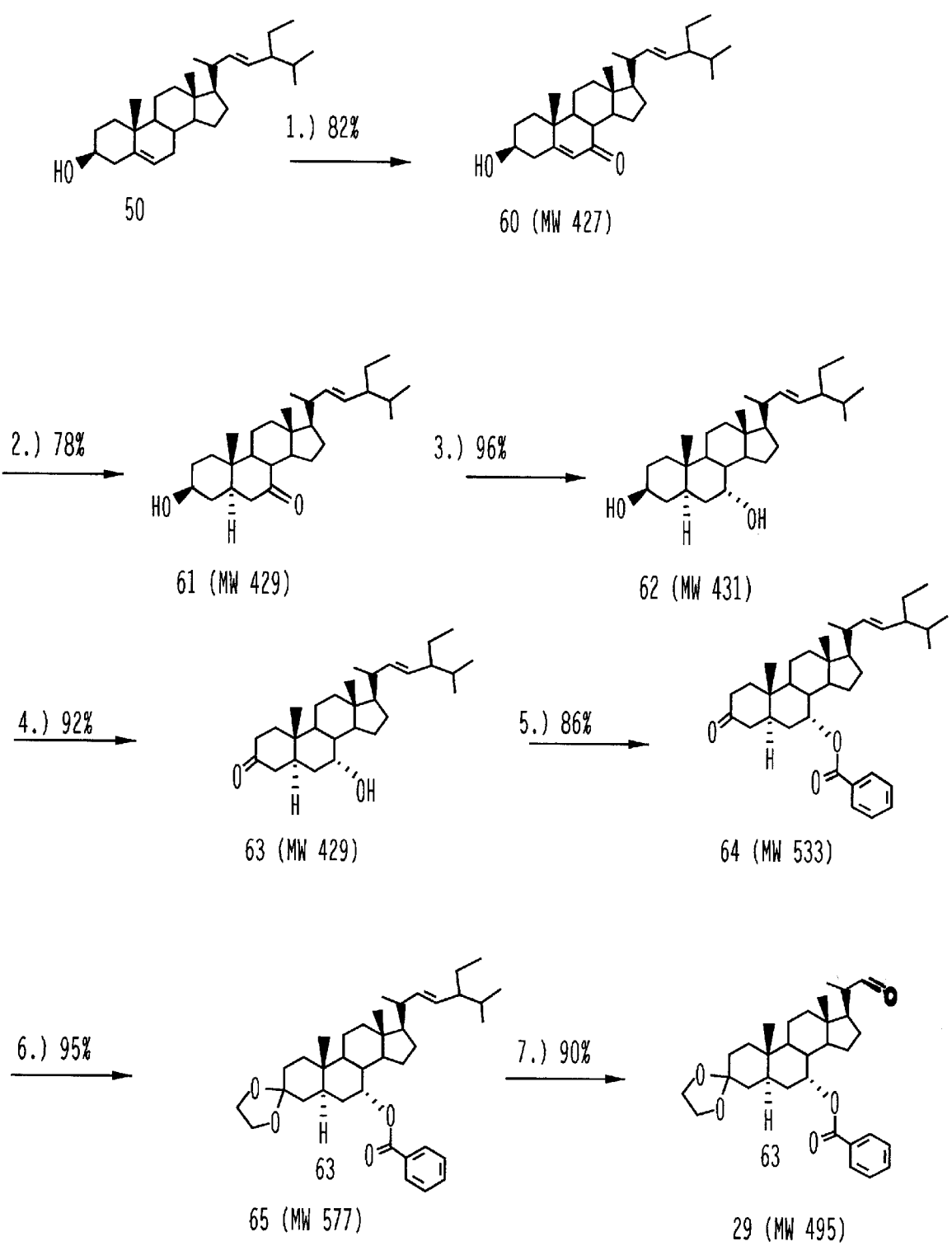
FIG. 16B illustrates.a specific reaction mechanism for producing steroid 29 based on the general mechanism shown in FIG. 16A.

The aldehyde 29 from FIGS. 15A and 15B also can be prepared from the commercially available steroid stigmasterol, compound 50 shown in FIGS. 16A and 16B, in seven steps. FIG. 16A shows a generalized reaction mechanism for producing compound 129, and FIG. 16B shows a more specific example for producing the specific aldehyde 29. The specific reaction steps of FIG. 16B also are described in more detail below, in the "Experimental Section" of this patent application.

In this process, first, stigmasterol 50 was oxidized in air, to give the unsaturated ketone 60. The enone double bond was selectively reduced by dissolving metal reduction (Li/NH$_3$) to produce the required a-hydrogen at the C-5 position (compound 61). K-Selectride® (potassium tri-sec-butylborohydride from Aldrich) reduced the ketofunctionality contained in compound 61 to yield an a-hydroxy group at the C-7 position (this is compound 62). Selective oxidation of the C-3 hydroxyl group was achieved with silver carbonate to produce compound 63. The hydroxyl group was then protected as the benzoate (compound 64) in the process shown in FIG. 16B. As noted above in conjunction with FIG. 10A, however, protection as a benzoate is not necessary, but any appropriate protecting group R7 can be used. R7 in FIG. 16A has the same meaning as that described above in FIG. 10A.

Thereafter, the ketone at the C-3 position was protected as the ethylene ketal to produce compound 65 (FIG. 16B). Again, as described above in conjunction with FIG. 10A, any appropriate protecting group(s) R5 can be used in this process. R5 can have the same meaning in FIG. 16A as it has in FIG. 10A. Ozonolysis produced compound 29 (or compound 129 in FIG. 16A), which was identical to that prepared by the scheme shown in FIG. 15A.

This aldehyde 29 can be used to produce compound 1436 and/or squalamine, by the same process as that illustrated in FIG. 15B.

In the processes described above, the examples for R6 are not the only possible protecting groups for the C-22 position. Suitable protection R6 for the C-22 hydroxyl varies. The protecting group need only be removable under conditions where the C-3 and C-7 protecting groups are stable. Depending upon which point in the synthesis where the C-22 is protected, appropriate protection varies. If C-22 is protected prior to the allylic oxidation, protecting groups sensitive toward the oxidation conditions are not preferred (e.g., sulfur containing protecting groups). Hydrogen labile protecting groups also are less suitable if applied prior to the hydrogenation; however, virtually any OH protecting group not requiring strongly acidic conditions for removal is acceptable if applied immediately prior to K-Selectride® reduction (K-Selectride® is potassium tri-secbutylborohydride available from Aldrich). Readily cleaved esters are particularly useful in that they allow for selective cleavage in the presence of another more stable ester at C-7. Benzyl ethers, benzyloxymethyl ethers, and carbonates are most useful if applied after the first hydrogenation.

As with R6, the C-7 OH protection R7 should not require strongly acidic conditions for removal. Virtually all esters and silyl ethers are suitable for R7 as long as R6 can be removed in its presence.

Figure 10C:
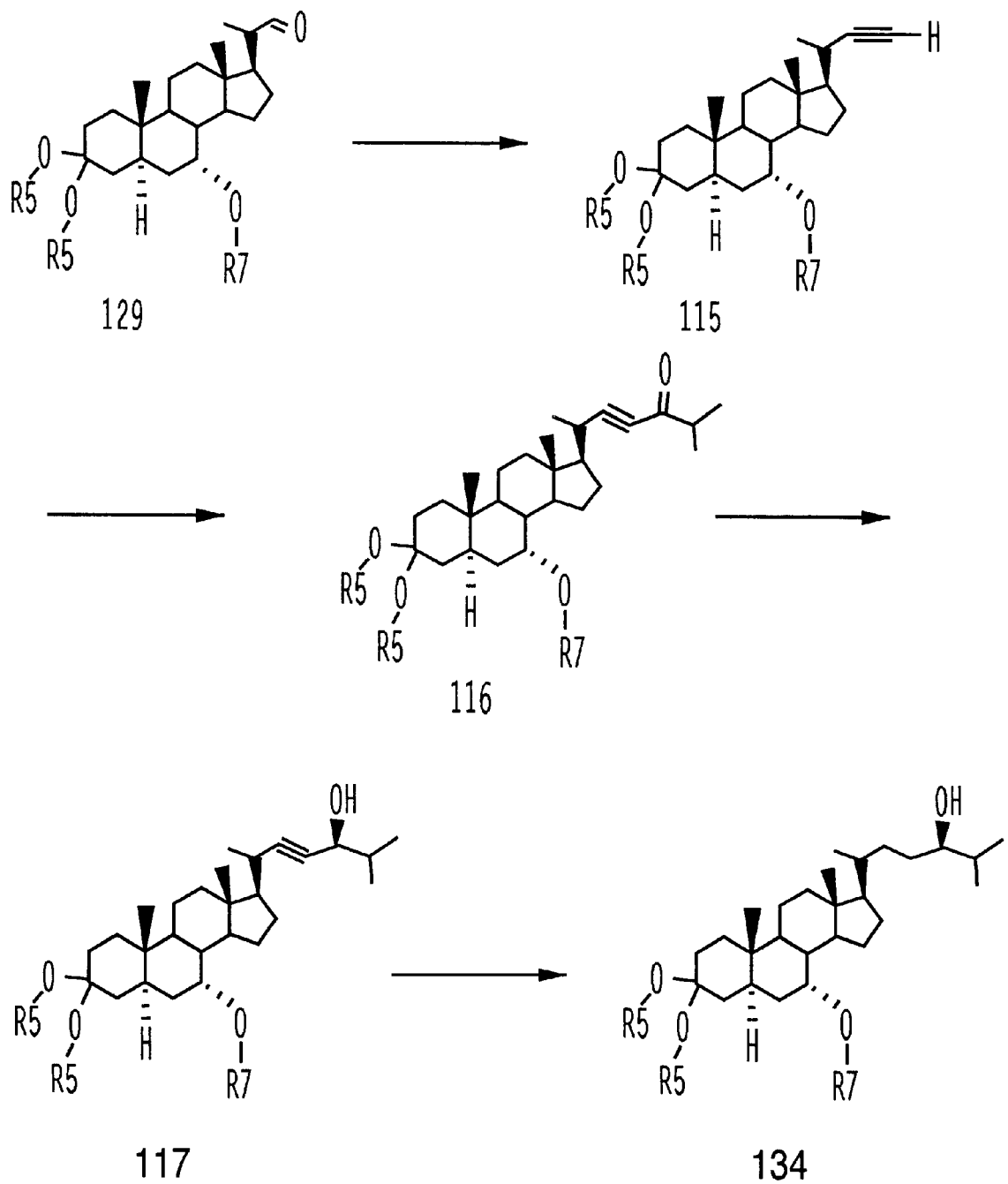
FIG. 10C shows a reaction scheme for using the aldehyde material produced in the process of FIG. 10A to make a stereospecific alcohol.

An alternative procedure for forming compound 134 from compound 129 is illustrated in FIG. 10C. This procedure uses the alkyneone intermediates described above in conjunction with FIGS. 8, 9 and 14. In FIG. 10C, R5 and R7 have the definitions described above with respect to FIGS. 10A and 10B.

D. Conclusion Regarding Production of C-24 Hydroxylated Steroids

Suitable cholest-22-ene-24-one and cholest-22-yne-24-one systems can be easily constructed in one and two steps, respectively, from a C-22 aldehyde. These systems can then be selectively reduced with Corey's oxazaborolidine-borane complexes to produce the 24-S-allylic alcohol and 24-S-propargylic alcohols. These materials correspond to the 24-R alcohol after removal of the C-22-23 multiple bonds (i.e., the unsaturation bonds between the C-22 and C-23 carbons). This procedure has been demonstrated on compounds 6, 16, and 32. These two or three step procedures provide the most rapid access in a practical, scalable way to the aminosterol class of compounds that include a C-24R alcohol or other substituent. The C-24R alcohol can be converted to a sulfate grouping or other suitable substituent at the C-24 position. The process in accordance with the invention eliminates the lengthy procedures used by others to do the same transformation, as described in the documents noted above.

II. Intermediates

This invention also relates to the several intermediates that are identified in FIGS. 10A, 10B, 10C, 12, 14, 15A, 15B, 16A and 16B. The intermediates in accordance with the invention are the compounds shown in the above-noted Figures, except for compounds 1, 2, 21, 22, 38, 50, 60, and 122. These compounds are intermediates useful in the production of various compounds including aminosterols such as squalamine and compound 1436. These aminosterols can be used in pharmaceutical products.

In one embodiment, this invention relates to intermediates formed in the synthesis of squalamine or homologous aminosterols. These intermediates have the composition:

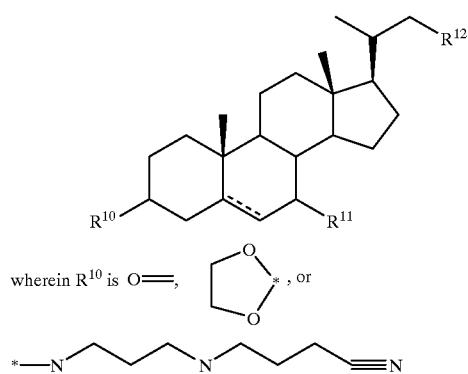

wherein $R^{10}$ is O=,

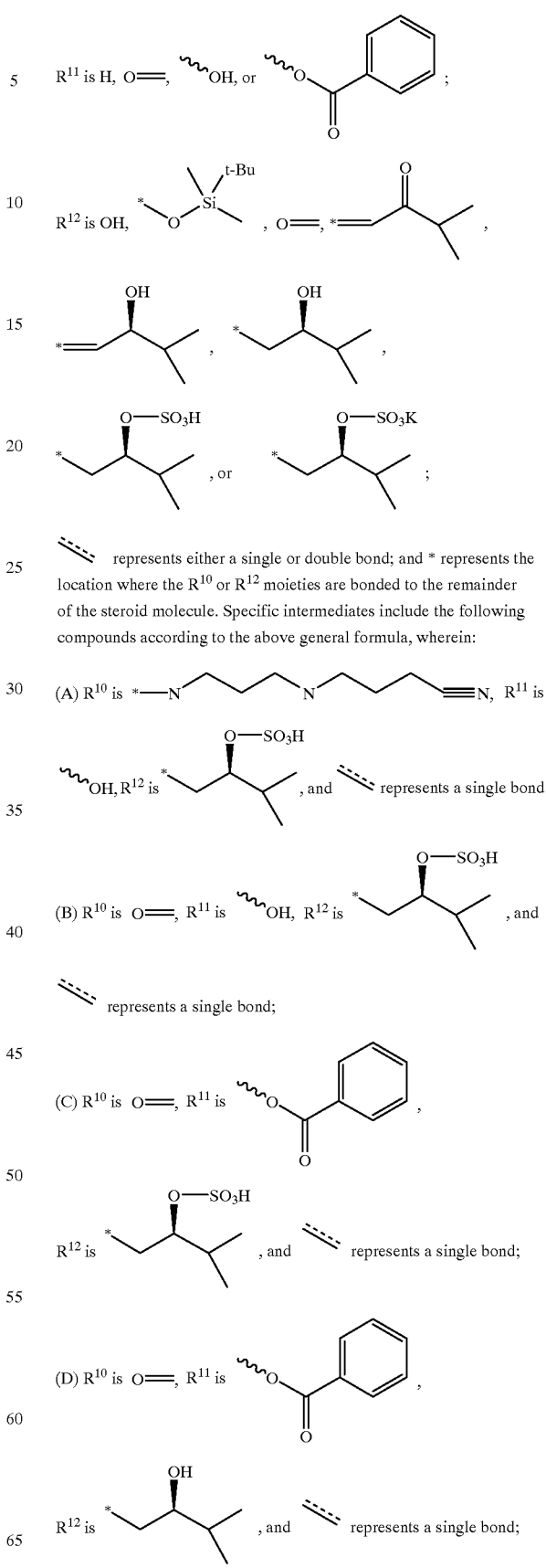

$R^{11}$ is H, O=, ⁓OH, or ⁓O-benzoate;

$R^{12}$ is OH, O-Si(t-Bu), O=, *=C(O)iPr, *-CH=CH-CH(OH)iPr, *-CH₂-CH₂-CH(OH)iPr, *-CH₂-CH₂-CH(OSO₃H)iPr, or *-CH₂-CH₂-CH(OSO₃K)iPr;

⁓ represents either a single or double bond; and * represents the location where the $R^{10}$ or $R^{12}$ moieties are bonded to the remainder of the steroid molecule. Specific intermediates include the following compounds according to the above general formula, wherein:

(A) $R^{10}$ is *—N-propyl-N-butyl-CN chain, $R^{11}$ is ⁓OH, $R^{12}$ is *-CH₂-CH₂-CH(OSO₃H)iPr, and ⁓ represents a single bond;

(B) $R^{10}$ is O=, $R^{11}$ is ⁓OH, $R^{12}$ is *-CH₂-CH₂-CH(OSO₃H)iPr, and ⁓ represents a single bond;

(C) $R^{10}$ is O=, $R^{11}$ is ⁓O-benzoate, (D) $R^{10}$ is O=, $R^{11}$ is ⁓O-benzoate, $R^{12}$ is *-CH₂-CH₂-CH(OH)iPr, and ⁓ represents a single bond;

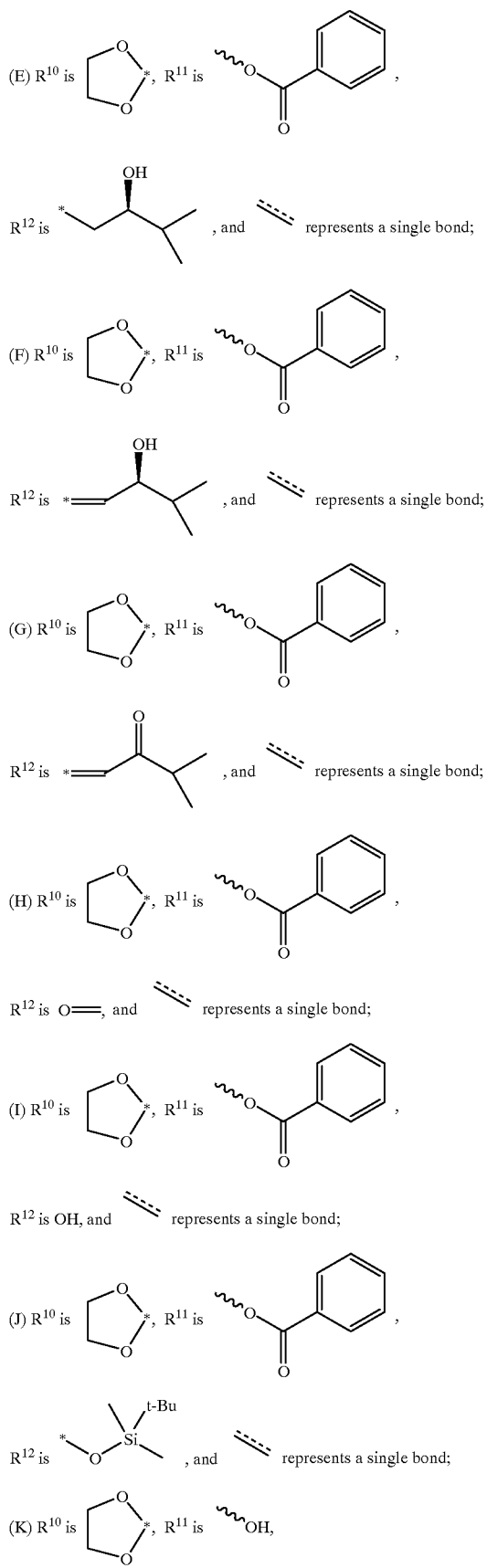
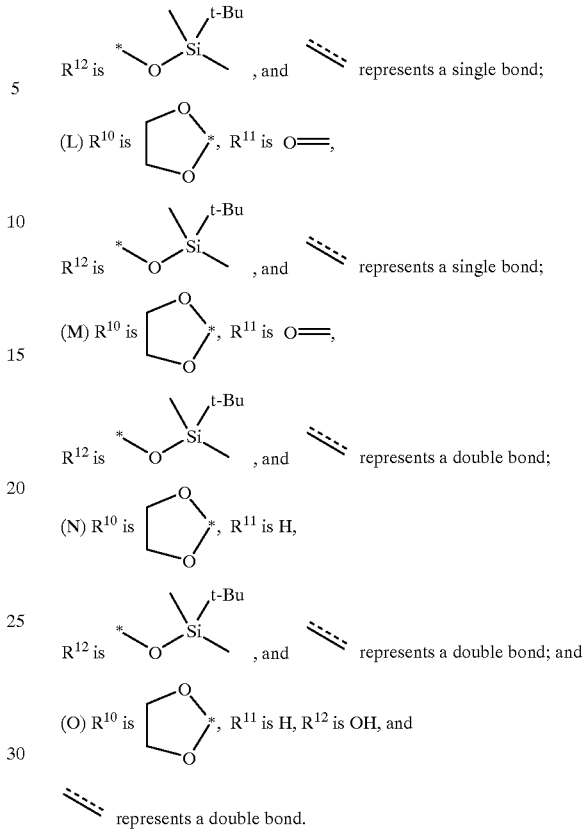
represents a double bond.
Particularly preferred intermediates include intermediates 61 through 65 shown in FIG. 16B. These intermediates are as follows:
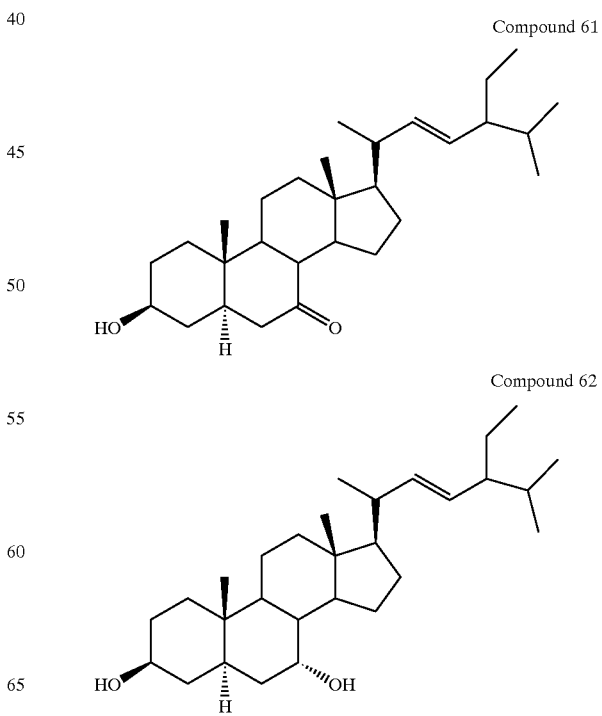
Compound 61
Compound 62

In another aspect, intermediates according to the invention can be defined by the following general formula:

wherein:

$R^{10}$ is O=, [1,3-dioxolane], [1,3-dioxane], [5,5-dimethyl-1,3-dioxane],

N≡C—CH$_2$CH$_2$CH$_2$—NH—CH$_2$CH$_2$CH$_2$—NH—, (C$_1$ to C$_6$)—O— , or HO ; $R^{11}$ is H, O=, HO , or $R^{13}$—O ; $R^{12}$ is OH, —OR$^{14}$, O=,

[various substructures with OH, alkene, alkyne, O—SO$_3$H, O—SO$_3$K groups]; or

[alkene side chain];

~~~ represents a single or double bond;

\* represents the location where the $R^{10}$ or $R^{12}$ moieties are bonded to the remainder of the steroid molecule;

$C_1$ to $C_6$, each independently represents an alkyl, alkenyl, or alkynyl group, having 1 to 6 carbon atoms, wherein the group may be substituted or unsubstituted; and $R^{13}$ and $R^{14}$, each independently represents formyl; acetyl; propionyl; pivaloyl; cyanoacetyl; benzoyl; benzoyl ortho or para substituted with nitro, halogen, or alkoxy; methoxycarbonyl (methylcarbonate); ethoxycarbonyl; benzyloxycarbonyl; benzyl; benzyl ortho or para substituted with nitro; benzyl para substituted with a halogen; benzyl para substituted with a methoxy; benzyloxymethyl; benzyloxymethyl ortho or para substituted with nitro; benzyloxymethyl para substituted with a halogen; benzyloxymethyl para substituted with a methoxy; tetrahydrothiopyranyl; tetrahydrothiofuranyl; methylthiomethyl; trialkylsilyl, wherein each alkyl is independently selected from the group of methyl, ethyl, isopropyl, sec-butyl, tert-butyl, and phenyl; tetrahydropyranyl; 2-methoxyethoxymethyl; and methoxymethyl.

III. Experimental Section

A. General

Unless otherwise noted, 77.23 ppm was used as the reference for CDCl$_3$ in $^{13}$C NMR experiments.

B. Preparation of Specific Compounds

1. Preparation of Compound 2 (FIG. 12)

Ammonia (60 ml) was condensed into a flask under nitrogen, and lithium wire (98 mg, 14 mmol) was added. Steroid 1 (FIG. 12) (1.0 g, 3.0 mmol) was dissolved in anhydrous tetrahydrofuran (25 ml) and added dropwise. Steroid 1 is commercially available from Pharmacia or Upjohn. After 40 minutes, the reaction was quenched with solid ammonium chloride until the blue color disappeared, and then the mixture was allowed to evaporate overnight. The resulting solid was partitioned between water (150 ml) and ethyl acetate (200 ml). The aqueous layer was extracted with portions of ether and dichloromethane, and the combined organic layers were washed with brine, dried over sodium sulfate, and evaporated to yield a white solid. This material was dissolved in dichloromethane and purified by flash chromatography (gradient elution with 10 to 40% ethyl acetate in hexane) to produce compound 2 (710 mg, 71%, mp 168–170° C.).

Compound 2: $^1$H NMR (400 MHZ, CDCl$_3$): δ 3.64 (d of d, J=10 and 2 Hz, 1H), 3.36 (d of d, J=10 and 3 Hz, 1H), 2.33–1.08 (m, 24H), 1.05 (d, J=6.7 Hz, 3H), 1.02 (s, 3H), 0.71 (s, 3H); $^{13}$C NMR (400 MHZ, CDCl$_3$): δ 212.4, 68.1, 56.2, 53.9, 52.7, 46.8, 44.9, 42.8, 39.9, 38.9, 38.7, 38.4, 35.8, 35.6, 31.9, 29.1, 27.9, 24.5, 21.6, 16.9, 12.3, 11.6; Anal. Calcd. for $C_{22}H_{36}O_2$: C, 79.46; H, 10.91. Found: C, 79.54; H, 10.48.

2. Preparation of Compound 3

A solution of compound 2 (710 mg, 2.14 mmol), ethylene glycol (1.13 ml, 20 mmol), and p-toluenesulfonic acid monohydrate (41 mg, 0.21 imnol) in benzene (90 ml) was heated at reflux overnight with the removal of water by a Dean-Stark trap. The reaction mixture was cooled, washed with saturated sodium bicarbonate solution and brine, dried over sodium sulfate, and evaporated to yield compound 3 (725 mg, 90%, mp 184–186° C.).

Compound 3: $^1$H NMR (400 MHZ, CDCl$_3$): δ 3.94 (s, 4H), 3.64 (d of d, J=10.3 and 3.1 Hz, 1H), 3.36 (d of d, J=10.3 and 6.8 Hz, 1H), 1.98–1.94 (m, 1H), 1.83–1.76 (m, 1H), 1.7–1.0 (m, 22H), 1.04 (d, J=7.0 Hz, 3H), 0.82 (s, 3H), 0.68 (s, 3H; $^{13}$C NMR (400 MHZ, CDCl$_3$): δ 109.6, 68.2, 64.3, 56.4, 54.2, 52.7, 43.9, 42.9, 40.1, 39.0, 38.2, 36.2, 35.9, 35.7, 35.6, 32.1, 31.4, 28.8, 27.9, 24.5, 21.4, 16.9, 12.4, 11.6; IR (KBr, cm$^{-1}$): 3315, 2930, 1447, 1360, 1179, 1101; Anal. Calcd. for $C_{24}H_{40}O_3$: C, 76.55; H, 10.71. Found: C, 74.91; H, 10.06.

3. Preparation of Compound 4

A suspension of potassium acetate (140 mg, 1.43 mmol) and pyridinium chlorochromate (1.09 g, 5.06 mmol) in dichloromethane (20 ml) was treated with compound 3 (1.0 g, 2.65 mmol) in dichloromethane (10 ml). After 1.25 hours, the reaction mixture was diluted with ether and filtered through Celite® (Celite® is a form of SiO$_2$ sold by Aldrich). The ether layers were combined, washed with saturated sodium bicarbonate solution and brine, dried over sodium sulfate, and evaporated to give a white solid. This material was purified by flash chromatography (gradient elution with 5 to 25% ethyl acetate in hexane) to provide compound 4 (604 mg, 61%, mp 141–144° C.).

Compound 4: $^1$H NMR (400 MHZ, CDCl$_3$): δ 9.56 (d, J=3.5 Hz, 1H), 3.94 (s, 4H), 2.34 (m, 1H), 1.93–0.86 (m, 23H), 1.11 (d, J=6.5 Hz, 3H), 0.82 (s, 3H), 0.70 (s, 3H); $^{13}$C NMR (400 MHZ, CDCl$_3$): δ 205.4, 109.6, 64.3, 55.9, 54.2, 51.3, 49.7, 43.8, 43.4, 39.9, 38.1, 36.2, 35.7, 32.1, 31.4, 28.7, 27.2, 24.8, 21.3, 13.6, 12.7, 11.6; IR (KBr, cm$^{-1}$): 3478, 2934, 2725, 1721, 1445, 1356, 1101; MS (+FAB): 375.3 (M+1, 60), 307.1 (100), 289.1 (45).

4. Preparation of Compound 6

A solution of compound 4 (820 mg, 2.19 mmol) and compound 5 (1.52 g, 4.38 mmol) in methyl sulfoxide (4 ml) was heated to 110° C. overnight, cooled, dissolved in ethyl acetate, washed with water, and dried. The crude material was purified by flash chromatography (gradient elution with 5 to 15% ethyl acetate in hexane) to yield compound 6 (720 mg, 74%, mp 168–169° C.). A procedure for preparing compound 5 and its reaction with C-22 aldehydes are described in M. Fryberg, A. C. Oehlschlager, and A. M. Unrau, "The Synthesis of Possible Polyene Intermediates in Phytosterol Biosynthesis," *Tetrahedron*, 1971, Vol. 27, pp. 1261–1274. This article is entirely incorporated herein by reference.

Compound 6: $^1$H NMR (400 MHZ, CDCl$_3$): δ 6.71 (d of d, J=16 and 9 Hz, 1H), 6.06 (d, J=16 Hz, 1H), 3.94 (s, 4H), 2.83 (hept, J=7 Hz, 1H), 2.25 (m, 1H), 1.95 (m, 1H), 1.7–1.0 (m, 22H), 1.11–1.08 (m, 9H), 0.82 (s, 3H), 0.69 (s, 3H); $^{13}$C NMR (400 MHZ, CDCl$_3$): δ 204.9, 152.9, 126.3, 109.6, 64.3, 56.5, 55.2, 54.2, 43.8, 43.2, 40.2, 40.0, 38.4, 38.1, 36.2, 35.6, 32.0, 31.3, 28.7, 28.4, 24.4, 21.3, 19.5, 18.8, 18.7, 12.6, 11.6; Anal. Calcd. for $C_{29}H_{46}O_3 \cdot 0.1H_2O$: C, 78.36; H, 10.48. Found: C, 78.21; H, 10.68.

5. Preparation of Compounds 7 and 8

A solution of compound 6 (100 mg, 0.226 mmol) was dissolved in anhydrous tetrahydrofuran (2 ml), treated with 1 M lithium aluminum hydride in tetrahydrofuran (380 μl, 0.38 mmol), and refluxed for 1 hour under nitrogen. After cooling, the reaction was quenched with methanol, filtered through Celite® (SiO$_2$, available from Aldrich), and purified by flash chromatography (gradient elution with 7 to 10% ethyl acetate in hexane) to provide pure compound 8 (18 mg, 18%, mp 147–150° C., less polar by TLC 5% acetone/chloroform), followed by two mixed fractions of compound 7 (more polar) and compound 8 (49+15 mg=64 mg, 64%).

Compound 8: $^1$H NMR (400 MHZ, CDCl$_3$): δ 5.49 (d of d, J=15.4 and 8.2 Hz, 1H), 5.37 (d of d, J=15.4 and 7.0 Hz, 1H), 3.94 (s, 4H), 3.77 (t, J=6.4 Hz, 1H), 2.3–1.0 (m, 25H), 1.02 (d, J=6.5 Hz, 3H), 0.92 (d, J=6.7 Hz, 3H), 0.87 (d, J=6.8 Hz, 3H), 0.82 (s, 3H), 0.68 (s, 3H); $^{13}$C NMR (400 MHZ, CDCl$_3$): δ 139.4, 128.6, 109.6, 78.42 (C24-R), 64.3, 56.6, 56.0, 54.2, 43.9, 42.8, 40.1, 40.0, 38.1, 36.2, 35.6, 34.1, 32.1, 31.3, 28.8, 24.4, 21.4, 20.6, 18.4, 12.5, 11.7, 11.6; Anal. Calcd. for $C_{29}H_{48}O_3$: C, 78.33; H, 10.88. Found: C, 78.24; H, 10.87.

Mixture of compounds 7 and 8: $^{13}$C NMR (400 MHZ, CDCl$_3$): δ 78.80, 78.37 (C24-S and R).

6. Synthesis of Compound 10

A solution of compound 8 (75 mg, 0.17 mmol) in ethyl acetate (4 ml) was treated with 10% palladium on carbon (76 mg) and hydrogen (40 psi) on a Parr apparatus for 6 hours. The reaction mixture was filtered through Celite® (SiO$_2$, available from Aldrich), evaporated, and recrystallized (ethyl acetate in hexane) to provide compound 10 (18 mg, 24%, mp 122–132° C.).

Compound 10: $^1$H NMR (400 MHZ, CDCl$_3$): δ 3.30 (m, 1H), 2.0–1.0 (m, 29H), 0.93–0.89 (m, 9H), 0.81 (s, 3H), 0.65 (s, 3H); $^{13}$C NMR (400 MHZ, CDCl$_3$): δ 109.7, 77.64 (DEPT, C24-S), 64.4, 56.7, 56.2, 56.1, 54.2, 43.9, 42.8, 40.2, 38.2, 36.2, 36.1, 35.7, 35.6, 33.4, 32.4, 32.1, 31.4, 30.9, 30.0, 28.8, 28.4, 24.4, 21.4, 19.3, 19.0, 18.7, 18.6, 18.5, 16.9, 12.3, 11.6; MS (+FAB): 447.3 (M+1, 100), 90.9 (80); Anal. Calcd. for $C_{29}H_{50}O_3$: C, 77.97; H, 11.28. Found: C, 77.34; H, 10.84.

7. Synthesis of Compounds 9 and 10

A mixture of compounds 7 and 8 (8.5 mg, 0.019 mmol) in ethanol (5 ml) was treated with 10% palladium on carbon (22 mg) and hydrogen (40 psi). The reaction mixture was filtered through Celite® ($SiO_2$, available from Aldrich) and evaporated to yield a mixture of compounds 9 and 10 (8 mg).

Mixture of compounds 9 and 10: $^{13}$C NMR (400 MHZ, DEPT, $CDCl_3$): δ 77.66, 77.31 (C24-S and R).

8. Stereoselective Synthesis of Compound 7

(R)-diphenylprolinol (0.286 g, 1.13 mmol) and trimethylboroxane (0.14 g, 1.13 mmol) were combined in toluene (30 ml). This mixture was stirred at 50° C. for 1 hour and then heated to reflux until 20 ml of an azeotropic mixture was distilled. After cooling, 1 M borane-tetrahydrofuran complex (2.8 ml, 2.8 mmol) was added at room temperature, and the solution was stirred for 2 hours. Then, a solution of compound 6 (0.50 g, 1.13 mmol) in toluene (15 ml) was added at −20° C. over 1.75 hours. After an additional hour, the reaction was quenched with water (20 ml) and 5% hydrochloric acid (20 ml). After stirring for 30 minutes at room temperature, toluene (50 ml) was added, and the organic phase was washed with brine (3×20 ml) to pH 7. The organic phase was dried over magnesium sulfate, filtered, and concentrated in vacuo to yield compound 7 (0.48 g, de estimated by TLC ($CHCl_3$/i-$Pr_2$O 80:20) calibration= 94–98%). After purification by chromatography, the alcohol was obtained as a white solid (0.36 g, 72%, mp 157° C.).

Compound 7: $^1$H NMR (400 MHZ, $CDCl_3$): δ 5.43 (d of d, J=15.3 and 8.3 Hz, 1H), 5.34 (d of d, J=15.3 and 7 Hz, 1H), 3.93 (s, 4H), 3.72 (t, J=7 Hz, 1H), 2.05 (m, 1H), 1.93 (m, 1H), 1.8–1.0 (m, 23H), 1.02 (d, J=6.6 Hz, 3H), 0.92 (d, J=6.6 Hz, 3H), 0.86 (d, J=6.5 Hz, 3H), 0.80 (s, 3H), 0.67 (s, 3H); $^{13}$C NMR (400 MHZ, $CDCl_3$): δ 140.0, 128.6, 109.6, 78.82 (C24-S), 64.3, 56.7, 55.8, 54.2, 43.8, 42.8, 40.3, 40.1, 38.1, 36.2, 35.6, 34.1, 32.1, 31.3, 29.0, 28.7, 24.4, 21.4, 20.6, 18.6, 18.4, 12.4, 11.6; MS (+FAB): 445.3 (M+1, 48), 427.3 (37), 90.9 (100); Anal. Calcd. for $C_{29}H_{48}O_3$: C, 78.33; H, 10.88. Found: C, 78.22; H, 10.59.

9. Synthesis of Compound 9

A solution of compound 7 (19 mg, 0.043 mmol) in ethyl acetate (10 ml) was treated with 10% palladium on carbon (5 mg) and 40 psi of hydrogen for 4 hours. The reaction was filtered, concentrated in vacuo, recrystallized from ethyl acetate in hexane, and then purified by flash chromatography (1 cm diameter, gradient elution with 7 to 8% ethyl acetate in hexane) to provide compound 9 (11 mg, 57%, mp 125–127° C.).

Compound 9: $^1$H NMR (400 MHZ, $CDCl_3$): δ 3.94 (s, 4H), 3.31 (m, 1H), 2.0–1.0 (m, 29H), 0.92–0.89 (m, 9H), 0.81 (s, 3H), 0.66 (s, 3H); $^{13}$C NMR (400 MHZ, $CDCl_3$): δ 109.7, 77.29 (DEPT, C24-R), 64.3, 56.7, 56.3, 54.2, 43.9, 42.8, 40.2, 38.2, 36.2, 35.9, 35.7, 33.7, 32.2, 32.1, 31.4, 30.8, 28.8, 28.5, 24.4, 21.4, 19.1, 18.8, 17.4, 12.3, 11.6; MS (+FAB): 447.4 (M+1).

10. Preparation of Compound 15 (FIG. 14)

A solution of dimethyl diazomethylphosphonate (205 mg, 1.4 mmol) in THF (1 ml) as added dropwise to a solution of potassium t-butoxide (1.4 ml, 1M $K^+$ $^-$OtBu in THF, 1.4 mmol) in THF (2.4 ml) at −78° C. The resulting yellow solution was stirred for ten minutes. The aldehyde 4 (394 mg, 1.05 mmol) was dissolved in THF (5 ml) and cooled to −78° C. The cooled aldehyde solution was quickly transferred to the flask containing the phosphonate using a short cannula. The flask that contained aldehyde was rinsed with THF (3 ml), cooled, and then added in the same manner. The reaction was stirred at −78° C. for about 12 hours and was allowed to warm to room temperature overnight. The reaction was quenched with saturated sodium bicarbonate solution and extracted with ether (4×25 ml). The ether layer was washed with brine, dried over $MgSO_4$, filtered, and concentrated in vacuo to give a crude solid. Silica gel chromatography using 15% ethyl acetate in hexanes gave the pure alkyne 15 as a white solid (380 mg, 97%, m.p. 173–175° C.).

Compound 15: $^1$H NMR (400 MHZ., $CDCl_3$): δ 3.94 (s, 4H), 2.45 (m, 1H-20), 2.02 (d, J=2 Hz., 1H-23), 1.21 (d, J=7 Hz., 3H-21), 0.81 (s, 3H-19), 0.68 (s, 3H-18). $^{13}$C NMR (100 MHZ., $CDCl_3$): δ 109.63, 89.68, 68.58, 64.35, 56.36, 55.59, 54.30, 43.90, 42.81, 39.46, 38.16, 36.23, 35.69, 35.61, 32.07, 31.36, 31.18, 28.74, 27.74, 27.45, 24.35, 21.51, 21.24, 12.61;

IR (KBr, $cm^{-1}$): 3257, 2104, 1255, 686;

MS (CI, isobutane): m/e (relative intensity): 371 ([M+H]$^+$, 100), 307 (20), 154 (82), 136 (72);

Anal. Calcd for $C_{25}H_{38}O_2$: C, 81.03; H, 10.34. Found: C, 80.85, H, 9.87.

11. Preparation of Compound 16

A solution of n-BuLi in hexanes (0.5 ml, 1.6 M, 0.81 mmol) was added dropwise to a solution of alkyne 15 (100 mg, 0.27 mmol) in THF (5 ml) at −78° C. The reaction was stirred for one hour, and boron trifluoride diethyl etherate (0.1 ml, 0.81 mmol) was added dropwise. After stirring for 15 minutes at −78° C., isobutyric anhydride (0.2 ml, 1.2 mmol) was added in one portion. The reaction was stirred at −78° C. for about 30 minutes and was quenched by adding 0.2 N NaOH solution. The reaction mixture was extracted with ether (3×10 ml), and the organic layer was washed with brine, dried over $MgSO_4$, filtered, and concentrated in vacuo to give a crude oil. Silica gel chromatography using 5% ethyl acetate in hexanes gave the pure propargyl ketone 16 as a thick oil (86 mg, 72%).

Compound 16: $^1$H NMR (400 MHZ., $CDCl_3$): δ 3.94 (s, 4H), 2.63 (m, 2H, H-20 & H-25), 1.95 (m, 1H), 1.83 (m, 1H), 1.26 (d, J=6.8 Hz., 3H-21), 1.18 (d, J=6.8 Hz., 6H, H-25 & H-26), 0.82 (s, 3H-19), 0.70 (s, 3H-18).

$^{13}$C NMR (100 MHZ., $CDCl_3$): δ 192.85, 109.59, 99.86, 80.62, 64.36, 56.16, 55.26, 54.28, 43.88, 43.33, 42.99, 39.33, 38.14, 36.23, 35.69, 35.62, 32.05, 31.35, 28.69, 28.18, 27.34, 24.39, 21.21, 20.64, 18.29, 12.78, 11.62. IR (KBr, $cm^{-1}$): 2206, 1675;

MS (CI, isobutane): m/e (relative intensity): 441 ([M+H]$^+$, 85), 125 (23), 99 (100), 77 (35);

Anal. Calcd for $C_{29}H_{44}O_3$: C, 79.04; H, 10.06; Found: C, 78.45, H, 9.57.

12. Preparation of Compound 17

A solution of propargyl ketone 16 (50 mg, 0.11 mmol) in THF (0.5 ml) was dried over 4 Å molecular sieves for two hours. The ketone solution was then added via a syringe to a solution of (S)-MeCBS (0.18 ml, 1.3 M in toluene, 0.23 mmol) in THF (0.5 ml) at room temperature. The resulting solution was cooled to −30° C., and a solution of boron methyl sulfide in THF (0.28 ml, 2M in THF, 0.57 mmol) was added dropwise over 5–10 minutes. The reaction was stirred at −30° C. for about an hour, at which time, the TLC indicated that the reaction was complete. The reaction was quenched by slowly adding methanol (1 ml). The solution was diluted with ether, washed with saturated ammonium chloride solution, followed by 5% sodium bicarbonate and then brine. The ether layer was dried over $MgSO_4$, filtered, and concentrated in vacuo. Silica gel chromatography using 20% ethyl acetate in hexanes gave the pure propargyl alcohol 17 as a white solid (36 mg, 72%).

Compound 17: $^1$H NMR (400 MHZ., $CDCl_3$): δ 4.15 (m, 1H-24), 3.94 (s, 4H), 2.48 (m, 1H-20), 1.19 (d, J=6.9 Hz., 3H-21), 0.98 (d, J=6.7 Hz., 3H) 0.96 (d, J=6.7 Hz., 3H), 0.81 (s, 3H-19), 0.67 (s, 3H-18).

$^{13}$C NMR (100 MHZ., $CDCl_3$): δ 109.38, 90.84, 80.16, 68.13, 64.09, 56.12, 55.68, 54.11, 43.67, 42.57, 39.22, 37.93, 36.00, 35.47, 35.39, 34.68, 31.85, 31.13, 28.52, 27.62, 27.32, 24.15, 21.41, 21.00, 18.16, 17.32, 12.50, 11.38. (NOTE: 77.00 ppm was used as reference);

IR (KBr, cm$^{-1}$): 3464, 2230.

13. Preparation of Compound 9

A solution of propargyl alcohol 17 (35 mg, 0.08 mmol) in ethyl acetate (3 ml) was treated with 10% palladium on carbon (20 mg, 0.02 mmol), sodium nitrite (~2–3 mg) and hydrogen (40 psig) on a Parr apparatus for 17 hours. The reaction was filtered through a pad of Celite® (SiO$_2$, available from Aldrich), and the filtrate was concentrated in vacuo. The crude solid was purified by silica gel column chromatography using 20% ethyl acetate in hexanes to provide the alcohol 9 (27 mg, 77%).

Compound 9: $^1$H NMR (250 MHZ., CDCl$_3$): δ 3.92 (s, 4H), 3.32 (m, 1H-24), 1.95 (m, 1H), 1.83 (m, 1H), 0.90 (d, J=6.8 Hz., 6H, H-25 & H-26), 0.80 (s, 3H-19), 0,65 (s, 3H-18). $^{13}$C NMR (400 MHz, DEPT, CDCl$_3$): δ 77.29 (C24-R).

14. Preparation of Epimeric Mixture of Compounds 17 and 18

A solution of n-BuLi in hexanes (0.2 ml, 1.6 M, 0.32 mmol) was added dropwise to a solution of alkyne 15 (40 mg, 0.11 mmol) in THF (2 ml) at −78° C. The reaction was stirred for 15 minutes and HMPT (0.2 ml, 1.1 mmol) was added. After stirring for another hour at −78° C., isobutyraldehyde (0.03 ml, 0.38 mmol) was added in one portion. The reaction was allowed to warm up to room temperature and was quenched by adding saturated ammonium chloride solution. The reaction mixture was extracted with ether (3×10 ml), and the organic layer was washed with brine, dried over MgSO$_4$, filtered, and concentrated in vacuo to give a crude oil. Silica gel column chromatography using 10% ethyl acetate in hexanes separated the unreacted starting material 15 from the product 17 and 18 (20 mg, 43%, m.p. 138–140° C.).

Mixture of compounds 17 and 18: $^1$H NMR (400 MHZ., CDCl$_3$): δ 4.15 (m, 1H-24), 3.94 (s, 4H), 2.48 (m, 1H-20), 1.19 (d, J=6.6 Hz., 3H-21), 0.98 (d, J=7.9 Hz., 3H) 0.96 (d, J=7.3 Hz., 3H), 0.81 (s, 3H-19), 0.68 (s, 3H-18).

$^{13}$C NMR (100 MHZ., CDCl$_3$): δ 109.63, 91.16, 80.28, 68.36, 64.35, 56.34, 55.87, 54.31, 43.90, 42.78, 39.44, 38.16, 36.23, 35.69, 35.61, 34.91, 32.08, 31.36, 28.74, 27.88, 27.59, 24.39, 21.65, 21.24, 18.41, 17.55, 12.75, 11.63; IR (KBr, cm$^{-1}$): 3464, 2229. MS (CI, isobutane): m/e (relative intensity): 443 ([M+H]$^+$, 90), 154 (17), 125 (22), 99 (100); Anal. Calcd for C$_{29}$H$_{46}$O$_3$: C, 78.68; H, 10.47; Found: C, 78.13, H, 10.02.

15. Preparation of Epimeric Mixture of Compounds 9 and 10

A solution of a mixture of propargyl alcohols 17 and 18 (20 mg, 0.045 mmol) in ethyl acetate (3 ml) was treated with 10% palladium on carbon (10 mg, 0.02 mmol), sodium nitrite (~1 mg) and hydrogen (40 psig) on a Parr apparatus for 4 hours. The reaction was filtered through a pad of Celite® (SiO$_2$, available from Aldrich), and the filtrate was concentrated in vacuo. The crude solid was purified by silica gel column chromatography using 20% ethyl acetate in hexanes to produce the mixture of alcohols 9 and 10 (16 mg, 80%).

Mixture of compounds 9 and 10: $^1$H NMR (250 MHZ., CDCl$_3$): δ 3.92 (s, 4H), 3.32 (m, 1H-24), 1.95 (m, 1H), 1.83 (m, 1H), 0.90 (d, J=6.8 Hz., 6H, H-25 & H-26), 0.80 (s, 3H-19), 0.65 (s, 3H-18). $^{13}$C NMR (400 MHz, DEPT, CDCl$_3$): δ 77.63, 77.29 (C24-S+R).

In the procedures noted above, note the discussion in the Seyferth, Colvin, Gilbert, Brown, and Parker articles. Each of these articles is discussed above in this patent application.

16. Alternate Method for Synthesis of Compound 22 (FIG. 15A)

A solution of compound 21 (19 g, 57 mmol, commercially available from Pharmacia or Upjohn), ethylene glycol (180 ml, 3.2 mol), and p-toluenesulfonic acid monohydrate (2.72 g, 14.3 mmol) in toluene (700 ml) was heated to reflux with removal of water for 25 hours. After cooling, saturated sodium bicarbonate (200 ml) was added, and the organic phase was washed with brine (2×100 ml) and dried over sodium sulfate. After removing solvent, the product was purified by flash chromatography (gradient elution with 0 to 40% ethyl acetate in hexane) and recrystallized (ethyl acetate in hexane-150 ml) to give compound 22 (15.98 g, 75%, mp 178–180° C.): $^1$H NMR (400 MHZ, CDCl$_3$): δ 5.36 (m, 1H), 3.95 (m, 4H), 3.64 (d of d, J=10.5 and 3.2 Hz, 1H), 3.37 (d of d, J=10.5 and 7.0 Hz, 1H), 2.59–2.55 (m, 1H), 2.12 (d of d, J=14.1 and 3.0 Hz, 1H), 2.0–1.0 (m, 19H), 1.06 (d, J=6.8 Hz, 3H), 1.04 (s, 3H), 0.71 (s, 3H); $^{13}$C NMR (400 MHZ, CDCl$_3$): δ 140.3, 122.3, 109.6,68.1,64.6, 64.4, 56.6, 52.5, 49.8,42.6, 41.9, 39.7, 38.9, 36.7, 36.5, 32.0, 31.8, 31.2, 27.9, 24.5, 21.2, 19.0, 16.9, 12.1; Anal. Calcd. for C$_{24}$H$_{38}$O$_3$: C, 76.96; H, 10.23. Found: C, 76.88; H, 9.67.

16b. Conditions for Synthesis of Compound 22

Chlorotrimethylsilane (3.0 ml, 24 mmol) was added to a mixture of compound 21 (1.78 g, 5.4 mmol) and ethylene glycol (25 ml). After 27 hours at room temp, the reaction mixture was treated with 5% sodium bicarbonate solution (50 ml), extracted with ethyl acetate (3×70 ml), washed with brine (5×15 ml), water (15 ml), and dried over magnesium sulfate. After removing the solvent, the product was recrystallized from ethanol (25 ml) to give compound 22 (1.41 g, 2 crops, 70%, mp 180–182° C.).

17. Synthesis of Compound 23

A mixture of compound 22 (4.2 g, 11.2 mmol), imidazole (1.53 g, 22.47 mmol), 4-dimethylaminopyridine (192 mg, 1.57 mmol), and tert-butyldimethylsilyl chloride (2.61 g, 17.3 mmol) in anhydrous dimethylformamide (60 ml) was stirred for 4 hours at room temperature, and then diluted with ether (150 ml) and methylene chloride (50 ml), washed with water (3×50 ml), and dried over sodium sulfate. After removing the solvent, the product was crystallized from ethyl acetate and hexane (100 ml) to yield pure compound 23 (5.41 g, 98%, mp 131–133° C.): $^1$H NMR (400 MHZ, CDCl$_3$): δ 5.35 (m, 1H), 3.95 (m, 4H), 3.59 (d of d, J=9.6 and 3.2 Hz, 1H), 3.23 (br t, J=9 Hz, 1H), 2.59–2.55 (m, 1H), 2.12 (d of d, J=14.2 and 2.5, 1H), 2.1–1.0 (m, 19H), 1.03 (s, 3H), 0.99 (d, J=6.2 Hz, 3H), 0.89 (s, 9H), 0.69 (s, 3H), 0.03 (s, 6H); Anal. Calcd. for C$_{30}$H$_{52}$O$_3$Si: C, 73.71; H, 10.72. Found: C, 73.28; H, 10.10.

18. Synthesis of Compound 24

A solution of compound 23 (3.42 g, 7.0 mmol), chromium hexacarbonyl (420 mg, 1.9 mmol), and 90% tert-butyl hydroperoxide (2.2 ml, 19.8 mmol) in acetonitrile (100 ml) was heated to reflux for 20 hours. After cooling, the mixture was diluted with ether (150 ml), washed with brine (3×30 ml), and dried over sodium sulfate. After evaporation, the product was purified by flash chromatography (gradient elution with 0 to 30% ethyl acetate in hexane) to produce starting material (compound 23, 510 mg) and compound 24 (1.53 g, 51% based on recovered starting material, mp 147–149° C.): $^1$H NMR (400 MHZ, CDCl$_3$): δ 5.63 (s, 1H), 3.94 (m, 4H), 3.57 (m, 1H), 3.22 (t, J=8.4 Hz, 1H), 2.39 (br d, J=7 Hz, 1H), 2.4–1.0 (m, 18H), 1.18 (s, 3H), 0.97 (d, J=6.2 Hz, 3H), 0.86 (s, 9H), 0.67 (s, 3H), 0.00 (s, 6H); $^{13}$C NMR (400 MHZ, CDCl$_3$): δ 201.9, 164.6, 126.8, 109.0, 68.0, 64.7, 64.6, 51.4, 49.9, 49.7, 45.5, 43.4, 41.9, 39.1, 38.7, 38.6, 38.4, 35.8, 31.2, 28.2, 26.6,26.1, 21.3, 18.5, 17.2, 17.1, 12.2, −5.2; MS (+FAB): 503.3 (M+1).

19. Alternative Synthesis of Compound 24

A mixture of compound 23 (489 mg, 1 mmol), N-hydroxyphthalimide (326 mg, 2 mmol), and benzoyl peroxide (10 mg, 0.008 mmol) in n-butyl acetate (50 ml) was heated at 110° C. and treated with air for 6 hours. The solvent was evaporated, and the residue was treated with dichloromethane (50 ml) and filtered. After washing the recovered N-hydroxyphthalimide (266 mg) with dichloromethane, the filtrate was evaporated, and the residue was dissolved in 5 ml of pyridine at 50° C., cooled to 5–10° C., treated with 0.5 ml (5.3 mmol) of acetic anhydride, and left at room temperature overnight. The solvent was evaporated, and the residue dissolved in 25% ethyl acetate and purified by flash chromatography (2.5 cm diameter, gradient elution with 0 to 25% ethyl acetate in hexane) to produce pure compound 24 (398 mg, 77%).

20. Synthesis of Compound 25

Hydrogenation of a solution of compound 24 (360 mg, 0.715 mmol) in ethyl acetate (25 ml) and ethanol (15 ml) was performed with 10% palladium on carbon (360 mg) at 40 psi of hydrogen on a Parr shaker. After 5 hours, the reaction mixture was filtered through Celite® ($SiO_2$, available from Aldrich), evaporated, and concentrated under vacuum overnight to yield compound 25 (350 mg, 97%), which was homogenous by TLC: $^1$H NMR (400 MHZ, $CDCl_3$): δ 3.88 (m, 4H), 3.54 (d of d, J=9 and 3 Hz, 1H), 3.22 (t, J=9 Hz, 1H), 2.3–1.0 (m, 22H), 1.05 (s, 3H), 0.95 (d, J=6.6 Hz, 3H), 0.85 (s, 9H), 0.63 (s, 3H), 0.01 (s, 6H); $^{13}$C NMR (400 MHZ, $CDCl_3$): δ 211.8, 108.8, 67.9, 64.4, 64.3, 55.0, 51.6, 50.1, 48.7, 45.9, 45.7, 42.7, 39.0, 38.7, 37.9, 36.0, 35.2, 31.2, 28.0, 26.1, 25.2, 21.9, 18.5, 17.1, 12.3, 11.1, −5.2; MS (+FAB): 505.3 (M+1); Anal. Calcd. for $C_{30}H_{52}O_4Si$: C, 71.38; H, 10.38. Found: C, 71.57; H, 10.16.

21. Synthesis of Compound 26

1 M K-Selectride® (potassium tri-sec-butylborohydride from Aldrich) in THF (8.5 ml, 8.5 mmol) was added dropwise to a solution of compound 25 (800 mg, 1.58 mmol) in tetrahydrofuran (35 ml) at −50° C. The reaction mixture was stirred for 5 hours and then quenched by the careful addition of 30% hydrogen peroxide (10 ml) and saturated sodium bicarbonate (20 ml). The aqueous layer was extracted with ether (3×50 ml), and the combined organic layers were washed with saturated sodium bicarbonate (2×20 ml), water (20 ml), and brine (20 ml). After drying, the solvent was removed, and the product was purified by flash chromatography (gradient elution with 0 to 30% ethyl acetate in hexane) to produce compound 26 (645 mg, 80%, mp 174–175° C.): $^1$H NMR (400 MHZ, $CDCl_3$): δ 3.93 (s, 4H) 3.82 (br s, 1H), 3.58 (br d, J=8 Hz, 1H), 3.25 (br t, J=8 Hz, 1H), 2.0–1.0 (m, 22H), 0.99 (d, J=6.3 Hz, 3H), 0.89 (s, 9H), 0.82 (s, 31), 0.67 (s, 3H), 0.03 (s, 6H); $^{13}$C NMR (400 MHZ, $CDCl_3$): δ 109.4, 68.1, 68.0, 64.4, 52.8, 50.5, 45.8, 42.9, 39.7, 39.5, 39.3, 37.7, 36.5, 36.4, 35.9, 35.8, 31.4, 27.9, 26.2, 24.0, 21.1, 18.6, 17.1, 12.1, 10.6, −5.2.

22. Synthesis of Compound 27

A solution of compound 26 (11.88 g, 23.4 mmol) in anhydrous pyridine (110 ml) under nitrogen was treated with 4-dimethylaminopyridine (3.43 g, 28.1 mmol) and benzoyl chloride (5.5 ml, 47.4 mmol) at room temperature, and then heated at reflux for 22 hours. The cooled reaction mixture was poured into saturated sodium bicarbonate (500 ml) and extracted with ethyl acetate (200 ml). The aqueous phase was extracted with more ethyl acetate (3×100 ml), and the combined organic layers were washed with saturated sodium bicarbonate (3×50 ml) and brine (2×50 ml), dried over sodium sulfate, and then concentrated to give crude product. The solid was recrystallized from ethyl acetate in methanol to obtain pure compound 27 (13.8 g, 96%, mp 180–183° C.): $^1$H NMR (400 MHZ, $CDCl_3$): δ 8.07 (d, J=7 Hz, 2H), 7.59 (t, J=7 Hz, 1H), 7.48 (t, J=7 Hz, 2H), 5.15 (br s, 1H), 3.88 (m, 4H), 3.55 (d of d, J=9.5 and 3.4 Hz, 1H), 3.15 (t, J=9.5 Hz, 1H), 2.1–1.0 (m, 22H), 0.98 (d, J=6.8 Hz, 3H), 0.88 (s, 3H), 0.86 (s, 9H), 0.69 (s, 3H), 0.01 (s, 6H); $^{13}$C NMR (400 MHZ, $CDCl_3$): δ 166.2, 133.0, 131.2, 129.8, 128.6, 109.2, 72.2, 68.0, 64.4, 52.9, 50.7, 47.4, 43.1, 39.6, 39.3, 38.8, 37.5, 37.4, 35.9, 35.7, 33.5, 31.4, 27.7, 26.2, 24.0, 21.3, 18.6, 17.0, 12.1, 10.7, −5.2; Anal. Calcd. for $C_{37}H_{58}O_5Si \cdot 0.2H_2O$: C, 72.31; H, 9.58. Found: C, 72.13; H, 9.26.

23. Synthesis of Compound 28

Tetrabutylammonium fluoride (1 M, 27 ml, 27 mmol) in tetrahydrofuran was added to a solution of compound 27 (10.8 g, 17.7 mmol) in anhydrous tetrahydrofuran (90 ml) at room temperature, and then the reaction was heated to reflux for 6.5 hours. After cooling, the mixture was diluted with ethyl acetate (200 ml) and washed with water (60 ml), brine (3×60 ml), and dried over sodium sulfate. After removing solvent, the product was purified by flash chromatography (gradient elution with 0 to 25% ethyl acetate in hexane) to yield compound 28 (8.14 g, 93%, mp 117–119° C.): $^1$H NMR (400 MHZ, $CDCl_3$): δ 8.06 (d, J=8 Hz, 2H), 7.59 (t, J=7 Hz, 1H), 7.48 (t, J=8 Hz, 2H), 5.16 (br s, 1H), 3.88 (m, 4H), 3.58 (d of d, J=10.5 and 3.3 Hz, 1H), 3.33 (d of d, J=11 and 6.5 Hz, 1H), 2.1–1.1 (m, 22H), 1.04 (d, J=6.9 Hz, 3H), 0.89 (s, 3H), 0.70 (s, 3H); $^{13}$C NMR (400 MHZ, $CDCl_3$): δ 166.2, 133.0, 131.1, 129.8, 128.6, 109.2, 72.0, 68.0, 64.4, 64.3, 52.4, 50.7, 47.4, 43.0, 39.5, 38.8, 37.5, 37.4, 35.9, 35.6, 33.4, 31.4, 27.7, 23.9, 21.3, 16.9, 14.4, 12.0, 10.7; $C_{31}H_{44}O_5 \cdot 0.2H_2O$: C, 74.42; H, 8.95. Found: C, 74.47; H, 8.79.

24. Alternate Method for Synthesis of Compound 29

A solution of dimethylsulfoxide (3.0 ml, 42 mmol) in dichloromethane (15 ml) was added to a cold (−70 to −60° C.) 2 M solution of oxalyl chloride in dichloromethane (9 ml, 18 mmol) under nitrogen. After 10 minutes, a solution of compound 28 (6.0 g, 12.1 mmol) in dichloromethane (55 ml) was added dropwise. After stirring for 1 hour, triethylamine (9 ml, 64 mmol) was added, and the reaction was allowed to warm to room temperature. Water (120 ml) was added, and the aqueous phase was extracted with dichloromethane (3×100 ml), which was in turn washed with brine (3×100 ml) and water (90 ml), and dried over sodium sulfate. After evaporation, clean product 29 was obtained, without further purification (6.0 g, 100%, mp 166–168° C.): $^1$H NMR (400 MHZ, $CDCl_3$): δ 9.52 (d, J=2.4 Hz, 1H), 8.06 (d, J=7 Hz, 2H), 7.60 (t, J=7 Hz, 1H), 7.49 (t, J=7 Hz, 2H), 5.17 (m, 1H), 3.88 (m, 4H), 2.35 (m, 1H), 2.0–1.1 (m, 21 H), 1.11 (d, J=6.9 Hz, 3H), 0.89 (s, 3H), 0.73 (s, 3H); $^{13}$C NMR (400 MHZ, $CDCl_3$): δ 205.1, 166.1, 133.0, 131.0, 129.8, 128.7, 109.1, 71.9, 64.4, 64.3, 51.1, 50.2, 49.6, 47.4, 43.5, 39.4, 38.8, 37.5, 37.4, 35.9, 35.7, 33.4, 31.4, 27.1, 24.2, 21.2, 13.6, 12.3, 10.7.

24b. Conditions for Synthesis of Compound 29

A solution of potassium bromide (1.44 g, 12.0 mmol) in water (60 ml) was added to a solution of alcohol 28 (60.0 g, 0.12 mol) and 2,2,6,6-tetramethyl-1-piperidine oxide (TEMPO) (360 mg, 2.4 mmol) in dichloromethane (600 ml). The mixture was cooled in an ice-water bath and stirred vigorously. A sodium hypochlorite solution was prepared by diluting commercial Clorox bleach (5.28%) with an equal volume of water to become 2.64% (0.39 M, 324 ml, 0.12 mol, pH 11.3). This Clorox solution was adjusted to pH 9.5 by adding sodium bicarbonate powder while keeping the temperature between 10–15° C. The sodium hypochlorite solution was added dropwise to the mixture above, and the reaction mixture was stirred for 30 minutes. The aqueous layer was separated and extracted with dichloromethane (2×100 ml). The combined dichloromethane extracts were washed with water (2×150 ml) and brine (50 ml), dried over magnesium sulfate, and evaporated. The residue (69.1 g) was triturated in refluxing hexane (200 ml) for 30 minutes and cooled to room temperature and then in the refrigerator for 1 hour. The white powder was collected by filtration, washed with hexane (2×40 ml) and dried (50° C., 0.1 mm, 5 hours) to give pure aldehyde 29 (47.5 g, 79%, mp 164–166° C.). If full strenght bleach is used, the reaction fails in that aldehyde 29 is obtained as a mixture of C-20 isomers.

25. Preparation of Compound 30 (FIG. 15B)

A solution of 1-bromo-3-methyl-2-butanone (Note M. Gaudry and A. Marquet, "1-Bromo-3-Methyl-2-Butanone," *Organic Synthesis*, Vol VI, pp. 193–195, which article is entirely incorporated herein by reference) (10 g, 60 mmol) and triethyl phosphite (10.3 ml, 60 mmol) was heated to 120° C. under nitrogen for 3 hours with the removal of ethyl bromide by distillation. The cooled reaction mixture was placed under high vacuum and then distilled to produce compound 30 (8.0 g, 60%, bp 127–130° C., 3 mm) (procedure from the thesis of Phu H. Le, UCSD, 1983, T. C. McMorris): $^1$H NMR (400 MHZ, CDCl$_3$): δ 4.15 (p, J=7 Hz, 4l), 3.14 (d, J=22.5 Hz, 2H), 2.87 (heptet, 7 Hz, 1H), 1.34 (t, J=7 Hz, 6H), 1.13 (d, J=7 Hz, 6H).

26. Preparation of Compound 32

Sodium hydride (60%, 44 mg, 1.1 mmol) was washed with heptane (2 ml) and hexane (2×2 ml), and evaporated with a nitrogen flow. Anhydrous tetrahydrofuran (2 ml), compound 30 (0.34 ml, 1.5 mmol), and a solution of compound 29 (486 mg, 0.982 mmol) in tetrahydrofuran (3 ml) were added. The reaction mixture was heated to reflux for 1 hour, cooled to room temperature, and treated with water (25 ml). The aqueous layer was extracted with ethyl acetate (3×50 ml), which was in turn washed with brine (3×50 ml), water (2×50 ml), and dried over sodium sulfate. After removing solvent, the product was dissolved in methanol (5 ml) containing 4 drops of pyridine, and dropped into water (100 ml) with shaking. The resulting solid was filtered, washed with water (3×20 ml), and dried under vacuum at 50° C. to give pure compound 32 (499 mg, 90%, mp 85–121° C.): $^1$H NMR (400 MHZ, CDCl$_3$): δ 8.06 (d, J=7.4 Hz, 2H), 7.59 (t, J=7.1 Hz, 1H), 7.48 (t, J=7.4 Hz, 2H), 6.65 (d of d, J=15.6 and 9 Hz, 1H), 6.02 (d, J=15.6 Hz, 1H), 5.15 (br s, 1H), 3.88 (br s, 4H), 2.80 (hept, J=6.7 Hz, 1H), 2.25 (m, 1H), 2.0–1.0 (m, 21H), 1.08 (d, 3H), 1.06 (d, J=6.9 Hz, 6H), 0.89 (s, 3H), 0.72 (s, 3H); $^{13}$C NMR (400 MHZ, CDCl$_3$): δ 204.7, 166.1, 152.5, 133.0, 131.1, 129.8, 128.6, 126.5, 109.2, 72.0, 64.4, 64.3, 55.0, 50.8, 47.4, 43.2, 40.1, 39.5, 38.8, 38.3, 37.5, 37.4, 35.9, 35.7, 33.4, 31.4, 28.2, 23.8, 21.2, 19.5, 18.8, 18.6, 13.6, 12.2, 10.7; MS (+FAB): 563.3 (M+1); Anal. Calcd. for C$_{36}$H$_{50}$O$_5$-0.2H$_2$O: C, 76.34; H, 8.97. Found: C, 76.26; H, 9.13.

In this process, the procedure of T. C. McMorris, et al., "Synthesis of Dehydro-Oogoniol, a Female-Activating Hormone of ACHLYA: The Progesterone Route," *Steroids*, 1989, Vol. 53, pp. 345–361 was followed. This article is entirely incorporated herein by reference.

27. Preparation of Compound 33

An argon blanketed flask was charged with 1 M R-MeCBS (from Callery) in toluene (0.92 ml, 0.92 mmol) and 1 M borane-tetrahydrofuran complex in tetrahydrofuran (2.3 ml, 2.3 mmol). The reaction mixture was stirred at room temperature for 2 hours, cooled to −20° C., and treated with a solution of compound 32 (520 mg, 0.92 mmol) in anhydrous toluene (15 ml) over 1.5 hours. After an additional hour, the reaction mixture was treated with solid ammonium chloride and water (2 ml), warmed to room temperature, diluted with more water (20 ml), and extracted into toluene (2×80 ml). The toluene layer was washed with saturated ammonium chloride (3×50 ml), dried with magnesium sulfate, and evaporated to give a solid, which was recrystallized from ethyl acetate in hexane to give compound 33 in two crops (491 mg, 94%, mp 196–199° C.): $^1$H NMR (400 MHZ, CDCl$_3$): δ 8.06 (d, J=7 Hz, 2H), 7.59 (t, J=7 Hz, 1H), 7.48 (t, J=7 Hz, 2H), 5.35 (m, 2H), 5.16 (br s, 1H), 3.88 (br s, 4H), 3.67 (t, J=6.2, 1H), 2.1–10 (m, 23H), 1.03 (d, J=6.3 Hz, 3H), 0.89 (m, 6H), 0.82 (d, J=6.6 Hz, 3H), 0.70 (s, 3H); $^{13}$C MNR (400 MHZ, CDCl$_3$): δ 166.1, 139.8, 133.0, 131.2, 129.9, 128.8, 128.6, 109.2, 78.8, 72.0, 64.4, 64.3, 55.6, 51.0, 47.4, 42.9, 40.2, 39.6, 38.8, 37.5, 37.4, 35.9, 35.7, 34.1, 33.5, 31.5, 28.8, 23.9, 21.3, 20.6, 18.6, 18.4, 12.2, 10.7; MS (+FAB): 565.3 (M+1); Anal. Calcd. for C$_{36}$H$_{52}$O$_5$-0.2H$_2$O: C, 76.07; H, 9.29. Found: C, 75.93; H, 9.14.

28. Alternate Method for Synthesis of Compound 34

A solution of compound 33 (2.7 g, 4.8 mmol) in tetrahydrofuran (30 ml) was treated with sodium nitrite (89 mg, 1.3 mmol), 20% palladium hydroxide on carbon (0.5 g, Pearlman's catalyst), and 40 psi of hydrogen on a Parr apparatus. After 16 hours, the reaction mixture was filtered through Celite® (SiO$_2$, available from Aldrich) and concentrated to obtain crude material, which was recrystallized from dichloromefiane in hexane (15 ml) to produce pure compound 34 (2.13 g, 78%, mp 205–208° C.): $^1$H NMR (400 MHZ, CDCl$_3$): δ 8.08 (d, J=7.5 Hz, 2H), 7.60 (t, J=7.5 Hz, 1H), 7.49 (t, J=7.5 Hz, 2H), 5.16 (br s, 1H), 3.88 (m, 4H), 3.28 (m, 1H), 2.0–1.0 (m, 27H), 0.93–0.90 (m, 9H), 0.89 (s, 3H), 0.69 (s, 3H); $^{13}$C NMR (400 MHZ, CDCl$_3$): δ 166.2, 133.0, 131.2, 129.9, 128.6, 109.2, 77.0, 72.1, 64.4, 64.3, 56.0, 50.8, 47.3, 42.9, 39.6, 38.7, 37.5, 37.3, 35.8, 35.6, 33.6, 33.4, 32.1, 31.4, 30.7, 28.2, 23.8, 21.2, 19.1, 18.8, 17.4, 11.9, 10.7; MS (+FAB): 567.5 (M+1); Anal. Calcd. for C$_{36}$H$_{54}$O$_5$-0.3H$_2$O: C, 75.56; H, 9.62. Found: C, 75.29; H, 9.04.

28b. Conditions for Synthesis of Compound 34

A mixture of compound 33 (100 mg, 0.18 mmol), 10% platinum on carbon (5 mg), triethylamine (5 drops) in ethyl acetate (15 ml) was treated with a hydrogen balloon for 22 hours. After filtration through Celite®, the solution was evaporated and recrystallized from methanol (1 ml) and water (few drops) to afford approx. 95% pure compound 34 (81 mg, 80%).

29. Preparation of Compound 35

A solution of compound 34 (210 mg, 0.37 mmol) in 90% acetone/water (16 ml) was treated with pyridinium p-toluenesulfonate (73 mg, 0.29 mmol) and heated to reflux for 12 hours. The reaction mixture was extracted with ethyl acetate (25 ml), and this material subsequently was washed with water (2×25 ml), dried over sodium sulfate, and evaporated to yield compound 35 (170 mg, 88%): $^1$H NMR (400 MHZ, CDCl$_3$): δ 8.03 (d, J=7 Hz, 2H), 7.60 (t, J=7 Hz, 1H), 7.48 (t, J=7 Hz, 2H), 5.20 (br s, 1H), 3.28 (m, 1H), 2.5–1.0 (m, 27H), 1.09 (s, 3H), 0.93 (d, J=6.3 Hz, 3H), 0.90 (d, J=7 Hz, 3H), 0.89 (d, J=7 Hz, 3H), 0.72 (s, 3H); $^{13}$C NMR (400 MHZ, CDCl$_3$): δ 211.5, 165.9, 133.2, 130.9, 129.8, 128.7, 71.5, 56.1, 50.8, 47.2, 44.1, 42.9, 40.6, 39.6, 38.8, 38.4, 38.3, 35.8, 33.7, 32.1, 30.7, 28.3, 23.8, 21.6, 19.1, 18.8, 17.4, 12.0, 10.9; Anal. Calcd. for C$_{34}$H$_{50}$O$_4$-0.3H$_2$O: C, 77.32; H, 9.66; Found: C, 77.06; H, 9.23.

30. Alternative Method for Synthesis of Compound 36

Sulfur trioxide-pyridine complex (610 mg, 3.8 mmol) and compound 35 (830 mg, 1.59 mmol) were dissolved in anhydrous pyridine (7 ml) under nitrogen. The reaction mixture was heated to 80° C. for 3 hours, evaporated, dissolved in dichloromethane (400 ml), washed with water (100 ml) and brine (2×100 ml), dried, and evaporated to obtain compound 36 (1.06 g, 98%) as the pyridine salt: $^1$H NMR (400 MHZ, CDCl$_3$): δ 8.91 (m, 2H), 8.36 (t, J=7 Hz, 1H), 7.99 (d, J=7 Hz, 2H), 7.91 (m, 2H), 7.57 (t, J=7 Hz, 1H), 7.46 (t, J=7 Hz, 2H), 5.15 (br s, 1H), 4.26 (m, 1H), 2.4–1.0 (m, 27H), 1.06 (s, 3H), 0.88 (m, 9H), 0.66 (s, 3H); $^{13}$C NMR (400 MHZ, CDCl$_3$): δ 211.5, 165.9, 145.4, 142.7, 133.2, 130.7, 129.6, 128.7, 127.2, 85.1, 71.4, 56.0, 50.7, 47.1, 44.0, 42.8, 40.5, 39.4, 38.6, 38.3, 38.2, 35.7, 33.6, 31.1, 30.9, 28.0, 26.8, 23.7, 21.4, 18.7, 18.3, 17.8, 11.9, 10.8; MS (-LD): 606.

30b. Conditions for Synthesis of Compound 36

A mixture of compound 34 (17.6 g, 31 mmol), acetone (880 ml), and Amberlyst® 15 ion-exchange resin (7.1 g, Aldrich 21, 638-0) was stirred at room temperature for 3 hours. At this time HPLC showed 3.5% unconverted compound 34. After filtration and washing with acetone (3×25 ml), pyridine (2 ml) was added to the filtrate. After evaporation of the solvent in vacuo, pyridine (100 ml) was added. Evaporation in vacuo was continued until another 75 ml of distillate was obtained. Pyridine (500 ml) was added to the residue, and this solution was used without further purification. The solution of compound 35 was stirred at room temperature under nitrogen. Sulfur trioxide-pyridine complex (10.0 g, 62.8 mmol) was added in one portion, and the mixture was warmed to 80° C. for 45 minutes, after which TLC showed completion of the reaction. The solvent was removed in vacuo, and toluene (100 ml) was added to the residue. Again, the solvent was removed in vacuo. Ethyl acetate (200 ml) was added to the residue at 50° C., and the suspension was cooled to approximately 25° C. and filtered. The flask and the filter cake were washed with ethyl acetate (50 ml). A mixture of 25% sodium chloride (25 ml) and water (25 ml) was added to the slightly turbid filtrate at 20° C. After a few minutes, a thick suspension was obtained. t-Butyl methyl ether (500 ml) was added, and the suspension was cooled to 0° C., filtered, and washed with water (50 ml) and t-BuOMe (50 ml). The solid was dried (50° C., 2 mm) to yield compound 36 as the sodium salt (17.3 g, 89% from compound 34).

31. Alternate Method for Synthesis of Compound 37

A 0.5 M sodium methoxide solution (10 ml, 5 mmol) was added to compound 36 (600 mg, 0.88 mmol) under nitrogen, and the reaction was brought to reflux for 3 hours. After leaving this mixture overnight at room temperature, the reaction was again heated at reflux for 5 hours. After evaporation, the residue was suspended in water (25 ml), neutralized (pH 7) with 1.5% trifluoroacetic acid, treated with brine, and extracted with methyl t-butyl ether. The aqueous layer was acidified to pH 2, saturated with sodium chloride, and extracted with tetrahydrofuran (6×100 ml, this entire volume is probably not necessary). The organic layers were dried with sodium sulfate, filtered, and evaporated to produce an oil, which was triturated with methyl t-butyl ether and collected by filtration to yield compound 37 (330 mg, 75%, mp 150–151° C.): $^1$H NMR (400 MHZ, THF-D$_8$): δ 4.11 (br q, 1H), 3.71 (br s, 1H), 2.4–1.0 (m, 27H), 1.02 (s, 3H), 0.94 (d, J=6.5 Hz, 3H), 0.92 (d, J=6.8 Hz, 3H), 0.89 (d, J=6.7 Hz, 3H), 0.70 (s, 3H); $^{13}$C NMR (400 MHZ, THF-D$_8$): δ 209.4, 84.3, 57.3, 51.5, 46.3, 45.1, 43.4, 41.0, 40.9, 40.2, 39.5, 38.8, 38.5, 37.1, 36.7, 32.2, 31.6, 29.2, 27.9, 26.024.6, 22.3, 19.4, 18.6, 18.5, 12.5, 10.7; MS (-FAB): 497.1 (M−1).

31b. Conditions for Synthesis of Compound 37

A mixture of compound 36 (17.2 g, 27.5 mmol) in 1 M potassium hydroxide solution (150 ml, 150 mmol) in methanol under nitrogen was refluxed overnight. After evaporation of the solvent in vacuo, water (125 ml) and dichloromethane (125 ml) were added, and the suspension was cooled to 0° C. After filtration, the solid was washed with water (3×30 ml) and dichloromethane (2×25 ml) and dried overnight (50° C., 2 mm) to yield crude compound 37 as the potassium salt (12.5 g, 85%). Crude compound 37 (12.5 g, 23.3 mmol) was dissolved in a warm mixture of methanol (200 ml) and triethylamine (10 ml) and filtered to remove insolubles. The filtrate was concentrated on a rotary evaporator to approximately 75 ml, and t-BuOMe (100 ml) was added. After cooling to 0° C., the suspension was filtered, washed with t-BuOMe (30 ml), and dried to give the potassium salt of compound 37 (10.4 g, 70%, mp 165–174° C.) as a white solid: $^1$H NMR (400 MHZ, DMSO-D$_6$): ä 4.16 (m, 1H), 3.78 (br q, J=5 Hz, 1H), 3.61 (m, 1H), 2.5–1.0 (m, 27H), 0.94 (s, 3H), 0.86 (d, J=6 Hz, 3H), 0.81 (d, J=7 Hz, 3H), 0.79 (d, J=7 Hz, 3H), 0.63 (s, 3H); Anal. Calcd. for C$_{27}$H$_{45}$O$_6$S-0.77K-0.1Na-0.2H$_2$O: C, 60.76; H, 8.57; H$_2$O, 0.68; K, 5.64; Na, 0.43. Found: C, 60.12; H, 8.21; H$_2$O, 0.66; K, 5.61; Na, 0.44; IR (KRr, cm$^{-1}$): 3436, 2928, 1708, 1470, 1390, 1208, 1051, 1038, 950, 812.

32. Preparation of Compound 38 (which corresponds to Compound 1436)

3 Å molecular sieves (1 gram) were added to the clear colorless solution of compound 37 (16 mg, 0.032 mmol) and spermine (20 mg, 0.1 mmol, commercially available from Aldrich) in anhydrous methanol (3 ml). The reaction was stirred at room temperature under nitrogen for 12 hours, cooled to −78° C., and treated dropwise with sodium borohydride (1 pellet, 0.4 g, 10 mmol) in methanol (10 ml). This reaction mixture was stirred for 3 hours, treated with a mixture of water and methanol (10 ml each), warmed to room temperature, and then treated with 0.78% trifluoroacetic acid (TFA) solution until its pH reached the range of 4–5. The resulting mixture was filtered through a thin pad of Celite®, and the Celite® was washed with methanol and water (100 ml). Celite® is SiO$_2$ that is commercially available from Aldrich. The combined acidic washes were concentrated in vacuo at room temperature and then freeze-dried overnight to give a white solid. The Celite® cake was then washed with isopropyl amine/methanol/water (140 ml of 1:3:3), and the basic portion was evaporated to reduce its volume. This material was freeze-dried overnight to give a light brown solid. Both washes contained compound 38, so they were combined and acidified to a pH of 3 with 0.78% TFA, filtered, and loaded onto a small HPLC column (1 cm diameter, see below). The reaction product was compound 38 (12.2 mg, 36%): $^1$H NMR (400 MHZ, D$_2$O): δ 4.14 (m, 1H), 3.83 (m, 1H), 3.2–3.0 (m, 13H), 2.1–1.0 (m, 35H), 0.92 (m, 9H), 0.82 (s, 3H), 0.67 (s, 3H); $^{13}$C NMR (400 MHZ, D$_2$O): δ 87.2, 68.0, 57.9, 56.0, 50.5, 47.4, 45.6, 44.9, 42.8, 41.9, 39.7, 37.5, 36.9, 36.7, 36.0, 35.8, 31.5, 31.1, 30.6, 28.3, 27.1, 24.8, 24.1, 23.6, 23.4, 23.1, 21.4, 19.2, 17.7, 12.1, 11.2; MS (-LD): 684 (M−1); Anal. Calcd. for C$_{37}$H$_{72}$N$_4$O$_5$S-3TFA-2H$_2$O: C, 48.58; H, 7.49; F, 16.08; N, 5.27; S, 3.02. Found: C, 48.49; H, 7.40; F, 16.16; N, 5.31; S, 3.05.

33. Purification of Compound 38 by HPLC

The crude material was dissolved in water (50 ml), cooled in an ice bath, and acidified with 1.5% TFA in water until its pH was 3. Initially, it was observed that one obtains a suspension as the pH drops, and then a solution is obtained at lower pH. This solution was loaded onto a Rainin reverse phase HPLC system (2.14 cm diameter, C18, 100 Å, 8 μm) and eluted with A (water with 0.1% TFA) and B (acetonitrile with 0.1% TFA). The HPLC program was as follows: 10 min (0–10% B), 60 min (10–45% B), 10 min (45–80% B), 10 min (80% B). Pure product eluted in the 33 to 55 minute fractions, as determined by TLC ($r_f$: 0.1–0.2 in 6/3/1 $CH_2Cl_2$/MeOH/$NH_4OH$)(should evaporate plates under vacuum before eluting, and observe with ninhydrin stain after eluting), which was lyophilized to produce 1.20 grams of compound 1436 as a white powder (70%); $C_{37}H_{72}N_4O_5S$-3TFA-2.5$H_2O$, FW 1072.18).

34. Allylic Oxidation of Stigmasterol (FIG. 16B) Stigmasterol (compound 50, 150 g, 363 mmol) (obtainable from Aldrich) and N-hydroxypthalimide (60 g, 368 mmol) were added to a 3000 ml 3 neck round bottom flask. A 50/50 mixture of ethyl acetate/acetone (approximately 2500 ml) was added to the flask. The flask was equipped with a glass fritted air inlet and condenser and warmed to approximately 55° C. with magnetic stirring. As the solution warmed, the stigmasterol and N-hydroxypthalimide dissolved. Dibenzoyl peroxide (approximately 250 mg) was then added to the reaction. Air was vigorously bubbled into the reaction with vigorous magnetic stirring, and the temperature of the reaction was maintained at 50–55° C. throughout the course of the reaction. Additional 50/50 ethyl acetate/acetone solvent was added to the reaction as needed to replenish that which was lost due to air flow through the system. The reaction was followed by TLC on silica gel (40% ethyl acetate in hexane) and judged to be complete after 48 hours. The reaction was worked up by adding the solution to cyclohexane (1000 ml) and allowing it to cool. The N-hydroxypthalimide was filtered off, and the remainder was removed by repetitive sodium carbonate washings until no orange coloration was observed. The organic layers were washed with brine and dried over $MgSO_4$. The solvent was removed in vacuo, and the sterol was dissolved in pyridine (500 ml). The pyridine solution was cooled to 0–4° C., and $CuCl_2$ (1 g) was added. The solution was stirred overnight, allowing the solution to warm to room temperature as the ice melted. The pyridine solution was then poured over an ice/water slurry (4000 ml), and the sterol precipitated. This solid was filtered, washed with 0.1 N HCl solution and distilled water, and then recrystallized from methanol (2x) to yield compound 60 (127 g, 298 mmol, 82%): mp 144° C.; $^1$H NMR (200 MHZ, $CDCl_3$): δ 5.71 (s, 1H), 5.26–4.95 (m, 2H), 3.69 (m, 1H), 1.20 (s, 3H), 1.02 (d, J=6.5 Hz, 3H), 0.86–0.78 (m, 9H), 0.70 (s, 3H); $^{13}$C NMR (200 MHZ, $CDCl_3$): δ 202.5, 165.8, 137.9, 129.3, 125.6, 70.0, 54.4, 51.0, 49.8, 49.7, 45.2, 42.8, 41.6, 40.1, 38.4, 38.1, 36.2, 31.7, 30.8, 28.8, 26.2, 25.2, 21.2, 20.9, 18.8, 17.1, 12.1, 12.0; MS (FD): 426 ($M^+$); Anal. Calcd. for $C_{29}H_{46}O_2$: C, 80.63; H, 10.87. Found: C, 81.77; H, 11.04. (NOTE: 76.91 ppm was used as reference)

35. Lithium $NH_3$ Reduction of 7-Oxo Stigmasterol

Tetrahydrofuran (500 ml) was added to a 2000 ml 3 neck flask equipped with a dry ice condenser, 250 ml addition funnel, and magnetic stir bar. The condenser and a bath surrounding the flask were charged with dry ice acetone, and ammonia was collected to a total volume of 1200 ml. Lithium wire (2 g, 288 mmol) was added to the solution with vigorous stirring. Once the lithium was completely dissolved, a solution of compound 60 (25 g, 58.6 mmol) in tetrahydrofuran (100 ml) was added to the flask in a steady stream. After 1 hour, the reaction mixture was quenched by the addition of $NH_4Cl$ and allowed to evaporate overnight. The resulting solid was dissolved in 500 ml toluene/1000 ml 1N HCl solution with vigorous stirring. After removal of the aqueous layer, the organic layer was washed with distilled water and brine, dried over $MgSO_4$, and evaporated. The residue was recrystallized from 2-propanol to yield compound 61 (19.4 g, 45.7 mmol, 78%): mp 149° C.; $^1$H NMR (200 MHZ, $CDCl_3$): δ 5.23–4.92 (m, 2H), 3.70–3.52 (m, 1H), 1.10 (s, 3H), 1.02 (d, J=6.5 Hz, 3H), 0.86–0.78 (m, 9H), 0.70 (s, 3H); $^{13}$C NMR (200 MHZ, $CDCl_3$): δ 212.0, 138.0, 129.3, 70.5, 55.1, 54.8, 51.1, 49.8, 48.8, 46.7, 46.0, 42.3, 40.1, 38.5, 37.7, 36.0, 35.9, 31.7, 30.9, 28.8, 25.2, 24.9, 21.7, 21.2, 20.9, 18.8, 12.1, 11.7; MS (FD): 428 ($M^{30}$): Anal. Calcd. for $C_{29}H_{48}O_2$: C, 81.25; H, 11.29. Found: C, 80.97; H, 11.20 (NOTE: 76.91 ppm was used as reference.).

36. K-Selectride® (potassium tri-sec-butylborohydride from Aldrich) Reduction of 7-Ketone Compound 61 (10 g, 23.4 mmol) was dissolved in dry tetrahydrofuran (50 ml) in a 250 ml round bottom flask under argon. The flask was chilled to –20° C., and 1 M K-Selectride® solution (potassium tri-sec-butylborohydride from Aldrich) in tetrahydrofuran (51.6 ml, 51.6 mmol) was slowly syringed into the flask. The reaction was allowed to stir overnight, warming to room temperature as the ice melted. The reaction was cooled in an ice bath and quenched with a 30% $H_2O_2$ solution until the color disappeared and evolution of gas ceased. Toluene (250 ml) was added to the solution, and the organic layer was washed with distilled water, 1 N HCl solution (2×250 ml), sodium bicarbonate solution, and brine. The organic layer was then dried, and the solvent was removed in vacuo. The resulting solid was then chromatographed on silica gel (elution with 60% ethyl acetate in hexane) to produce compound 62 (9.6 g, 22.4 mmol, 96%) as a white solid: mp 174° C.; $^1$H NMR (200 MHZ, $CDCl_3$): δ 5.22–4.92 (m, 2H), 3.82 (sharp m, 1H), 3.71–3.52 (m, 1H), 1.02 (d, J=6.5 Hz, 3H), 0.86–0.81 (m, 12H), 0.68 (s, 3H); $^{13}$C NMR (200 MHZ, $CDCl_3$): δ 138.1, 129.2, 71.0, 67.8, 55.8, 51.1, 50.5, 45.7, 42.4, 40.4, 39.4, 39.2, 37.6, 36.9, 36.6, 36.2, 35.4, 31.7, 31.2, 28.7, 25.2, 23.6, 20.9, 20.8, 18.8, 12.1, 11.9, 11.1; MS (FD): 430 ($M^+$); Anal. Calcd. for $C_{29}H_{50}O_2$: C, 80.87; H, 11.70. Found: C, 80.62; H, 11.76 (NOTE: 76.91 ppm was used as reference.).

37. Silver Carbonate on Celite® ($SiO_2$) Oxidation of 3B-ol

Silver carbonate on Celite® ($SiO_2$, available from Aldrich) was prepared by dissolving $AgNO_3$ (8.3 g, 49 mmol) in deionized water (250 ml) and adding Celite® (6.7 g, $SiO_2$ from Aldrich) to the solution. The solution was stirred vigorously to suspend the Celite® ($SiO_2$ from Aldrich). A large excess of a pH 11 carbonate buffer was slowly added to the slurry, and silver carbonate precipitated out onto the Celite® ($SiO_2$ from Aldrich) as a yellow-green solid. The solid was filtered, washed with deionized water, and dried in a foil covered vacuum desiccator overnight. The 3β-hydroxy sterol 62 (7 g, 16.3 mmol) was dissolved in toluene (600 ml) in a 1000 ml round bottom flask equipped with a Dean Stark trap. The silver carbonate was added to the flask, and the solution was refluxed for 8 hours. The reaction was cooled and filtered through a short column of Florisil® (elution with ethyl acetate) to insure complete elution of the sterol. Florisil® is a magnesium silicate material that is commercially available from Aldrich. The solvent was removed in vacuo to yield compound 63 (6.4 g, 15 mmol, 92%). The sterol was pure by TLC and NMR, but it was discolored due to elution of a trace of silver impurity from the Florisil® (magnesium silicate, available from Aldrich): mp 174–175° C.; $^1$H NMR (200 MHZ, $CDCl_3$): δ 5.23–4.92 (m, 2H), 3.84 (sharp m, 1H), 1.02 (d, J=6.5 Hz, 3H), 1.00 (s, 3H), 0.93–0.82 (m, 9H), 0.69 (s, 3H); $^{13}$C NMR (200 MHZ, $CDCl_3$): δ 211.6, 138.0, 129.3, 67.4, 55.8, 51.1, 50.4, 45.1, 44.0, 42.4, 40.4, 39.3, 39.2, 38.9, 38.0, 36.4, 35.6, 31.8, 28.8, 25.3, 23.6, 21.0, 18.9, 12.1, 11.9, 10.3; MS (FD): 428 ($M^{30}$); Anal. Calcd. for $C_{29}H_{48}O_2$: C, 81.25: H, 11.29. Found: C, 81.17; H, 11.49 (NOTE: 76.91 ppm was used as reference.).

38. Preparation of 7α-Benzoate (Compound 64)

A cold (0° C.) solution of compound 63 (5 g, 11.7 mmol) in pyridine (100 ml) was treated dropwise with benzoyl chloride (6.8 ml, 58.5 mmol). After the addition of 4-dimethylaminopyridine (200 mg), the reaction mixture was allowed to warm to room temperature, stirred for approximately 8 hours, and then poured over ice and allowed to stand overnight. The resulting solution was filtered, leaving the sterol behind as a thick waxy solid. The sterol was dissolved in toluene, and washed with 1N HCl solution (2×) and sodium bicarbonate solution. The resulting organic layer was dried over $MgSO_4$, filtered, and evaporated. The residue was purified by chromatography on silica gel (gradient elution with ethyl acetate in toluene) to yield compound 64 (5.33 g, 10.1 mmol, 86%) as a white solid: mp 155° C.; $^1$H NMR (200 MHZ, $CDCl_3$): δ 8.04–7.99 (m, 2H), 7.63–7.40 (m, 3H), 5.24–4.92 (m, 3H), 1.09 (s, 3H), 1.04 (d, J=6.5 Hz, 3H), 0.85–0.70 (m, 12H); $^{13}$C NMR (200 MHZ, $CDCl_3$): δ 210.8, 165.3, 137.8, 132.7, 130.4, 129.3, 129.2, 128.2, 71.0, 55.5, 50.9, 50.4, 46.8, 43.6, 42.3, 40.3, 40.1, 39.0, 38.3, 38.0, 37.8, 35.4, 33.2, 31.6, 28.5, 25.1, 23.4, 21.0, 20.9, 18.7, 12.0, 11.7, 10.3; MS (FD): 532 ($M^+$); Anal. Calcd. for $C_{36}H_{52}O_3$: C, 81.15; H, 9.84. Found: C, 80.98; H, 9.89 (NOTE: 76.91 ppm was used as reference.).

39. Preparation of 3-Dioxolane (Compound 65)

The ketone 64 (4 g, 7.5 mmol) was dissolved in toluene (250 ml), and was treated with p-toluenesulfonic acid (250 mg) and ethylene glycol (5 ml). The reaction mixture was heated to reflux with the removal of water for 2 hours, and then allowed to cool. The reaction was treated with anhydrous sodium carbonate (2 g) and water. The organic layer was washed with sodium bicarbonate (2×), deionized water, and brine; dried over $Na_2SO_4$; and evaporated to yield compound 65 (4.1 g, 7.1 mmol, 95%) as a light yellow waxy solid: mp 74° C.; $^1$H NMR (200 MHZ, $CDCl_3$): δ 8.14–8.04 (m, 2H), 7.63–7.40 (m, 3H), 5.23–4.92 (m, 3H), 3.87 (m, 4H), 1.00 (d, J=6.5 Hz, 3H), 0.89 (s, 3H), 0.81–0.70 (m, 12 H); $^{13}$C NMR (200 MHZ, $CDVl_3$): δ 165.8, 138.0, 132.6, 130.9, 129.5, 129.2, 128.3, 108.9, 71.8, 64.0, 55.6, 51.1, 50.7, 47.1, 42.4, 40.4, 39.3, 38.5, 37.2, 37.1, 35.6, 35.4, 33.1, 31.7, 31.1, 28.6, 25.2, 23.6, 21.0, 18.8, 12.1, 11.8, 10.4; MS (FD): 576 ($M^{30}$); Anal. Calcd. for $C_{38}H_{56}O_4$: C, 79.12; H, 9.78. Found: C, 78.89; H, 9.75 (NOTE: 76.91 ppm was used as reference.).

40. Ozonolysis of Compound 65

The sterol 65 (3.5 g, 6.1 mmol) was dissolved in 2/1 dichloromethane/ethanol (250 ml). The Welsbach apparatus was purged with oxygen at 7 psi (1 ml/min), and the water was turned on. The sterol solution was chilled in a dry ice ethanol bath. The ozonolyzer was set at 90 V and switched on. Ozone was bubbled into the magnetically stirred, chilled flask until a blue coloration was observed. The power was switched off, and oxygen was bubbled into the flask until the color dissipated. Trimethyl phosphite (5 ml, 42 mmol) was added to the reaction pot, and the ice bath was removed to allow the reaction mixture to warm to room temperature. The solvent was removed in vacuo and maintained at high vacuum overnight to remove any remaining trimethyl phosphite. The resulting white solid was chromatographed on silica gel (gradient elution with ethyl acetate in toluene) to give compound 29 (2.7 g, 5.5 mmol, 90%) as a white solid identical to that prepared previously by NMR.

Figure 17:
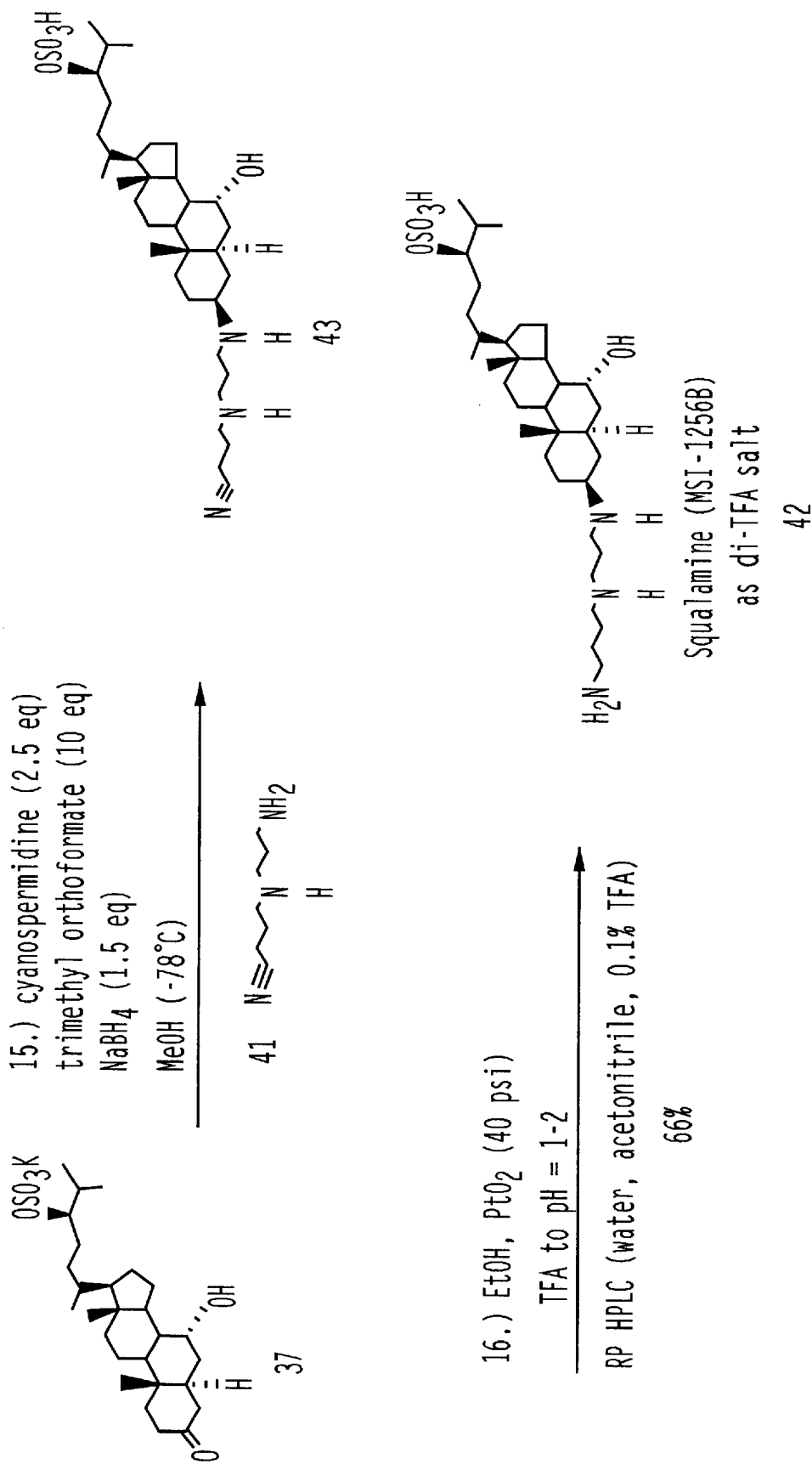
FIG. 17 illustrates a reaction mechanism for producing squalamine from steroid 37.

41. Preparation of Compound 41 (FIG. 17)

The following is an improved procedure over that published (Y. Umeda, M. Moriguchi, H. Kuroda, T. Nakamura, A. Fujii, H. Iinuma, T. Takeuchi, H. Umezawa, *J. of Antibiotics* 1987, 1303–1315). A flask containing 1,3-diaminopropane (2.5 kg, 33.72 mol) was stirred with a mechanical stirrer, cooled (−6° C.), and treated with 4-bromobutyronitrile (1.00 kg, 6.76 mol) over 1.5 hours, maintaining the internal temperature at less than 0° C. The reaction was allowed to stir in the cold bath for an additional 15 minutes. The cold bath was removed, and the reaction was allowed to stir without auxiliary temperature control for 1 hour. Isopropanol (11 L) was added in one portion to the reaction. The mixture was stirred for 15 minutes after the appearance of a precipitate, and then stored at 0–10° C. overnight. The solids were collected by filtration in a Buchner funnel lined with a polypropylene felt filter pad. The solids were washed with isopropanol (2×1.1 L). The combined filtrate was passed through an ion-exchange resin column.

The Dowex 1X8-100 ($^-$OH form) resin was prepared by combining Dowex 1X8-100 ($^-$Cl form, 2.2 kg) and aqueous 5 N NaOH (6 L) for one hour. The mixture was poured into a suitably sized chromatography column with a coarse glass frit. The resin was washed with 5 N NaOH (53 L). After washing with 44 L of 5 N NaOH, a small aliquot of the eluant, neutralized to pH 7 with HOAc, appeared hazy when aqueous 0.1 M $AgNO_3$ was added. The additional wash with 9 L of 5 N NaOH did not visibly improve clarity. The resin was washed with deionized water (6.6 L), at which time the pH of the eluant was 7. The eluant was clear after the addition of aqueous 0.1 M $AgNO_3$. The resin was washed with isopropanol (11 L), and the column was ready for use.

After the entire filtrate had passed through the column, the column was washed with isopropanol (14 L). A small aliquot of the combined eluant, when neutralized to pH 7 with HOAc, was clear after the addition of aqueous 0.1 M $AgNO_3$. The combined eluant was concentrated to a weight of 1.39 kg using a water aspirator and a bath at 45–50° C. Molecular sieves (100 g, 3 Å) were added to the residue, which was stored at 0–10° C. overnight. The sieves were removed by filtration, and the filtrate was distilled under reduced pressure in a 2 L flask equipped with overhead stirring, a thermometer, and a distillation head with a short Vigreaux column. Fractions distilling at less than 114° C. (0.6 mm) were collected and discarded (627 g). Two product fractions were collected containing pure compound 41: fraction 4 (108 g) distilled at 114–115° C. (0.6 mm) and fraction 5 (591 g, total=699 g, 73%) distilled at 110–112 (0.5 mm): $^1$H NMR (400 MHZ, $CDCl_3$): ä 2.71 (t, J=6.5 Hz, 2H), 2.68 (t, J=6.5 Hz, 2H), 2.61 (t, J=7 Hz, 2H), 2.39 (t, J=7 Hz, 2H), 1.75 (p, J=7 Hz, 2H), 1.56 (p, J=7 Hz, 2H); $^{13}$C NMR (100 MHZ, $CDCl_3$): ä 119.9, 48.1, 47.7, 40.5, 33.8, 25.8, 15.0; MS ($^+$FAB): 142 ($M^+$, 100); IR (neat, $cm^{-1}$): 3280, 2930, 2244, 1592, 1470, 1128, 830; Anal. Calcd. for $C_7H_{15}N_3$: C, 59.54; H, 10.71; N, 29.76. Found: C, 58.60, H, 10.52, N, 28.86.

42. Preparation of Compound 42 (Squalamine)

The polyamine 41 (8.00 g, 56.7 mmol) was dissolved in anhydrous methanol (650 ml) at room temperature, and trimethyl orthoformate (50 ml, 457 mmol) was added. Steroid 37 (10.0 g, 18.7 mmol) was added, and the reaction mixture was stirred for 18 hours. The reaction mixture was cooled to −74° C., treated with sodium borohydride (1.06 g, 28.0 mmol) over one minute, and stirred for 3.5 hours at −74° C. The reaction was allowed to warm to room temperature and was concentrated at 31° C. under a water aspirator vacuum. The crude product was dissolved in 100% ethanol (290 ml), purged with nitrogen, and acidified to pH 1–2 with neat trifluoroacetic acid. Platinun oxide (1.00 g) was added, and the mixture was shaken on a Parr apparatus (40 psi) for 18 h. The reaction mixture was filtered through paper, which was washed with methanol (620 ml). The filtrate was evaporated and then dissolved in 50% ethanol in water.

A propyl sulfonic acid ion exchange column was prepared by suspending 80 g of resin in 10% isopropanol (IPA) in water to form a slurry and by adding 200 ml of 10% IPA to the column, followed by the slurry. At least five column volumes of 10% IPA were eluted through the column at a flow rate of 40 ml/min. The column was washed with 0.05% trifluoroacetic acid (TFA) in 50% ethanol in water (150 ml) at 20 ml per min. The sample from above was loaded (in two batches), and the eluant was collected. The column was washed with two column volumes of 0.05% TFA in 50% ethanol in water and two column volumes of 0.05% TFA in 10% IPA. The column was then eluted with 4.5 M KOAc/ 10% IPA (pH 5), and the fractions were collected (150 ml each). Fractions that contained squalamine by TLC (6:3:1, dichloromethane:methanol:ammonium hydroxide) were combined.

The crude material from ion exchange was purified on a 25×5 cm YMC ODS-AQ C18 reversed phase column. The eluant from PSA was diluted with four volumes of deionized water. The column was loaded with squalamine and eluted with four column volumes of buffer A (0.05% TFA in 1% acetonitrile in water). Then the column was eluted with the following gradient of buffers A and B (0.05% TFA in 1% water in acetonitrile)(Detector: UV ë=200 nm):

| min | ml/min | % A | % B |
|---|---|---|---|
| 0 | 0 | 100 | 0 |
| 1:00 | 100 | 100 | 0 |
| 10:00 | 100 | 75 | 25 |
| 60:00 | 100 | 60 | 40 |
| 70:00 | 100 | 40 | 60 |
| 80:00 | 100 | 20 | 80 |
| 90:50 | 100 | 20 | 80 |
| 98:00 | 100 | 100 | 0 |
| 99:00 | 0 | 100 | 0 |

Between 28 and 60 minutes (30–40% B), fractions were collected (50 ml). All fractions were examined by TLC, and the early and late fractions were analyzed by analytical HPLC with ortho-phthalaldehyde (OPA) derivitization, a reverse phase column, and fluorescence detection. Fractions that were >95% pure were combined to afford 97% pure compound 42 (10.3 g, 60% yield) as the TFA salt (approximate FW 910), that was identical to natural squalamine by anal. HPLC (OPA method); $^1$H NMR (CD$_3$OD, 400 MHZ): ä 4.12 (br q, 1H), 3.76 (br s, 1H), 3.2–2.9 (m, 9H), 2.1–1.0 (m, 33H), 0.94–0.90 (m, 9H), 0.84 (s, 3H), 0.67 (s, 3H); and $^{13}$C NMR (CD$_3$OD, 100 MHZ): ä 86.7, 68.4, 59.2, 57.7, 51.8, 46.8, 46.0, 43.9, 43.0, 41.2, 40.1, 38.7, 38.0, 37.8, 37.5, 37.0, 32.7, 32.2, 32.1, 29.5, 28.3, 26.1, 25.7, 24.7, 24.6, 24.3, 22.3, 19.6, 18.6, 18.3, 12.6, 11.7.

In describing the invention, applicant has stated certain theories in an effort to disclose how and why the invention works in the manner in which it works. These theories are set forth for informational purposes only. Applicants do not wish to be bound by any specific theory of operation.

While the invention has been described in terms of various specific preferred embodiments and specific examples, those skilled in the art will recognize that various changes and modifications can be made without departing from the spirit and scope of the invention, as defined in the appended claims.

What is claimed is:

1. A method for producing an aminosterol compound selected from the group consisting of, compound 1436, and salts thereof, the method comprising:

converting, under sufficient conditions, a compound according to formula 129:

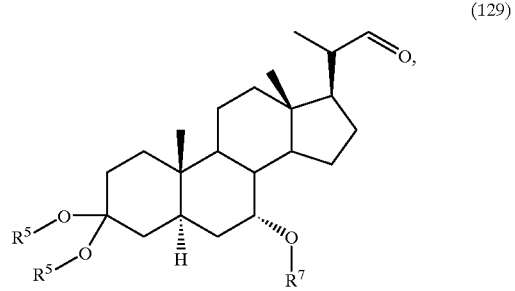

(129)

wherein the $R^5$ groups are suitable protecting groups that can be the same or different, or the $R^5$ groups can join together to form a ring structure, and $R^7$ is a suitable protecting group, to a compound according to formula 134:

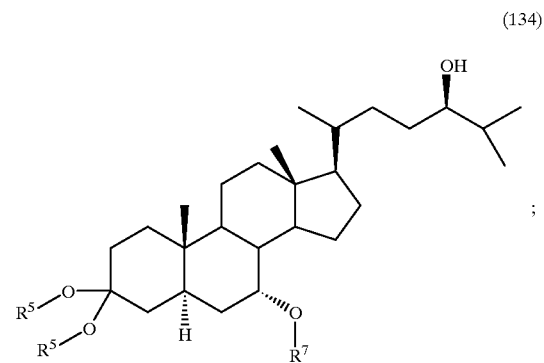

(134)

converting, under sufficient conditions, the compound according to formula 134 to a compound according to formula 135:

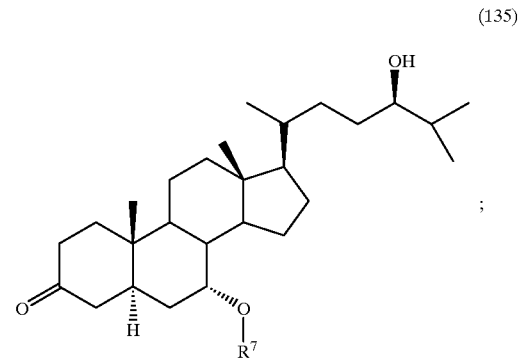

(135)

converting, under sufficient conditions, the compound according to formula 135 to a compound according to formula 136:

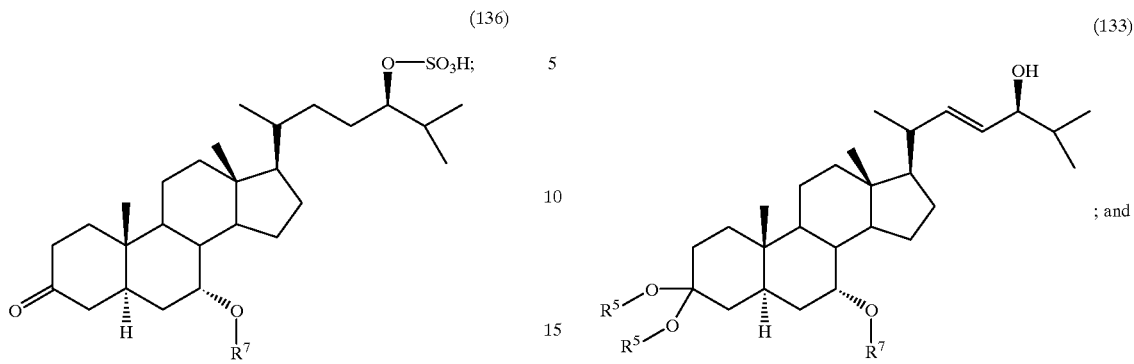

converting, under sufficient conditions, the compound according to formula 136 to a compound according to formula 37:

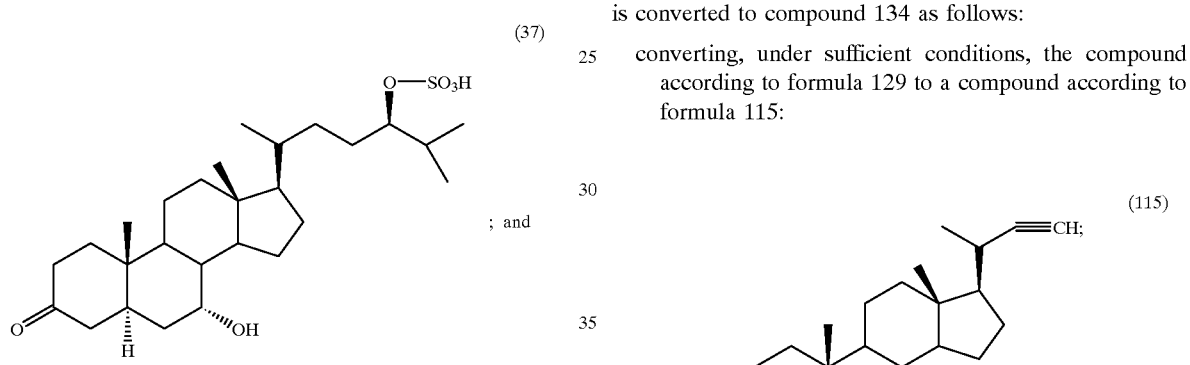

converting, under sufficient conditions, the compound according to formula 37 to compound 1436, or a salt thereof.

2. A method according to claim 1, wherein compound 129 is converted to compound 134 as follows:

converting, under sufficient conditions, the compound according to formula 129 to a compound according to formula 132:

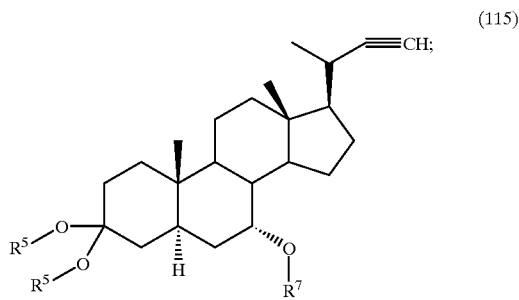

converting, under sufficient conditions, the compound according to formula 132 to a compound according to formula 133:

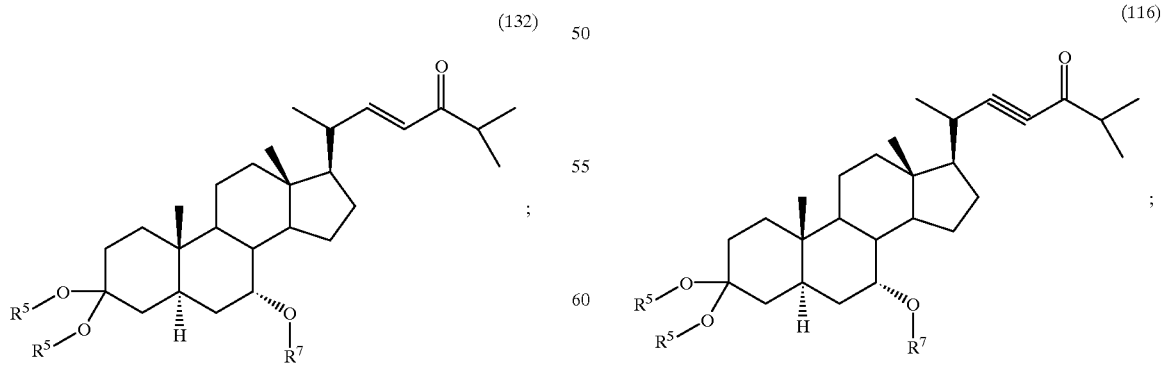

converting, under sufficient conditions, the compound according to formula 133 to the compound according to formula 134.

3. A method according to claim 1, wherein compound 129 is converted to compound 134 as follows:

converting, under sufficient conditions, the compound according to formula 129 to a compound according to formula 115:

converting, under sufficient conditions, the compound according to formula 115 to a compound according to formula 116:

converting, under sufficient conditions, the compound according to formula 116 to a compound according to formula 117:

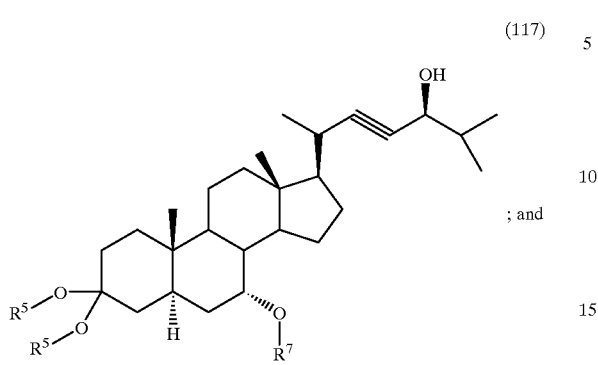
(117)

; and converting, under sufficient conditions, the compound according to formula 117 to the compound according to formula 134.

4. A method according to claim 1, wherein the compound according to formula 129 is produced as follows:

converting, under sufficient conditions, a compound according to formula 21 as follows:

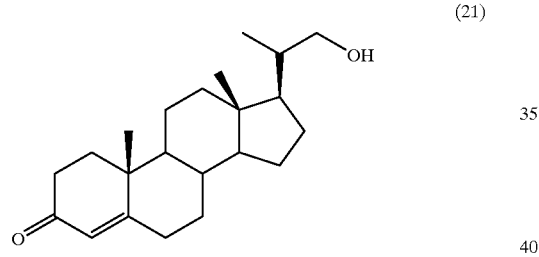
(21)

to a compound according to formula 122:

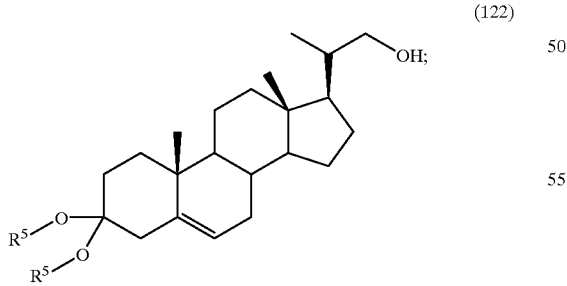
(122)

converting, under sufficient conditions, the compound according to formula 122 to a compound according to formula 123:

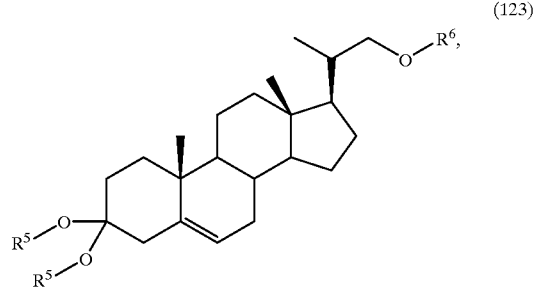
(123)

wherein $R^6$ is a suitable protecting group;

converting, under sufficient conditions, the compound according to formula 123 to a compound according to formula 124:

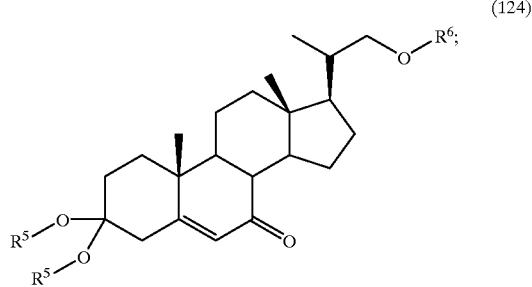
(124)

converting, under sufficient conditions, the compound according to formula 124 to a compound according to formula 125:

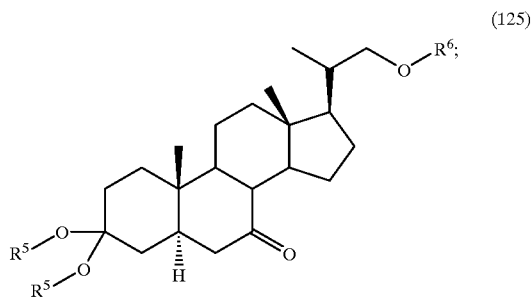
(125)

converting, under sufficient conditions, the compound according to formula 125 to a compound according to formula 126:

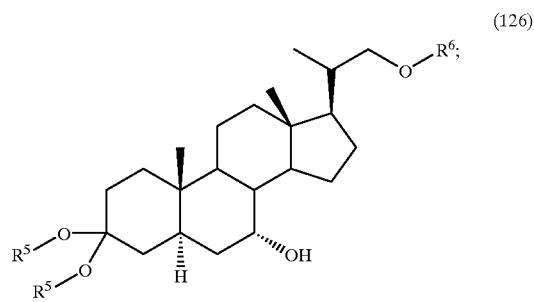
(126)

converting, under sufficient conditions, the compound according to formula 126 to a compound according to formula 127:

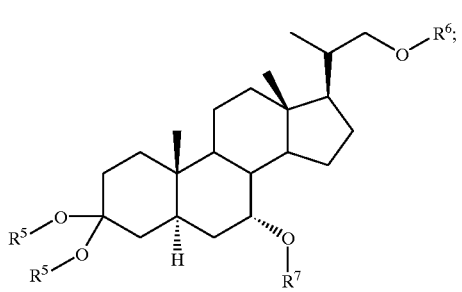
(127)

converting, under sufficient conditions, the compound according to formula 127 to a compound according to formula 128:

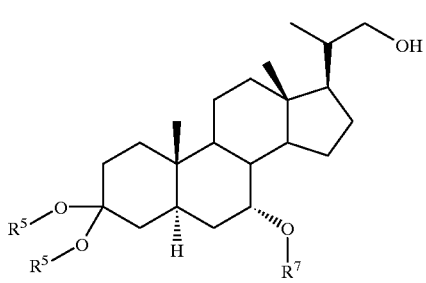
(128)

; and converting, under sufficient conditions, the compound according to formula 128 into the compound according to formula 129.

5. A method according to claim 1, wherein the compound according to formula 129 is a compound according to formula 29:

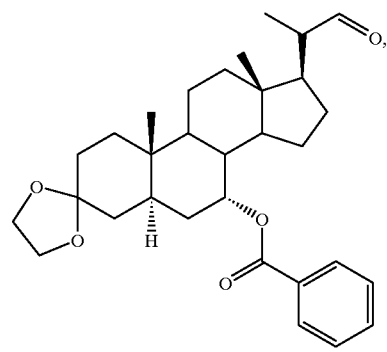
(29)

which is produced as follows:

converting, under sufficient conditions, a compound according to formula 21 as follows:

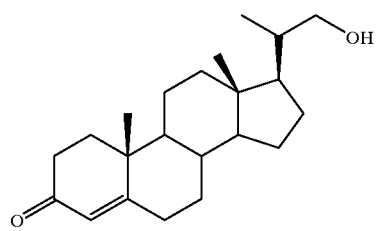
(21)

to a compound according to formula 22:

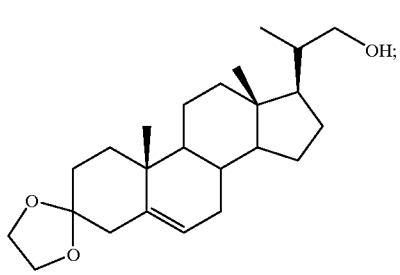
(22)

converting, under sufficient conditions, the compound according to formula 22 to a compound according to formula 23:

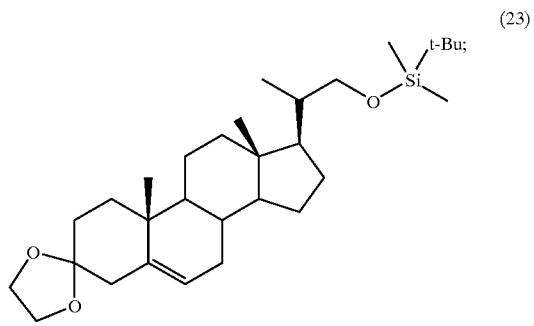
(23)

converting, under sufficient conditions, the compound according to formula 23 to a compound according to formula 24:

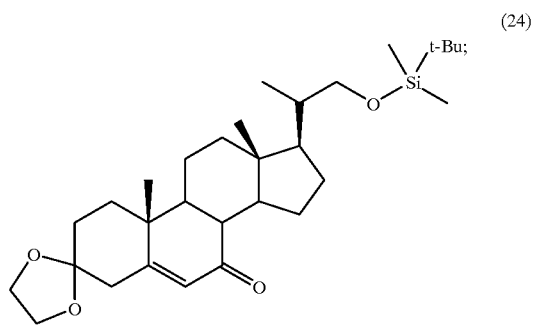
(24)

converting, under sufficient conditions, the compound according to formula 24 to a compound according to formula 25:

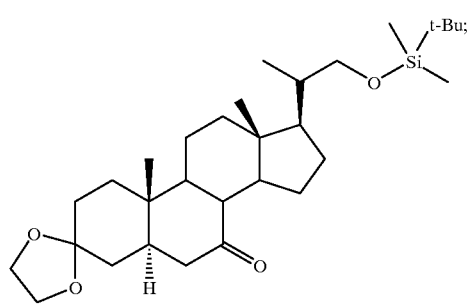

(25)

converting, under sufficient conditions, the compound according to formula 25 to a compound according to formula 26:

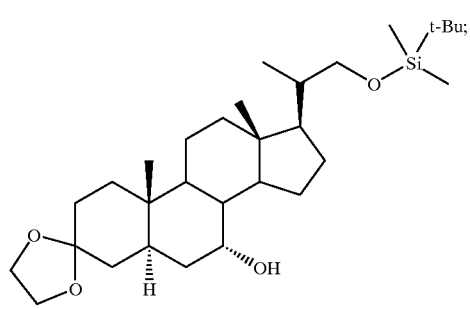

(26)

converting, under sufficient conditions, the compound according to formula 26 to a compound according to formula 27:

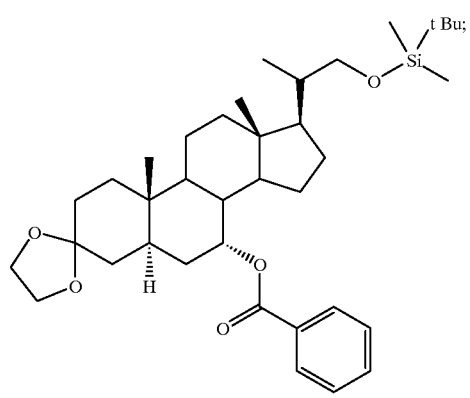

(27)

converting, under sufficient conditions, the compound according to formula 27 to a compound according to formula 28:

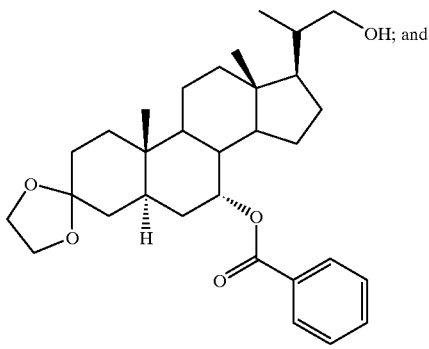

(28)

converting, under sufficient conditions, the compound according to formula 28 into the compound according to formula 29.

6. A method according to claim 1, wherein the compound according to formula 129 is produced as follows:

converting, under sufficient conditions, a compound according to formula 50 as follows:

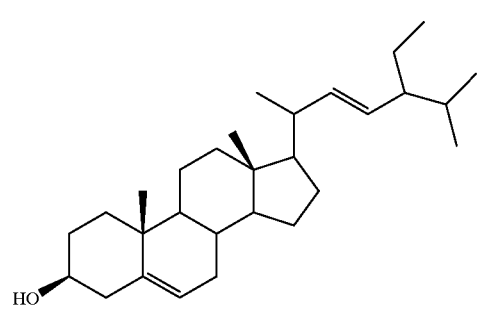

(50)

to a compound according to formula 60:

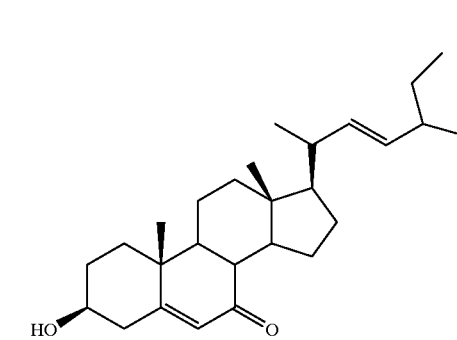

(60)

converting, under sufficient conditions, the compound according to formula 60 to a compound according to formula 61:

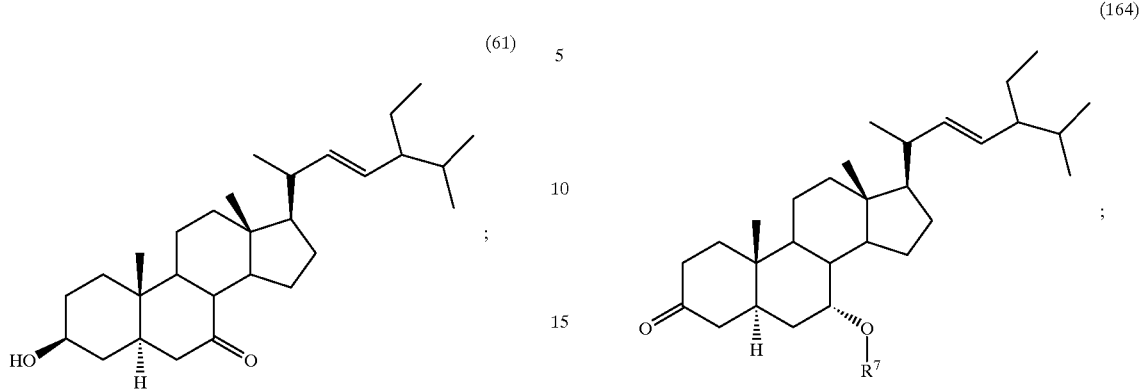

converting, under sufficient conditions, the compound according to formula 61 to a compound according to formula 62:

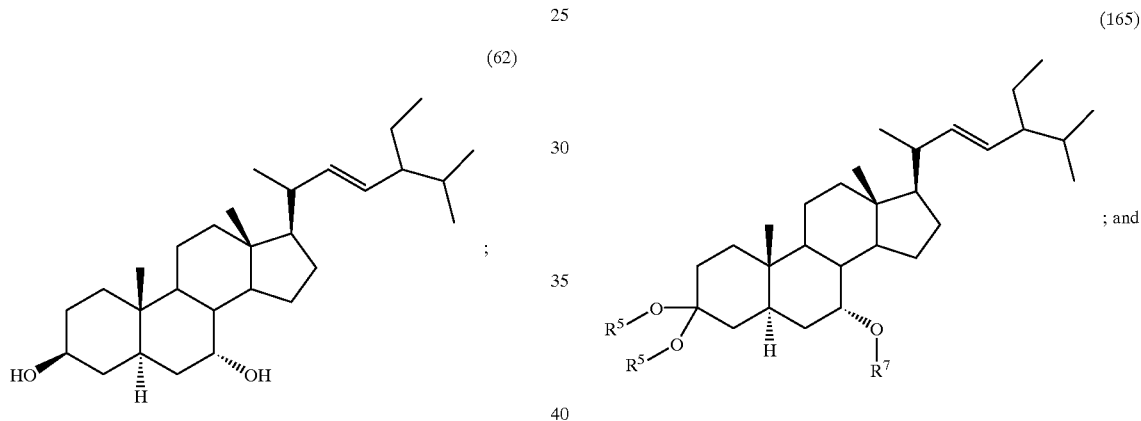

converting, under sufficient conditions, the compound according to formula 62 to a compound according to formula 63:

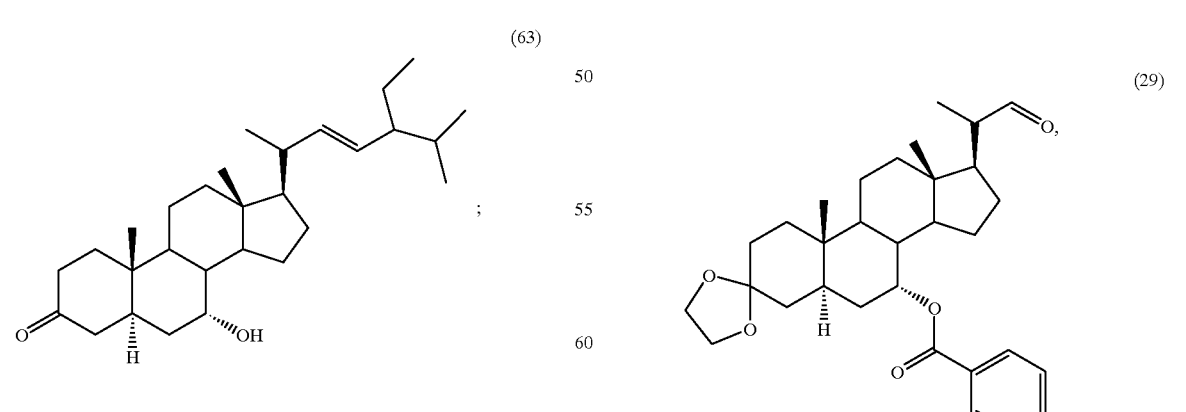

converting, under sufficient conditions, the compound according to formula 63 to a compound according to formula 164:

converting, under sufficient conditions, the compound according to formula 164 to a compound according to formula 165:

converting, under sufficient conditions, the compound according to formula 165 to the compound according to formula 129.

7. A method according to claim 1, wherein the compound according to formula 129 is a compound according to formula 29:

which is produced as follows:

converting, under sufficient conditions, a compound according to formula 50 as follows:

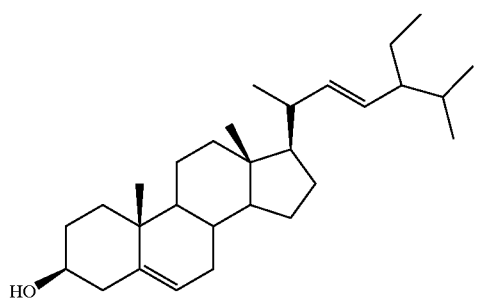
(50)

to a compound according to formula 60:

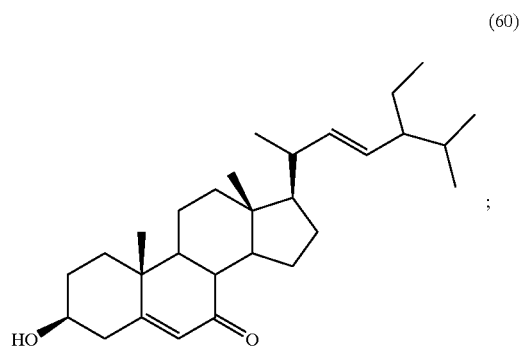
(60)

converting, under sufficient conditions, the compound according to formula 60 to a compound according to formula 61:

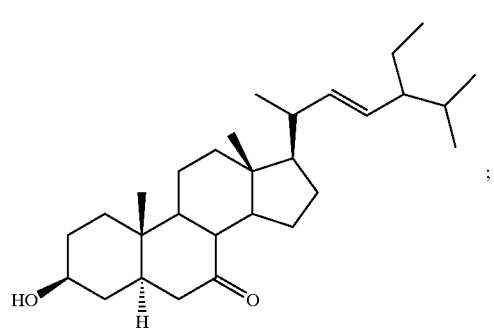
(61)

converting, under sufficient conditions, the compound according to formula 61 to a compound according to formula 62:

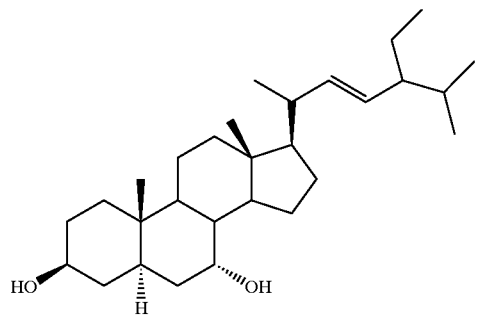
(62)

converting, under sufficient conditions, the compound according to formula 62 to a compound according to formula 6:

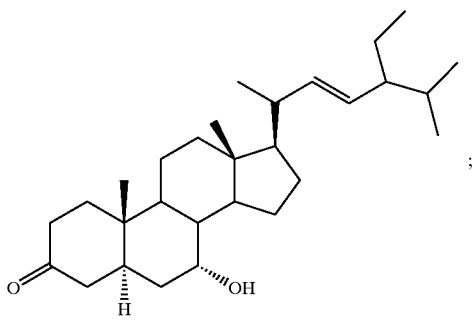
(63)

converting, under sufficient conditions, the compound according to formula 63 to a compound according to formula 64:

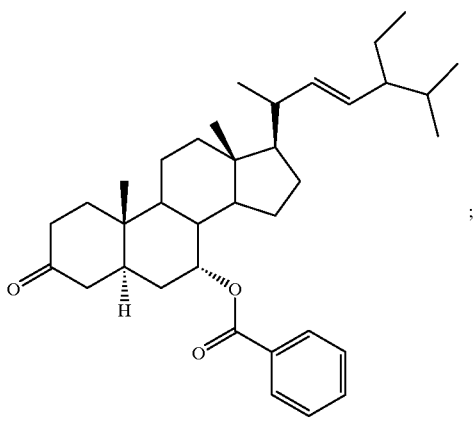
(64)

converting, under sufficient conditions, the compound according to formula 64 to a compound according to formula 65:

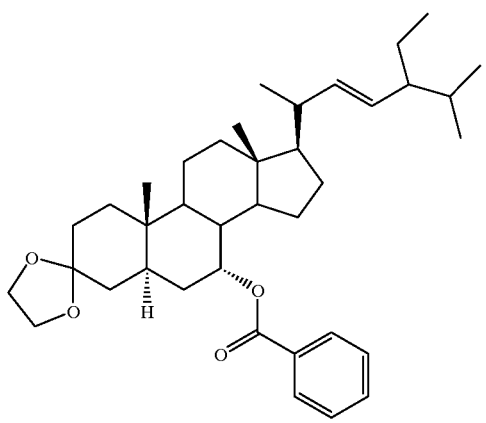

(65)

; and converting, under sufficient conditions, the compound according to formula 65 to the compound according to formula 29.

8. A method according to claim 1, wherein the compound according to formula 129 is a compound according to formula 29:

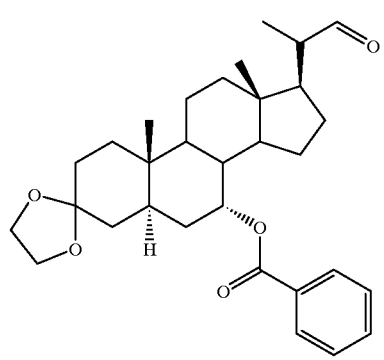

(29)

, and the compound according to formula 134 is a compound according to formula 34:

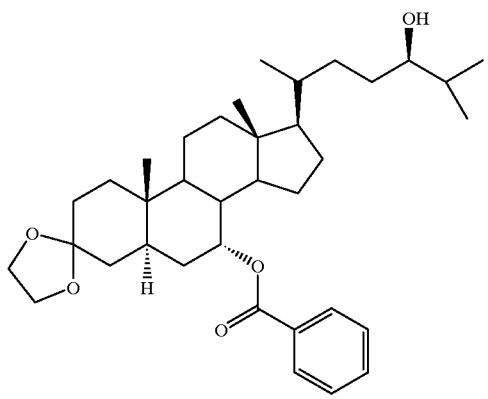

(34)

, wherein the compound according to formula 34 is produced by converting the compound according to formula 29, under sufficient conditions, to a compound according to formula 32:

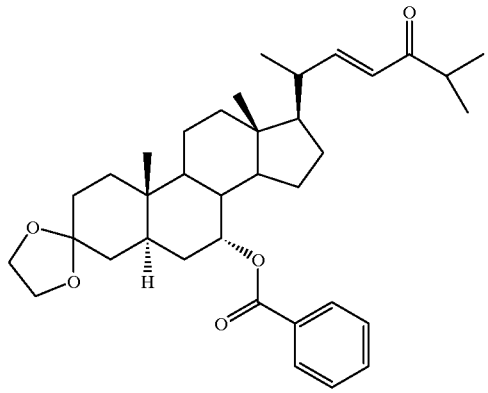

(32)

;

converting, under sufficient conditions, the compound according to formula 32 to a compound according to formula 33:

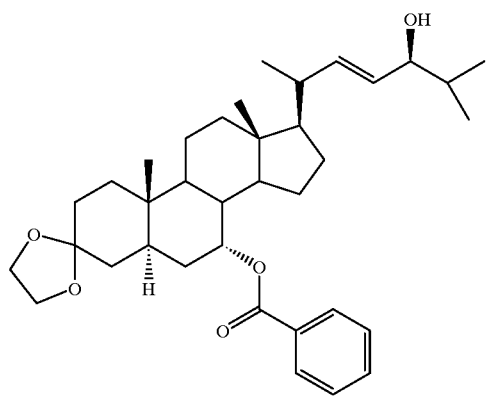

(33)

; and converting, under sufficient conditions, the compound according to formula 33 to the compound according to formula 34.

9. A method according to claim 8, wherein the compound according to formula 135 is as follows:

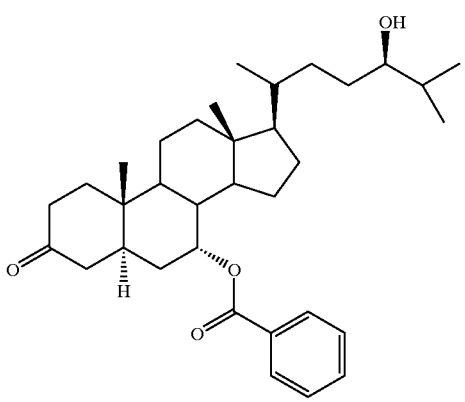

10. A method according to claim 9, wherein the compound according to formula 136 is as follows:

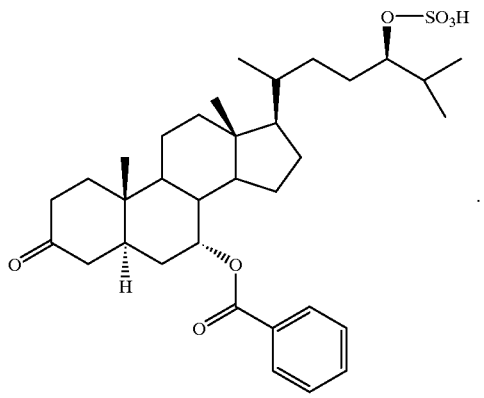

11. A method for producing an aminosterol compound selected from the group consisting of squalamine and salts thereof, the method comprising:

converting, under sufficient conditions, a compound according to formula 129:

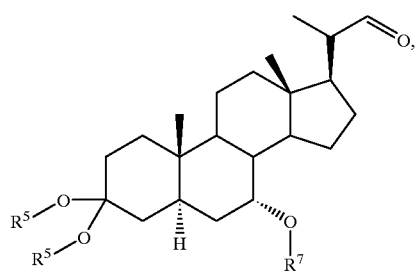

wherein the $R^5$ groups are suitable protecting groups that can be the same or different, or the $R^5$ groups can join together to form a ring structure, and $R^7$ is a suitable protecting group, to a compound according to formula 134:

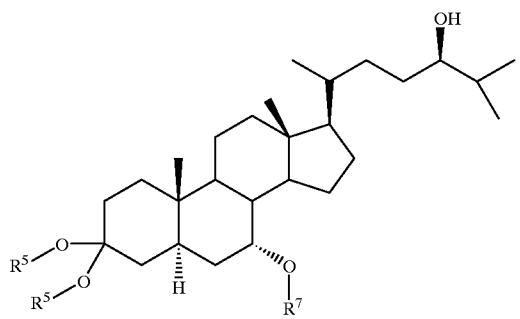

converting, under sufficient conditions, the compound according to formula 134 to a compound according to formula 135:

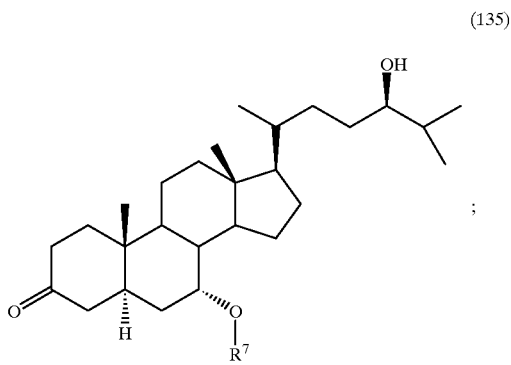

converting, under sufficient conditions, the compound according to formula 135 to a compound according to formula 136:

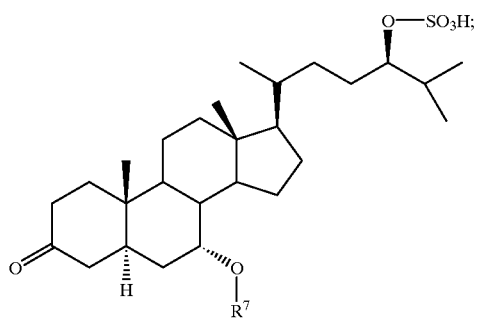

converting, under sufficient conditions, the compound according to formula 136 to a compound according to formula 37:

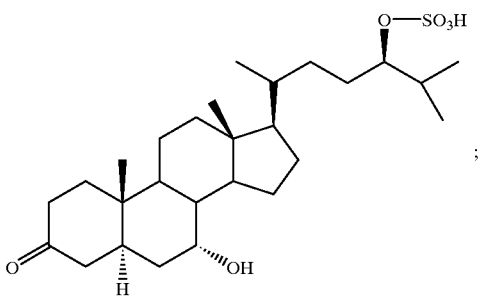

converting, under sufficient conditions, the compound according to formula 37 into its corresponding potassium salt;

converting, under sufficient conditions, the potassium salt of the compound according to formula 37 into a compound according to formula 43:

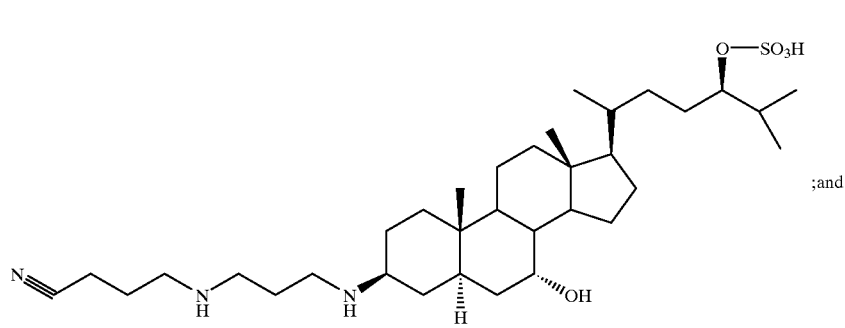
converting, under sufficient conditions, the compound according to formula 43 to squalamine or a salt thereof.
* * * * *